(12) United States Patent
Abels et al.

(10) Patent No.: US 6,733,286 B2
(45) Date of Patent: *May 11, 2004

(54) SELF-LIGATING ORTHODONTIC BRACKETS THAT HAVE MULTIPLE INITIALLY OPEN ARCH WIRE SLOTS LIGATABLE WITH A SINGLE COVER

(76) Inventors: Norbert Abels, Talstrasse 7, 66424 Homburg (DE); Claus H. Backes, St. Wendeler Strasse 45, 66113 Saarbrücken (DE)

( * ) Notice: Subject to any disclaimer, the term of this patent is extended or adjusted under 35 U.S.C. 154(b) by 92 days.

This patent is subject to a terminal disclaimer.

(21) Appl. No.: 09/952,826
(22) Filed: Sep. 12, 2001

(65) Prior Publication Data

US 2002/0110774 A1 Aug. 15, 2002

Related U.S. Application Data

(63) Continuation-in-part of application No. 09/914,737, filed as application No. PCT/EP01/08489 on Jul. 23, 2001, now abandoned, application No. 09/952,826, which is a continuation-in-part of application No. 09/784,525, filed on Feb. 15, 2001, now Pat. No. 6,607,383.

(51) Int. Cl.$^7$ .................................................. A61C 3/00
(52) U.S. Cl. ........................................... 433/11; 433/15
(58) Field of Search ........................... 433/8, 9, 10, 11, 433/12, 13, 14, 15, 16, 17

(56) References Cited

U.S. PATENT DOCUMENTS

| | | | |
|---|---|---|---|
| 2,011,575 A | | 8/1935 | Ford |
| 2,230,315 A | * | 2/1941 | Winslow ..................... 433/11 |
| 3,128,552 A | | 4/1964 | Broussard |
| 3,218,713 A | | 11/1965 | Wallshein |
| 3,724,074 A | | 4/1973 | Wallshein |
| 3,748,740 A | | 7/1973 | Wildman |

(List continued on next page.)

FOREIGN PATENT DOCUMENTS

| | | |
|---|---|---|
| DE | 1 184 451 | 12/1964 |
| DE | 23 57 573 | 5/1975 |
| DE | G 91 12 872.2 | 3/1992 |
| DE | 296 08 349 U1 | 11/1996 |
| EP | 0 714 639 A3 | 5/1996 |
| EP | 0 714 639 A2 | 6/1996 |
| WO | WO 94/00072 | 1/1994 |
| WO | WO 00/33760 | 6/2000 |
| WO | WO 00/76419 | 12/2000 |

OTHER PUBLICATIONS

Konstruieren mit unststoffen, Gunter Erhard, Carl Hanser Verlag München Wien, pp. 314–329, 1999.

*Primary Examiner*—John J. Wilson
(74) *Attorney, Agent, or Firm*—Workman Nydegger

(57) ABSTRACT

Self ligating orthodontic brackets include a bracket base and a ligation cover which interacts with the base in order to provide ligation of at least one arch wire associated with the base. The orthodontic brackets may include one or more of the following improved features: (1) a film hinge about which a ligation cover may rotate; (2) a bearing spring or other flexible feature associated with the ligation cover to provide active ligation; (3) a ligation cover that has sufficient flexibility and resilience to facilitate locking and unlocking relative to the base; (4) a spring or spring-like feature that provides resistance to rotation of the ligation cover relative to the base; (5) a bracket base and ligation cover formed from different types of plastic materials; (6) two or more initially open arch wire slots that can be ligated by a single ligation cover; or (7) a safety locking feature that holds the ligation cover more tightly to the bracket in response to increased arch wire pressure. The orthodontic brackets may comprise one or more different materials, such as plastic, metal or ceramic and may be manufactured as a single piece or in multiple pieces that are later joined together.

21 Claims, 27 Drawing Sheets

U.S. PATENT DOCUMENTS

| | | | |
|---|---|---|---|
| 3,775,850 A | * 12/1973 | Northcutt | 433/16 |
| 3,854,207 A | 12/1974 | Wildman | |
| 4,077,126 A | 3/1978 | Pletcher | |
| 4,103,423 A | 8/1978 | Kessel | |
| 4,144,642 A | 3/1979 | Wallshein | |
| 4,171,568 A | 10/1979 | Förster | |
| 4,180,912 A | 1/1980 | Kesling | |
| 4,279,593 A | 7/1981 | Röhlcke | |
| 4,371,337 A | 2/1983 | Pletcher | |
| 4,419,078 A | 12/1983 | Pletcher | |
| 4,492,573 A | 1/1985 | Hanson | |
| 4,527,975 A | 7/1985 | Ghafari et al. | |
| 4,559,012 A | 12/1985 | Pletcher | |
| 4,559,013 A | 12/1985 | Amstutz et al. | |
| 4,597,739 A | 7/1986 | Rosenberg | |
| 4,614,497 A | 9/1986 | Kurz | |
| 4,634,662 A | 1/1987 | Rosenberg | |
| 4,655,708 A | 4/1987 | Fujita | |
| 4,687,441 A | 8/1987 | Klepacki | |
| 4,698,017 A | 10/1987 | Hanson | |
| 4,712,999 A | 12/1987 | Rosenberg | |
| 4,786,252 A | 11/1988 | Fujita | |
| 4,846,681 A | 7/1989 | Mourany et al. | |
| 4,850,865 A | 7/1989 | Napolitano | |
| 4,859,179 A | 8/1989 | Kesling | |
| 4,913,654 A | 4/1990 | Morgan et al. | |
| 5,037,296 A | 8/1991 | Karwoski | |
| 5,062,794 A | 11/1991 | Miura | |
| 5,078,596 A | 1/1992 | Carberry et al. | |
| 5,094,614 A | 3/1992 | Wildman | |
| 5,125,832 A | 6/1992 | Kesling | |
| 5,160,260 A | 11/1992 | Chang | |
| 5,161,969 A | 11/1992 | Pospisil et al. | |
| 5,174,754 A | 12/1992 | Meritt | |
| 5,224,858 A | 7/1993 | Hanson | |
| 5,269,681 A | * 12/1993 | Degnan | 433/11 |
| 5,275,557 A | 1/1994 | Damon | |
| 5,322,435 A | 6/1994 | Pletcher | |
| 5,344,315 A | 9/1994 | Hanson | |
| 5,380,197 A | 1/1995 | Hanson | |
| 5,429,499 A | 7/1995 | Sernetz | |
| 5,456,599 A | 10/1995 | Hanson | |
| 5,470,228 A | 11/1995 | Franseen et al. | |
| 5,474,445 A | 12/1995 | Voudouris | |
| 5,474,446 A | 12/1995 | Wildman et al. | |
| 5,556,276 A | 9/1996 | Roman et al. | |
| 5,562,444 A | 10/1996 | Heiser et al. | |
| 5,586,882 A | 12/1996 | Hanson | |
| 5,630,715 A | 5/1997 | Voudouris | |
| 5,630,716 A | 5/1997 | Hanson | |
| 5,685,711 A | 11/1997 | Hanson | |
| 5,711,666 A | 1/1998 | Hanson | |
| 5,738,513 A | 4/1998 | Hermann | |
| 5,857,849 A | 1/1999 | Kurz | |
| 5,863,199 A | 1/1999 | Wildman | |
| 5,885,074 A | 3/1999 | Hanson | |
| 5,906,486 A | 5/1999 | Hanson | |
| 5,964,589 A | 10/1999 | Musich | |
| 6,017,118 A | 1/2000 | Gasvoda et al. | |
| 6,042,373 A | 3/2000 | Hermann | |
| 6,042,374 A | 3/2000 | Farzin-Nia et al. | |
| 6,071,119 A | 6/2000 | Christoff et al. | |

* cited by examiner

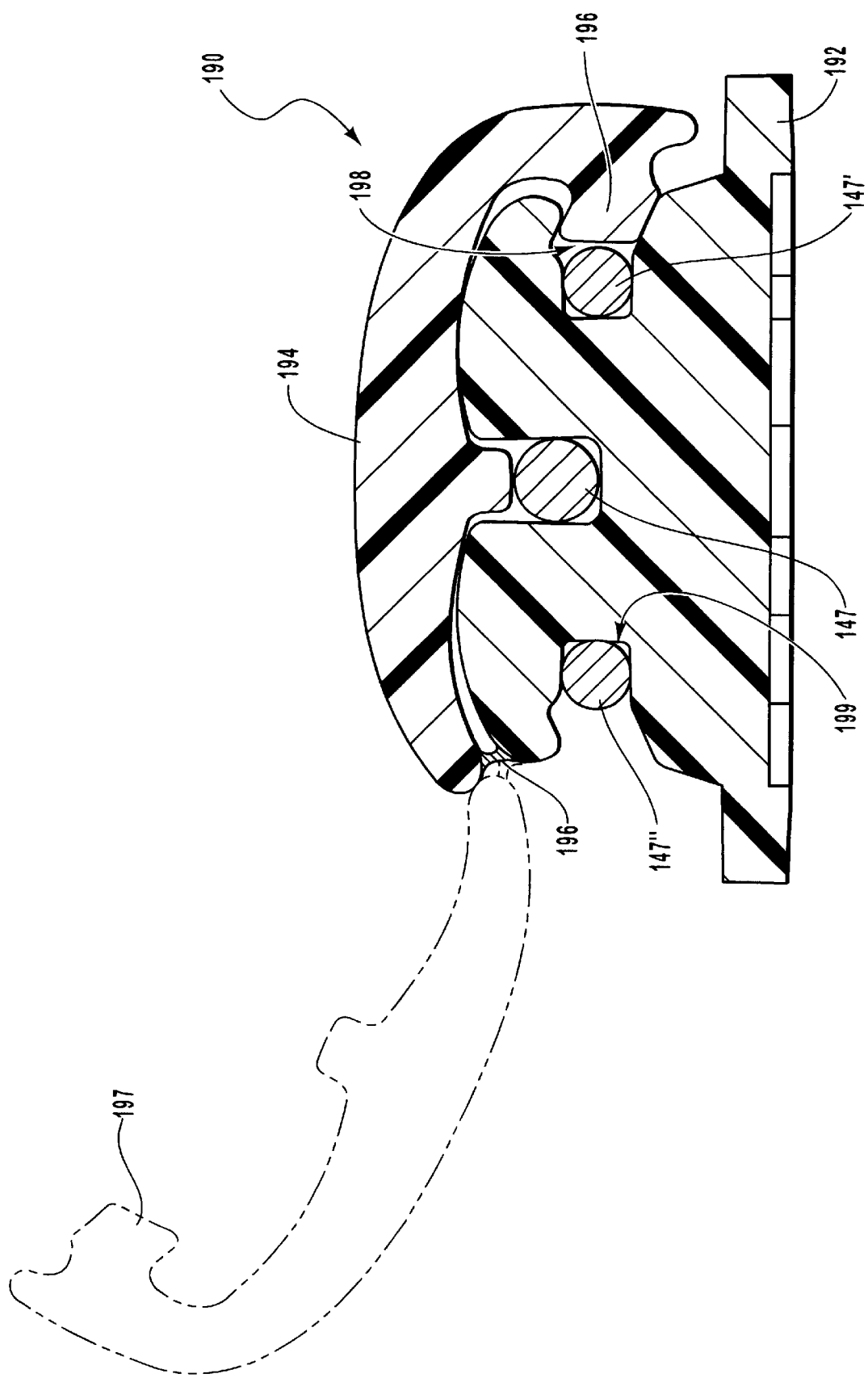

SELF-LIGATING ORTHODONTIC BRACKETS THAT HAVE MULTIPLE INITIALLY OPEN ARCH WIRE SLOTS LIGATABLE WITH A SINGLE COVER

RELATED APPLICATIONS

This application is a continuation-in-part of U.S. application Ser. No. 09/914,737, filed Aug. 29, 2001, now abandoned in the names of Norbert Abels and Claus H. Backes, and entitled "ORTHODONTIC BRACKET", which is a national phase application filed under 35 U.S.C. §371 of PCT application No. PCT/EP01/08489, filed Jul. 23, 2001. This application is also a continuation-in-part of U.S. application Ser. No. 09/784,525, filed Feb. 15, 2001, now U.S. Pat. No. 6,607,383 in the names of Norbert Abels and Claus H. Backes, and entitled "AN ORTHODONTIC BRACKET". For purposes of disclosure, the foregoing applications are incorporated herein by reference.

BACKGROUND OF THE INVENTION

1. The Field of the Invention

The present invention relates to orthodontic brackets, more particularly to self-ligating orthodontic brackets that include a bracket base, at least one slot or other feature for receiving an arch wire, and a ligation cover.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct underbites or overbites ("buck teeth"). Orthodontic treatment can improve the patient's occlusion, or enhanced spatial matching of corresponding teeth.

The most common form of orthodontic treatment involves the use of orthodontic brackets and wires, which together are commonly referred to as "braces". Orthodontic brackets, more particularly the bracket bases, are small slotted bodies configured for direct attachment to the front (or "labial") surfaces of the patient's anterior, cuspid, and bicuspid teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment. End sections of the arch wire are typically captured within tiny appliances known as "buccal tubes" affixed to the patient's molars.

There are two distinct classes of orthodontic brackets: those that require the use of ligatures to fasten the arch wire to the bracket, and those that are self-ligating. Before the emergence of self-ligating brackets, small ligature wires or elastomeric bands were necessary to hold the arch wire in a securely seated position in the brackets. Ligatures or some other form of fastening means are essential to ensure that the tensioned arch wire is properly positioned around the dental arch, and to prevent the wire from being dislodged from the bracket slots during chewing of food, brushing of teeth, or application of other forces. One type of commercially available ligature is a small, elastomeric O-ring, which is installed by stretching the O-ring around small wings known as "tie wings" that are connected to the bracket body. Metal ligatures may also be used to retain arch wires within the bracket slots.

In an effort to simplify the process of installing braces, various self-ligating brackets have been developed. The term "self-ligating bracket" refers to a class of orthodontic brackets that include some sort of ligation cover or clasp which encloses or otherwise retains the arch wire within the slot of the base. There are both "passive" and "active" self-ligating orthodontic brackets. The term "passive" bracket refers to brackets that only loosely retain the arch wire therein, such that considerable movement between the arch wire and bracket base is possible. The term "active" bracket refers to brackets in which the self-ligating arch wire cover exerts force onto the arch wire, resulting in more precise and controlled tooth movement.

The first self-ligating bracket, known as the Russell bracket, was developed by Dr. Jacob Stolzenberg in the early 1930s. This bracket, which uses a set screw to ligate the arch wire within a slot of a threaded base, was revolutionary but perhaps ahead of its time because the concept of self-ligating brackets fell more or less into obscurity until the early 1970s.

In 1971, Dr. Jim Wildman of Eugene, Oregon developed the EDGELOK bracket, which has a round body with a rigid labial sliding cap. A special opening tool is used to move the slide occlusally for arch wire insertion. When the cap is closed over the arch wire with finger pressure, the bracket slot is converted to a tube. The EDGELOK bracket was the first "passive" self-ligating bracket. That is, the bracket, while retaining the arch wire therein, does not exert pressure onto the wire. Instead, the arch wire is free to slide relative to the bracket. The EDGELOK bracket is describe in U.S. Pat. Nos. 3,748,740 and 3,854,207 to Wildman. Other patents to Dr. Wildman include U.S. Pat. Nos. 5,094,614, 5,474,446 and 5,863,199. In 1998, Dr. Wildman introduced the TWIN-LOCK bracket, which includes a flat, rectangular slide, housed between the tie wings of an edgewise twin bracket.

A similar bracket to the EDGELOK bracket, called the MOBIL-LOCK bracket, was developed by Dr. Franz Sander of Ulm, Germany, which requires a special tool to rotate the semicircular labial disk into the open or closed position.

Between 1976 and 1980, Dr. Herbert Hanson of Hamilton, Ontario, Canada developed the SPEED bracket, which features a curved spring clip that wraps occluso-gingivally around a miniaturized bracket body. The clip is moved occlusally using special tools to permit arch wire placement, then seated gingivally using finger pressure. The clip constrains and interacts with the arch wire to some degree such that the SPEED bracket was the first "active" bracket system.

In 1986, Dr. Erwin Pletcher developed the ACTIVA bracket, which has an inflexible, curved arm that rotates occluso-gingivally around a cylindrical bracket body (see U.S. Pat. Nos. 4,077,126, 4,371,337, 4,419,078, 4,522,490, 4,559,012 and 5,322,435 to Pletcher). The arm can be opened and closed using finger pressure.

In 1995, Dr. Wolfgang Heiser of Innsbrück, Austria developed the TIME bracket, which is similar in appearance to the SPEED bracket, and which features a rigid, curved arm that wraps occluso-gingivally around the labial aspect of the bracket body. A special instrument is used to pivot the arm either gingivally into the slot-open position, or occlusally into the slot-closed position. The stiffness of the bracket arm prevents any substantial interaction with the arch wire, thereby making the TIME bracket a passive bracket.

Dr. Dwight Damon of Spokane, Wash. developed the Damon SL I and the Damon SL II brackets in 1996 and 1999, respectively (see U.S. Pat. No. 6,071,118 to Damon). Both are edgewise twin brackets. The difference between the two is that the first features a labial cover that straddled the tie wings, while the second incorporates a flat, rectangular slide between the tie wings. In both versions, the slide moves incisally on the maxillary brackets and gingivally on the mandibular brackets. Special opening and closing pliers are required to move the slide.

There are many other variations and adaptations of the foregoing self-ligating brackets that have been developed by others. See, e.g., U.S. Pat. No. 4,786,252 to Fujita, U.S. Pat. No. 4,712,999 to Rosenberg, U.S. Pat. No. 4,492,573 to Hanson, U.S. Pat. No. 4,103,423 to Kessel, and U.S. Pat. No. 6,071,119 to Christoffet al.

In general, conventional self-ligating brackets are complicated in design, complex to assemble, and difficult to use in practice. Conventional orthodontic brackets often require many trips to the orthodontist for periodic readjustment and maintenance. Therefore, there has been a long-felt need to find new designs and materials that can simplify the manufacture of orthodontic brackets, as well as the installation and subsequent maintenance of such brackets. In particular, there is a need for orthodontic brackets that are easy to open and close, that provide active ligation without the need for special tools to open and close the arch wire restraining means, which are easily manufactured and installed by the orthodontist, which provide greater versatility together, and which are of simplified design.

For example, it would be an improvement in the art to provide one-piece, self-ligating orthodontic brackets that can be manufactured in a single molding step. It would be a further improvement to provide self-ligating brackets that include a plurality of plastic materials from which the base and cover can be made so as to maximize the beneficial properties of each plastic material. It would be an additional improvement to provide orthodontic brackets with special hinge and locking features between the ligation cover and bracket base or increased safety and ease of use. It would be an improvement to provide orthodontic brackets capable of dynamic active ligation of an arch wire as the tooth is realigned so as to reduce or eliminate the need for subsequent adjustments. It would yet be an improvement to provide orthodontic brackets having two or more initially open arch wire slots that can be ligated by a single ligation cover. It would also be an improvement to provide a ligation cover that was biased so as to preferentially remain in an open and/or closed position.

Orthodontic brackets that incorporate one or more of the these and other improvements are disclosed and claimed herein.

SUMMARY OF THE INVENTION

The orthodontic brackets according to the present invention encompass one or more of the improvements and features disclosed herein, which result in a generally low-cost bracket that is simple to manufacture, compact in construction, and easy to install and adjust. In general, the orthodontic brackets according to the invention will include at least one of the following improved features:

1. a ligation cover that includes a film hinge, which is a localized area of reduced cross-sectional thickness, about which at least a portion of the ligation cover can rotate so as to open and close relative to the bracket base;
2. a spring element extending from an underside of the ligation cover and that is able to absorb mechanical energy from an arch wire and then release such energy over time to provide continuous active ligation of the arch wire;
3. a general spring feature associated with, or incorporated into, the ligation cover that is able to absorb mechanical energy from the arch wire and then release such energy over time in order to provide dynamic active ligation of an arch wire associated with a bracket base;
4. an orthodontic bracket that includes a deformable or flexible ligation cover that facilitates locking and unlocking of the cover relative to a bracket base that includes a lip, overhang or other structure within which the ligation cover can be slideably inserted or withdrawn;
5. a spring element interconnecting the ligation cover and bracket base that urges the ligation cover to remain open while in an open position and/or to remain closed while in a closed position relative to the bracket base;
6. a ligation cover that is biased toward remaining open when in an open position and toward remaining closed while in a closed position, such that positive pressure or force is required to selectively open and close the cover each time, and such that the cover is optionally able to apply a ligation force onto an arch wire associated with the bracket even when the ligation cover is not securely locked to the bracket base;
7. an orthodontic bracket that is manufactured using two-color molding of different types of plastic materials, such as a harder, more durable plastic for the bracket base and a more flexible and resilient plastic for the ligation cover;
8. an orthodontic bracket that includes at least two initially open arch wire slots configured to accept or receive two or more separate arch wires that can be at least partially occluded by a single ligation cover in a single action of locking or closing the ligation cover relative to the bracket base so as to ligate the arch wires; or
9. an orthodontic bracket having a safety locking feature that provides enhanced locking of the ligation cover to the bracket in response to increased pressure by an arch wire bearing upwardly against a ligation cover.

In general, depending on which of the foregoing features are incorporated into a particular orthodontic bracket, the orthodontic bracket may provide either passive or active ligation of an arch wire associated with the bracket base. The bracket may include a bracket base and ligation cover may be molded as a single, unitary piece, or else formed separately and then joined together. The ligation cover may or may not include specific hinge structures or regions, but may instead bend or flex along a substantial length of the ligation cover. An orthodontic bracket may be manufactured from a single plastic or metal material, or from multiple materials, such as metal and plastic or two or more plastics. The ligation cover may be flexible or rigid. The bracket base may include a single arch wire slot or it may include multiple arch wire slots. In some cases, the ligation cover will be designed to cover a single arch wire slot and in others, it may ligate two or more open slots. In some cases, one or more slots may be provided that are not ligated by the ligation cover such that conventional ligatures may be required to ligate additional arch wires disposed therein. Unless otherwise specified or restricted, any feature known in the art of orthodontic brackets, bases and ligation covers may be used in conjunction with a particular orthodontic bracket that encompasses at least one of the improved features summarized above and disclosed more fully hereinafter.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only exemplary embodiments of the invention and are not therefore to be considered to be limiting of its scope, the invention will be described and explained with additional specificity and detail through the use of the accompanying drawings, in which:

FIG. 18C shows an alternative embodiment of a hinged, two-piece orthodontic bracket having the special locking feature of the orthodontic bracket of FIGS. 13–15 and a separate hinge material interconnecting the ligation cover and bracket base;

DETAILED DESCRIPTION OF THE PREFERRED EMBODIMENTS

I. Introduction and Definitions

Figure 1A:
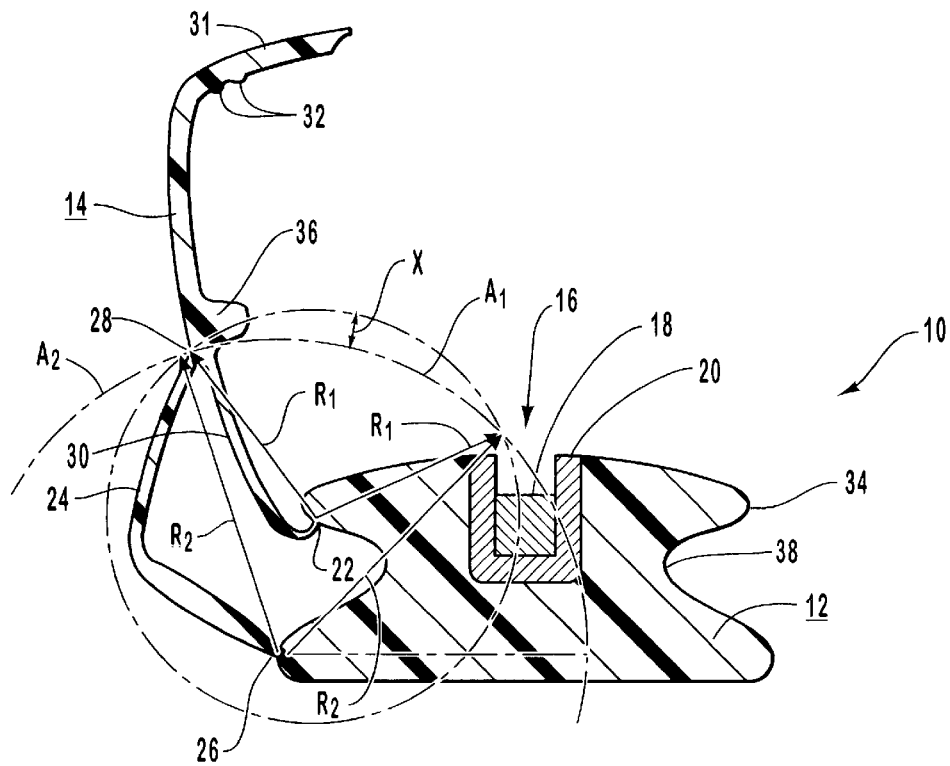
FIG. 1A is a cross-section view of a hinged, one-piece orthodontic bracket that includes a bracket base, a ligation cover, and a spring element interconnecting the ligation cover and bracket base, with the cover being "open" relative to the arch wire slot of the base.

The present invention encompasses a number of separate but interrelated inventive concepts and embodiments that greatly improve the ease, simplicity and efficiency with which a dental practitioner can attach and adjust orthodontic appliances known as orthodontic brackets, commonly referred to as "braces". They also increase the effectiveness of treatment and reduce discomfort by the patient. In many cases, the inventive orthodontic brackets are less expensive to manufacture, since they are amenable to being injection molded from plastic in a single step.

By greatly reducing the time, cost and effort in manufacturing and installing orthodontic brackets, the present invention makes it possible for orthodontic brackets and procedures to be more widely available to the less affluent. Their increased comfort compared to conventional brackets also makes them more attractive to all users of orthodontic brackets.

The orthodontic brackets according to the invention include a bracket base and a ligation cover or clasp. The ligation cover can be selectively opened in order to permit the insertion of an arch wire into an arch wire slot or other feature within the base and then closed or locked in order to retain the arch wire within the slot or other feature.

The orthodontic brackets according to the invention include both passive and active ligating brackets (i.e. those in which the ligation cover exerts pressure onto the arch wire and covers that do not), brackets in which the bracket base and ligation cover are manufactured as one unitary piece and those in which the base and cover are formed separately and then joined together, covers that have specifically formed hinge structures or regions (e.g., film hinges or pivot pins) and those with no specific hinge structure or region, brackets made of a single material (e.g., plastic or metal) and those comprising multiple materials (e.g., plastic and metal and/or two or more different plastics), covers that are flexible and those that are rigid, bases that include a single arch wire slot and those that include two or more slots, bases in which ligation of the arch wire is only possible by closing or locking the ligation cover and those that also include structures that permit optional ligation using conventional ligatures.

The orthodontic brackets may optionally include one or more special features, such as leaf springs and the like, that extend from the cover toward the arch wire slot in order to provide dynamic active ligation as the arch wire is more fully seated within the arch wire slot over time. They may alternatively include a more rigid protrusion extending from a flexible ligation cover that is able to absorb mechanical energy from the arch wire and then transfer such energy over time to the tooth in order to provide dynamic active ligation in a different manner. The brackets may optionally include a special safety locking feature between the base and cover that results in a tightening of the cover to the base in response to increasing upward pressure from the arch wire to the cover. The brackets may optionally include a spring feature that urges a closed cover to remain closed and/or an open cover to remain open, such that positive force is required to move the cover from an open position to a closed position and/or from a closed position to an open position.

The terms "orthodontic bracket" and "bracket", for purposes of this disclosure and the appended claims, and unless otherwise specified or limited, shall be broadly understood as referring to an orthodontic appliance that can be attached to, and used to straighten, a tooth. Unless otherwise specified or limited, such "orthodontic brackets" will, at a minimum, include a bracket base and a ligation cover. Unless otherwise specified or limited, the terms "orthodontic bracket" and "bracket" shall not be understood as implying the use of any particular type of material, the inclusion of any particular design feature, the ability to provide any particular function, or any constraint as to its mode of use.

The terms "bracket base" and "base", for purposes of this disclosure and the appended claims, and unless otherwise specified or limited, shall be understood as referring to that portion of an orthodontic bracket that is attached to a tooth and that includes at least one slot or other structural feature for receiving or holding an arch wire therein. The term "bracket base" shall be understood as encompassing any of the exemplary bases disclosed herein, as well as any bracket bases known in the art of orthodontics, unless otherwise specified or limited. Unless otherwise specified or limited, the term "base" shall not be understood as implying the use of any particular type of material, the inclusion of any particular design feature, the ability to provide any particular function, or any constraint as to its mode of use.

The term "arch wire slot", for purposes of this disclosure and the appended claims, and unless otherwise specified or limited, shall be understood as referring to any depression, groove, enclosure, region, or space adjacent one or more protrusions or raised portions within the base of an orthodontic bracket that is designed so as to at least partially receive an arch wire therein or thereat. The "arch wire slots" according to the invention are not limited to any particular size, shape or arrangement. The term "arch wire slot" shall be understood as encompassing any of the exemplary arch wire slots disclosed herein, as well as any arch wire slots known in the art of orthodontics, unless otherwise specified or limited.

The term "arch wire", for purposes of this disclosure and the appended claims, and unless otherwise specified or limited, shall be understood as referring to any initially straight or curved wire or elongated structure that is used to interconnect at least one orthodontic bracket with another orthodontic bracket or structure for the purpose of realigning one or more misaligned teeth. The term "arch wire" shall be understood as encompassing any of the exemplary arch wires disclosed herein, as well as any arch wires known in the art of orthodontics, unless otherwise specified or limited.

Unless otherwise specified or limited, the term "arch wire" shall not be understood as implying the use of any particular type of material, the inclusion of any particular design feature such as size or cross-sectional shape, or the ability to provide any particular function other than the application of straitening forces onto one or more misaligned teeth.

The term "ligation cover", for purposes of this disclosure and the appended claims, and unless otherwise specified or limited, shall be understood as referring to that portion of an orthodontic bracket that is used to hold, lock, affix or otherwise retain an arch wire within at least a portion of the slot, structural feature or region within the base for receiving or holding arch wires, e.g., by at least partially occluding one or more arch wire slots. Unless otherwise specified or limited, such "ligation covers" may be designed so as to cover all or any portion of the arch wire slot, and all or any portion of the base, so long as ligation of the arch wire occurs while the ligation cover is in a closed or locked position relative to the base. The term "ligation cover" shall be understood as encompassing any of the exemplary ligation covers disclosed herein, as well as any ligation cover known in the art of orthodontics, unless otherwise specified or limited. Unless otherwise specified or limited, the term "ligation cover" shall not be understood as implying the use of any particular type of material, the inclusion of any particular design feature, the ability to provide any particular function other than to selectively ligate and release at least one arch wire, or any constraint as to the manner in which it is attached to the base.

The term "hinge", for purposes of this disclosure and the appended claims, and unless otherwise specified or limited, shall be understood as referring to any of one or more structural features or regions within a ligation cover, or between a ligation cover and base, that permits the ligation cover to pivot or rotate relative to the bracket base to which it is attached. Thus, a "hinge" may define a region where one end of a ligation cover is hingedly attached to a bracket base, and/or a center point or line about which the ligation cover may rotate. Hinges may also interconnect a spring with a ligation cover and/or a bracket base. The term "hinge" shall be understood as encompassing any of the exemplary hinges disclosed herein, as well as any hinge known in the orthodontic or general mechanical arts, unless otherwise specified or limited. Unless otherwise specified or limited, the term "hinge" shall not be understood as implying the use of any particular type of material, the inclusion of any particular design feature, or the ability to provide any particular functions other than those commonly provided by hinges in general.

The term "latch for locking the ligation cover to the base" (or for brevity, "latch member" or "cover locking clasp"), for purposes of this disclosure and the appended claims, and unless otherwise specified or limited, shall be understood as comprising any locking device, mechanism, slot, recess, flange or protrusion, or any set of interlocking, overlapping or interacting mechanical features that serve to secure an initially free, rotatable or flexible end of a ligation cover to the bracket base, such as to achieve ligation of an arch wire located at least partially within an arch wire slot. Such "latch members" or "cover locking clasps" may advantageously permit selective locking and unlocking of the ligation cover to the base, although permanent or irreversibly locking "latches" or "clasps" may be used within the scope of the invention. Even though the terms "latch" or "clasp" may, in some cases, refer to specific mechanical features that are integrally part of the ligation cover and base, they are not so limited and may include additional mechanical structures or features that are separate from the ligation cover and base. Thus, the terms "latches" or "clasps" shall be understood as encompassing any of the exemplary locking clasps or latches disclosed herein, as well as any locking latch or clasp known in the orthodontic or general mechanical arts, unless otherwise specified or limited. Unless otherwise specified or limited, the terms "latch" and "clasp" shall not be understood as implying the use of any particular type of material, the inclusion of any particular design feature, or the ability to provide any particular functions other than those commonly provided by locking clasps in general.

The term "spring", for purposes of this disclosure and the appended claims, and unless otherwise specified or limited, shall be understood as comprising any device or material that generally tends to assume a particular conformation when relaxed, and which requires the application of an external force in order for the spring to assume a different conformation, such as being compressed or elongated. The term "spring" includes any device or material that, when compressed, elongated or otherwise manipulated by a force so that it is no longer in a relaxed conformation, continuously exerts an opposing force until it reassumes the relaxed conformation such that it is capable of storing mechanical energy. Hence, unless otherwise specified or limited, the term "spring" shall be broadly understood as encompassing any "energy storing springs" disclosed herein and also any such springs known in the orthodontic and general mechanical arts.

Nevertheless, the term "spring" may, in some cases where specified, also include those devices and materials that are said to have "elastic memory" such that they can become at least partially "relaxed" when forced to assume a particular conformation over a time sufficient for any initially opposing forces to at least partially subside. In other words, there are polymers and other materials that, when assuming an original relaxed conformation, initially resist and exert a force opposite to a conformation-changing force but which, over time, can become substantially relaxed in a new conformation such that they may actually resist a conformation-changing force that seeks to return the material to the original conformation. Hence, the term "spring" may, in some cases, also refer to materials that possess such "elastic memory".

For the sake of simplicity, directional terms such as "top", "bottom", "up", "down", "upper", "lower", and "under side", for purposes of this disclosure and the appended claims, shall be understood in reference to a tooth surface upon which an orthodontic bracket is attached or is intended to be attached, with the tooth surface lying "beneath" the bracket, and the bracket sitting "above" the tooth surface. Thus, unless otherwise specified, it shall be assumed that any direction moving away from the tooth surface is "up" and any direction moving toward the tooth surface is "down". In general, the ligation cover extends over at least a portion of an "upper" surface or region of the bracket base when in a locked position. The surface or region of the bracket base that most closely approaches or is adjacent the tooth surface is the "bottom" or "under side" of the base. The region or side of the ligation cover that is adjacent to the bracket base while in a locked position is the "under side" of the cover.

II. Orthodontic Brackets

The orthodontic brackets according to the invention generally include a bracket base and a ligation cover. The base is the portion of the orthodontic bracket that is attached or adhered to a tooth. The exemplary bases depicted in the drawings and described more fully below include one or more arch wire slots that are able to receive or generally hold or retain an arch wire in an initially unligated fashion. The ligation cover is the mechanism or means by which an arch wire is ligated or held in place within the arch wire slot. Alignment forces exerted by one or more arch wires to the base and/or cover are transferred to the tooth in order to urge the tooth into proper alignment. The present invention contemplates the use of a wide variety of different bracket bases and ligation covers having varying mechanical and functional features. The following discussing is intended to merely exemplify specific embodiments or species of the larger genus of bracket bases and ligation covers that can be used in making the orthodontic brackets according to the invention. It should be understood that virtually any base and ligation cover known in the art, in view of the teachings disclosed herein, can be used or modified so as to function in a manner contemplated by the present invention.

A. Materials

The bracket bases and ligation covers according to the invention can be made from any suitable material, or groups of materials, having desired properties, such as strength, rigidity, durability, flexibility, resilience, moldability, or machinability. Two suitable classes of materials that are widely used in making bases and ligation covers include metals and plastics. Ceramics or other rigid materials may alternatively be used in manufacturing bases for use in the invention. In the case of plastics or ceramics, strengthening fibers may be added to increase the strength, toughness and resiliency of the finished base and/or ligation cover.

A suitable metal that may be used to manufacture bases and ligation covers includes, for example, stainless steel. The metals selected for use in making the base should be safe when employed in the oral cavity. In other words, metals that are dangerous when ingested should generally be avoided unless they are somehow encapsulated or otherwise prevented from diffusing in significant quantity into the person's saliva.

Suitable plastics for making bases and ligation covers include, but are not limited to, polyoxymethylene, PEEK, polycarbonates, PET, other polyesters, polyamides, polyaramides, and the like. For the sake of brevity, the term "plastic" shall broadly include thermoplastic and thermoset materials. The term "plastic" may be used to describe virtually any organic polymer or copolymer having suitable properties of moldability and hardenability. In general, harder plastics are generally preferred in order to provide a rigid, stable bracket base. Of course, virtually any plastic that can safely be employed in a person's mouth, and that has sufficient strength, toughness and rigidity for use as a base, is within the scope of the invention. Whereas softer, more flexible plastics such as polyethylene and polypropylene are generally less suitable for use in making the bracket base, since it is typically desirable for the base to have high hardness and durability, they may be advantageously employed in the manufacture of ligation covers, particularly where it is desired for a ligation cover to be more flexible than the bracket base.

As will be discussed more fully below, the bracket base and ligation cover can be made from the same material. In some cases it may be more cost effective from the standpoint of manufacturing costs, as well as providing greater ease of use, to mold the base and cover as a single piece. In the case where a more rigid plastic is used in making the base, and a more flexible plastic is used in making the cover, it will typically be advantageous to separately mold the bracket base and ligation cover and then thermally fuse them together to form a single, integrally connected bracket. This procedure is sometimes referred to in the art of molding as "two-color molding", which refers to the fact that two different plastic materials are molded or fused together to form a single integral, or one-piece, article of manufacture.

As will be discussed more fully below, the ligation cover and base may be joined together using bridging fibers or a fabric to form a flexible joint. In such a case, the fibers or fabric may advantageously be partially embedded within the material used to form the base and ligation cover (e.g., plastic) while in a plastic or molten state.

It is within the scope of the invention to employ a combination of two or more materials when making an orthodontic bracket, such as a metal base and plastic ligation cover or, alternatively, a plastic base and metal ligation cover. Two or more materials such as plastic and metal may be used in making the base, or in making the ligation cover, with each material performing a function that is unique and specific to that material. Separately formed metal materials may be joined together, for example, by means of one or more mechanical fasteners (e.g., hinges, rivets, pins, screws, interlocking pieces, etc.), welds, adhesives or cements. As more fully discussed below, a plastic base may be reinforced with metal attachments or inserts to provide greater durability and wear life, particularly where a metal implement (e.g., an arch wire) makes forceful contact with the base. The ligation cover may likewise incorporate a metal feature that comes into direct contact with the arch wire to provide greater durability. A material that more readily accepts adhesives may be used on the bottom of the base next to the tooth.

B. Exemplary Orthodontic Brackets

FIGS. 1–26 depict exemplary orthodontic brackets that incorporate one or more of the inventive concepts disclosed herein. Based on the specific descriptions of the exemplary brackets, together with the general principles set forth herein, one of ordinary skill in the art will be readily able to modify any of the exemplary brackets to include any other features described or suggested herein, either generally or in the context of a different embodiment. Moreover, one of ordinary skill will readily appreciate that existing orthodontic brackets may also be readily modified, in light of the advantages that will become apparent when reading the present description, so as to incorporate one or more of the inventive concepts or features disclosed herein.

Figure 1B:
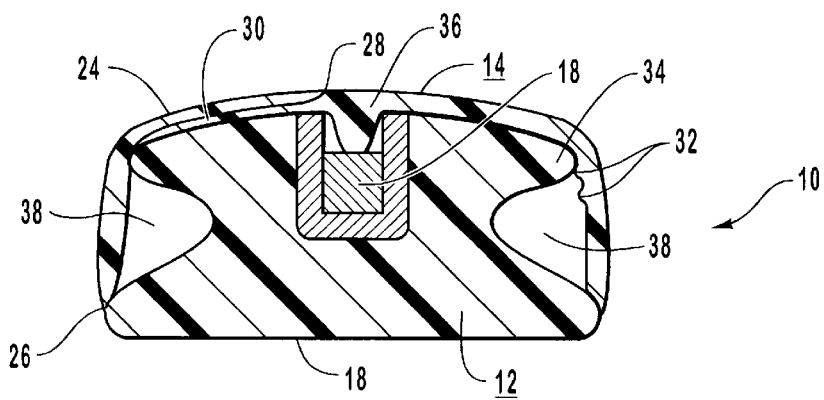
FIG. 1B shows the orthodontic bracket of FIG. 1A with the ligation cover being "closed" or "locked" relative to the arch wire slot.

A first exemplary orthodontic bracket is shown in FIGS. 1A–1B. Orthodontic bracket 10 includes a generally anvil-shaped bracket base 12 and a ligation cover 14 connected thereto. The bracket base 12 includes an arch wire slot 16 for receiving an arch wire 18 therein. Although shown as having a square cross section, the arch wire 18 can have any desired cross section, such as rectangular, circular, oval, and combinations thereof (e.g., part angular and part curved). The arch wire slot 16 can have any desired configuration. Because arch wires are typically made of metal, and in the case where the bracket base 12 is made of plastic, as depicted in FIGS. 1A and 1B, it may be advantageous to include a reinforcement insert 20 that is made of metal, ceramic, or a more durable plastic in order for the bracket base to have greater durability and resistance to wear where it comes into contact with an arch wire. In an exemplary molding process, the plastic base 12 may be molded around a metallic or ceramic reinforcement insert, such as insert 20. Bracket base 12 further includes auxiliary recesses 38 on either side, which can be used to optionally secure the arch wire 18 within the slot 16 using conventional wire or elastomeric ligatures, such as where the ligation cover 14 has been permanently removed or separated from the bracket base 12 (e.g., by severing or tearing). Thus, when the ligation cover 14 is removed, the base 12 may at least approximately resemble a conventional bracket.

The ligation cover 14 is shown as being generally L-shaped so as to hingedly connect to the bracket base 12 at one end of the "L" (by hinge element 22 discussed below), and overlap and lock around the base 12 at the other end. A plurality of locking notches 32 within a latch member 31 assist in locking the ligation cover 14 over a protrusion 34 within the bracket base 12. The notches 32 provide a plurality of locking positions, or degrees of closure, of the ligation cover 14 in order to provide the orthodontic practitioner with the ability to apply varying levels of force onto the arch wire 18. A bearing or holding cam 36 extends downwardly from the ligation cover 14 and partially into the arch wire slot 16 when the cover 14 is in a closed or locked position (FIG. 1B) in order to apply direct pressure to the arch wire 18 and thereby provide active ligation.

In the case where the plastic ligation cover 14 depicted in FIGS. 1A and 1B has sufficient flexibility and resiliency, the ligation cover 14 will be able to flex upwardly and thereby absorb mechanical energy within an arch wire 18 that is not entirely seated within the arch wire slot 16, such as where the tooth (not shown) to which the orthodontic bracket 10 is attached is misaligned in a lingual direction. In this manner, the ligation cover 14 is able to provide continuous active ligation even as an arch wire that is initially not seated within the slot 16 becomes seated as the base 12 moves outward during realignment of the tooth. Moreover, the arch wire energy absorbed by the ligation cover 18 is continuously released and transferred through the base 12 to the tooth as the tooth moves into proper alignment. Thus, the flexation and subsequent release of mechanical energy by the ligation cover 18, coupled with continuous active ligation of the arch wire 18 by the bracket 10, advantageously results in dynamic active ligation of the arch wire over a wide range of tooth positions during realignment of the tooth. This, in turn, eliminates the need for, or at least reduces the frequency of, adjustments to the orthodontic bracket 10 over the course of tooth realignment.

The orthodontic bracket 10 as shown in FIGS. 1A and 1B includes a hinge element 22 that integrally connects the ligation cover 14 to the bracket base 12 and comprises the same material. In this way, the ligation cover 14 and bracket base 12 can be molded, such as by injection molding, in a single molding step to yield an integral, one-piece orthodontic bracket 10. In a preferred embodiment, the integral hinge 22 comprises an area or region of locally reduced cross-sectional thickness in order to provide increased flexibility in the hinge region. Such a hinge may be referred to as a "film hinge". In this way, the film hinge 22 provides a center point or line of rotation about which the ligation cover 14 can be rotated back and forth between an open position, in which the arch wire slot 16 is completely open (FIG. 1A), and a closed or locked position, in which the arch wire slot 16 is completely enclosed in order to provide ligation of an arch wire disposed therein (FIG. 1B).

Interconnecting the ligation cover 14 and the base 12 is a spring element 24. The spring element 24 is also depicted as comprising the same material as ligation cover 14 and bracket base 12 such that the entire bracket 10 can be molded as a single piece. The spring element 24 is connected to the base by hinge element 26 and to the ligation cover 14 by hinge element 28. Hinge elements 26 and 28 are also depicted as comprising film hinges of reduced cross-sectional thickness. Nevertheless, as will be shown in later embodiments, the spring element 24 may be attached to the cover 14 and base 12 using any desired hinge or other connection means known in the art. In order for the spring 24 to lay substantially flush with the ligation cover 14 when the cover is in a closed and locked position, the cover 14 may include a region 30 of reduced cross section into which the spring 24 can insert itself during closure of the ligation cover 14. In this way, the ligation cover 14 and spring 24 yield a smooth, continuous and uniform upper surface when closed. This, in turn, reduces the tendency of food, plaque or other debris to become lodged in the orthodontic bracket 10 while in use. It also yield a bracket having a minimum of uncomfortable jagged edges compared to conventional brackets.

Spring element 24 acts to urge the ligation cover 14 to remain open while in the open position depicted in FIG. 1A, and to remain closed while in the closed position depicted in FIG. 1B. The dynamics of how spring element 24 accomplishes this is more particularly illustrated in FIG. 1A. As shown therein, the point where the spring 24 interconnects with the ligation cover 14 (i.e. at hinge element 28) moves along a circular arc $A_1$, which is defined by a radius $R_1$ having its origin at hinge element 22, as the cover 14 is selectively moved between an open and closed position. On the other hand, were it not for the connection at hinge element 28 between the spring element 24 and the ligation cover 14, a hypothetical free end of spring element 24 would instead move along theoretical arc $A_2$, which is defined by a radius $R_2$ having its origin at hinge element 26 interconnecting the spring 24 and the bracket base 12. Thus, due to the connection between spring 24 and cover 14 at hinge 28, the end of the spring 24 distal to hinge 26 is forced to travel beyond arc $A_2$ and along arc $A_1$, thereby elastically deforming the spring 24 as the cover 14 is moved between the open and closed position.

The maximum extension of spring element 24 is shown as distance X, which is the maximum distance between arcs $A_1$ and $A_2$. Hence, force is required to move the cover 14 in either direction toward the location of distance X. Conversely, the spring 24 will contract and thereby urge the cover 14 away in either direction from the location of distance X. Accordingly, whether the spring 24 will urge the cover 14 either into an open position or a closed position depends on where hinge 28 is located relative to the location of distance X. Although distance X is depicted as being located approximately midway between the open and closed positions of ligation cover 14, one of ordinary skill in the art will appreciate that the orthodontic bracket can be designed so as to position distance X at any desired location depending on how one wishes the spring 24 to behave.

Figure 2:
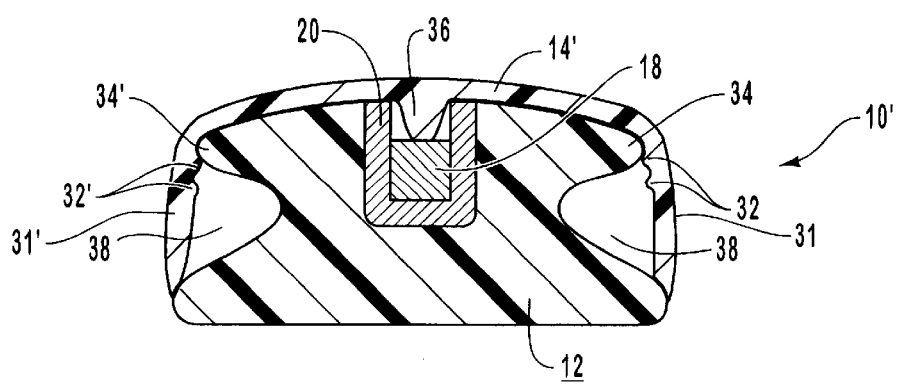
FIG. 2 is a cross-section view of a two-piece orthodontic bracket in which the ligation cover is separate from the bracket base.

FIG. 2 depicts an orthodontic bracket 10' that is similar to the one depicted in FIGS. 1A and 1B, except that it is a two-piece bracket, i.e., the ligation cover 14' is not integrally connected to the base 12. The ligation cover 14' is similar to cover 14, except that it includes a mirror image of the latch member 31 at the opposite end (i.e., latch member 31') rather than the hinge and spring arrangement found in cover 14 opposite latch member 31. The additional locking notches 32' within second latch member 31' are able to lock over a second protrusion 34' within bracket base 12 in the same way notches 32 lock over protrusion 34. In most other respects, ligation cover 14' is virtually identical to ligation cover 14. The orthodontic bracket 10' may simply be provided as a two-piece assembly, or it may result by first removing the integral ligation cover 14 depicted in FIGS. 1A and 1B, such as by using a scalpel, and then replacing it with the removable ligation cover 14' depicted in FIG. 2. Such a procedure may be necessary in cases where it is difficult for the ligation cover 14 to flip open, in order to adequately expose the arch wire slot 16 such as due to a cramped tooth position. A kit may be provided comprising the integral, one-piece orthodontic bracket 10 and an auxiliary ligation cover 14' that may be optionally used to ligate an arch wire in the event it becomes necessary to remove ligation cover 14.

Figure 3A:
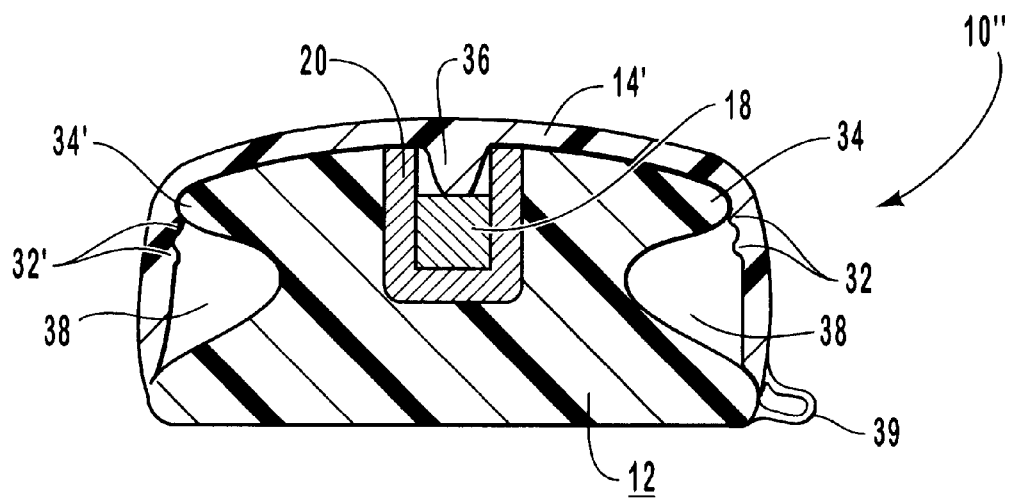
FIGS. 3A and 3B depict a variation of the orthodontic bracket of FIG. 2 in which the ligation cover is loosely connected to the bracket base by a leash.
Figure 3B:
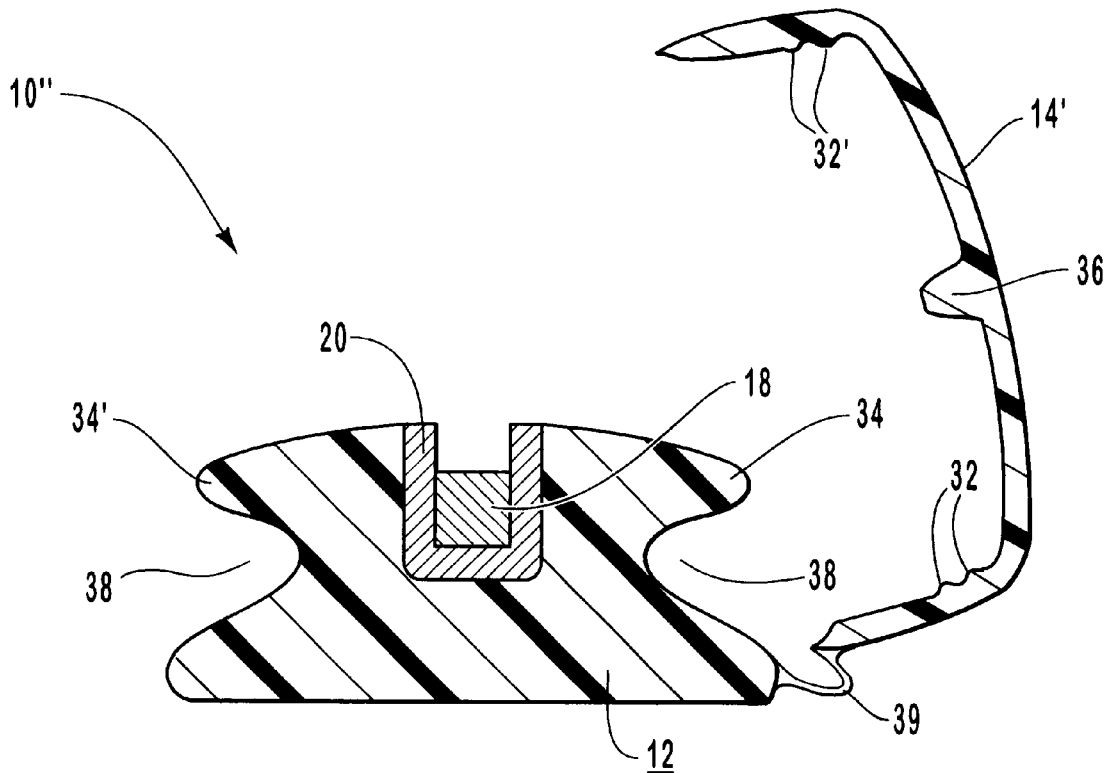

FIGS. 3A–3B depict a variation of the orthodontic bracket 10' depicted in FIG. 2, with the main difference being that the orthodontic bracket 10" depicted in FIGS. 3A and 3B includes a flexible leash member 39 interconnecting the bracket base 12 and ligation cover 14'. The main purpose of the leash member 39 is to prevent a practitioner from inadvertently misplacing the ligation cover 14', or worse, accidentally dropping it down the patient's throat during ligation or adjustment. For example, the assembled bracket 10" can be first attached to a tooth (not shown), followed by detachment of the ligation cover 14', placement of an arch wire 18 within the arch wire slot 16, and reattachment of cover 14', while reducing or eliminating the threat of a detached ligation cover 14' being misplaced, dropped or allowed to fall down the patient's throat.

Figure 4A:
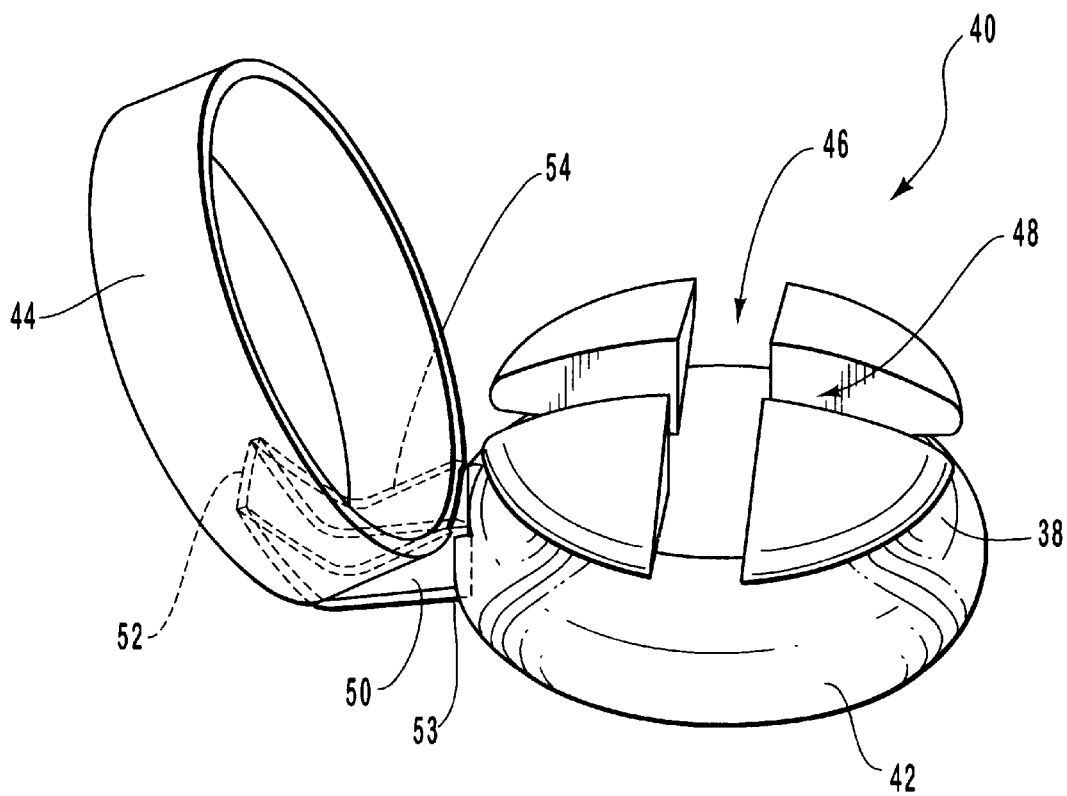
FIG. 4A is a perspective view of a hinged orthodontic bracket that includes a ligation cover configured so as to substantially encase or surround the bracket base when in a closed or locked position.
Figure 4B:
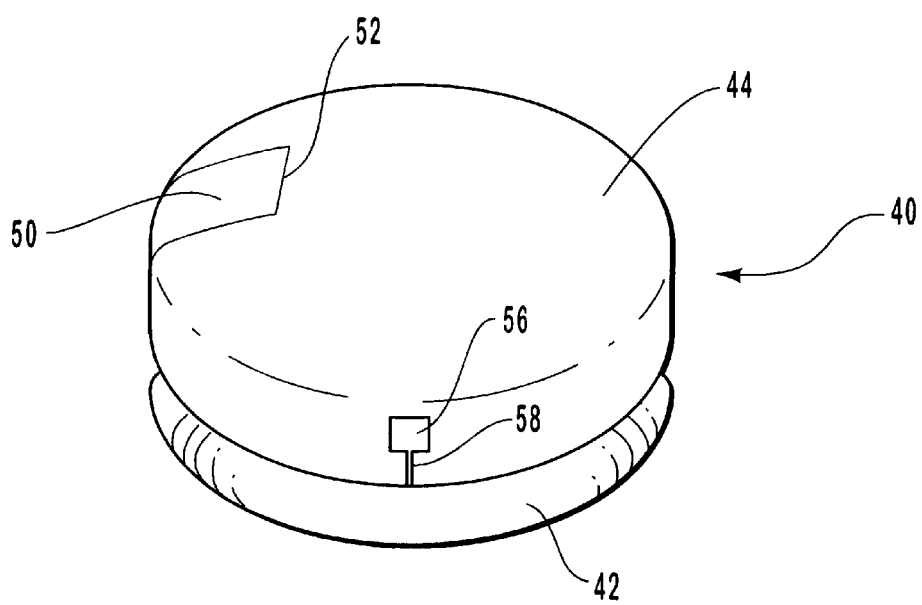
FIG. 4B shows the orthodontic bracket of FIG. 4A with the ligation cover being "closed" or "locked" relative to the arch wire slot.

An alternative embodiment of a hinged orthodontic bracket is depicted in FIGS. 4 and 5. Orthodontic bracket 40 includes a bracket base 42 and a ligation cover 44 attached to the base by a joint element 50. The base 42 includes an arch wire slot 46 and an auxiliary slot 48 oriented transversely to slot 46. Auxiliary slot 48 may be used in the conventional manner to assist in fixing an arch wire within the arch wire slot 46, such as by means of wire or elastomeric ligatures. The ligation cover 44 is formed in a hood-like manner and is integrally connected to the joint element 50 by means of an integral hinge 52, which is advantageously a film hinge. The joint element 50 is similar in design to the spring element 24 of the embodiment in accordance with FIGS. 1A and 1B, except that joint element 50 does not act as a spring, but merely as a connection between cover 44 and base 42. This is because the ligation cover 44 is not separately attached to the base 42 by any means other than the joint element 50. A recess 54 is advantageously provided in the outside of the cover 44 so that the joint element 50 and the cover 44 can nest together and form a single, smooth outer surface upon closing or locking the cover 44 with the base 42.

The base 42, ligation cover 44, and joint part 50 can either be integrally molded in a single step, so as to yield an integral, one-piece orthodontic bracket, or else an end of the joint part 50 opposite the integral hinge 52 may initially be detached from the base 42 and thereafter attached to the base 42, e.g., by pushing the end of joint part 50 into a corresponding groove within the base 42 in a form-locking manner. In this way, the ligation cover 44 and joint part 50 are insertably affixed to the base 42. In either embodiment, a further integral hinge 53, such as a film hinge, may be provided in the region of attachment between the joint part 50 and the base 42 so that the joint part 50, and thus also the ligation cover 44, can be pivoted about the hinge 53 in order to facilitate rotation of the cover 44 over and onto the base 42 during ligation.

Peripheral locking notches (not shown) may be provided on an inner surface of the ligation cover 44 to assist in locking or clipping the cover 44 onto the base 42. An exit aperture 56 (FIG. 4B) is provided on each side of the ligation cover 44 to allow complete closure of the ligation cover 44 around an arch wire (not shown) placed within the arch wire slot 46. An insertion slot 58 extending from the exit aperture 56 to a lower edge of the ligation cover 44 permits the passage of the arch wire into and out of each exit aperture 56 during opening and closing of the cover 44.

FIGS. 5–8 depict orthodontic brackets that are similar to the brackets depicted in FIGS. 1–2, except that the brackets of FIGS. 5–8 further include a bearing spring extending from the ligation cover and partially into the arch wire slot when the ligation cover is in a locked position so as to provide an alternative, or additional, means for providing dynamic active ligation of the arch wire as the tooth moves over time into proper alignment. Some embodiments further include under cuts or recesses within an underside of the base to assist in adhering the bracket to a tooth. One of ordinary skill will readily appreciate, however, that the underside of the bracket base could alternatively be textured or roughened to promote better adhesion to the tooth.

Figure 5A:
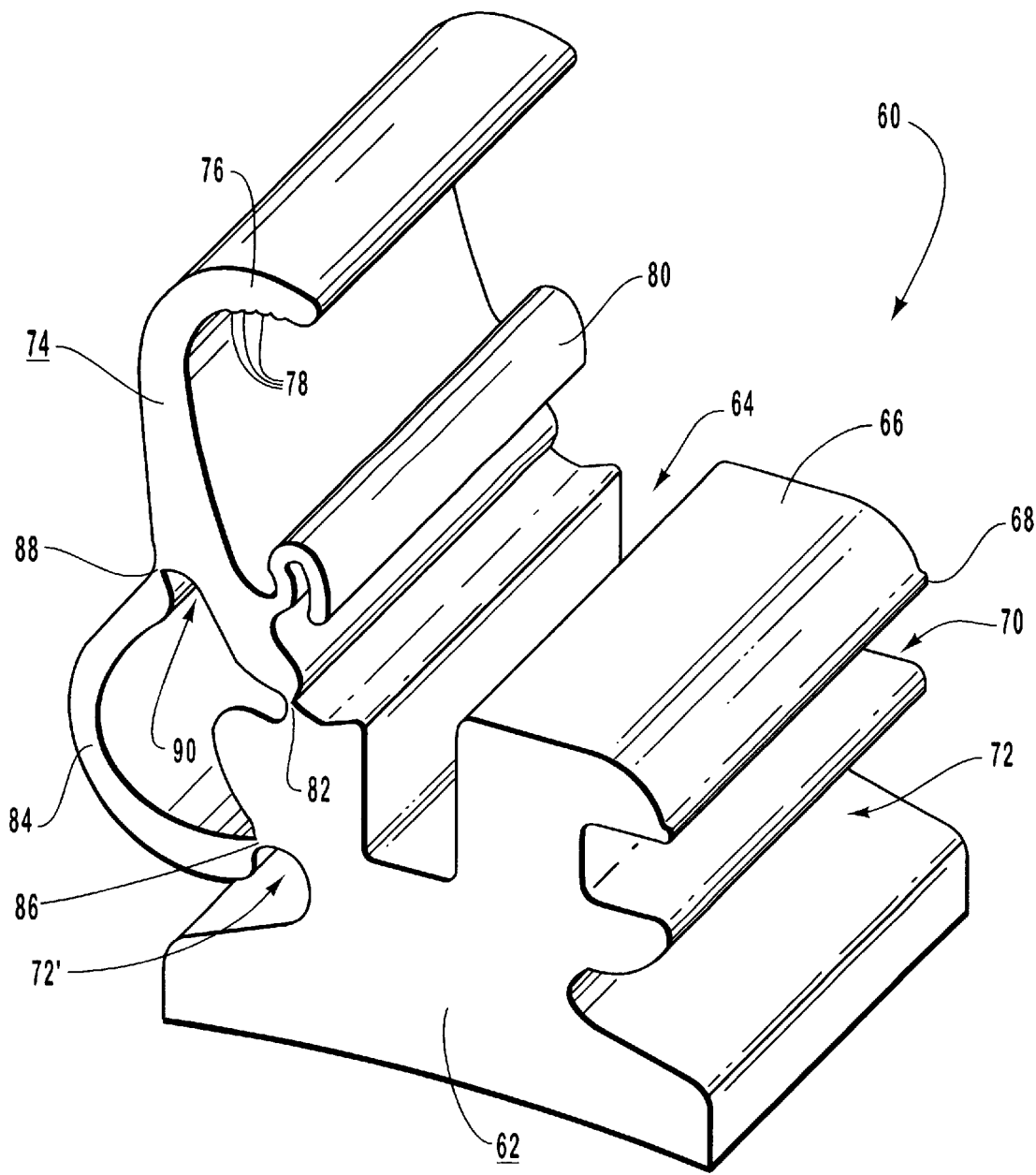
FIG. 5A is a perspective view of a hinged, one-piece orthodontic bracket that includes a leaf spring extending from an under side of the ligation cover and configured to engage an arch wire associated with the bracket base.
Figure 5B:
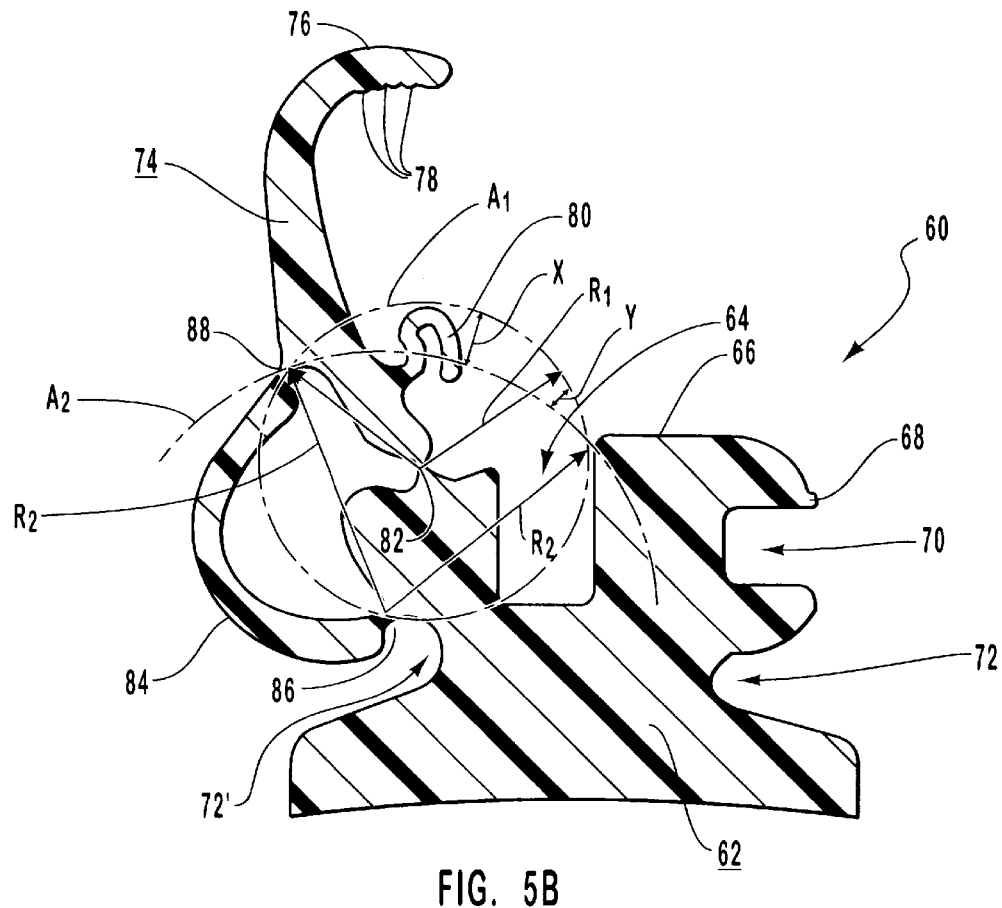
FIGS. 5B and 5C are cross-section views of the orthodontic bracket of FIG. 5A showing the kinematics of a spring element interconnecting the ligation cover and bracket base.
Figure 5C:
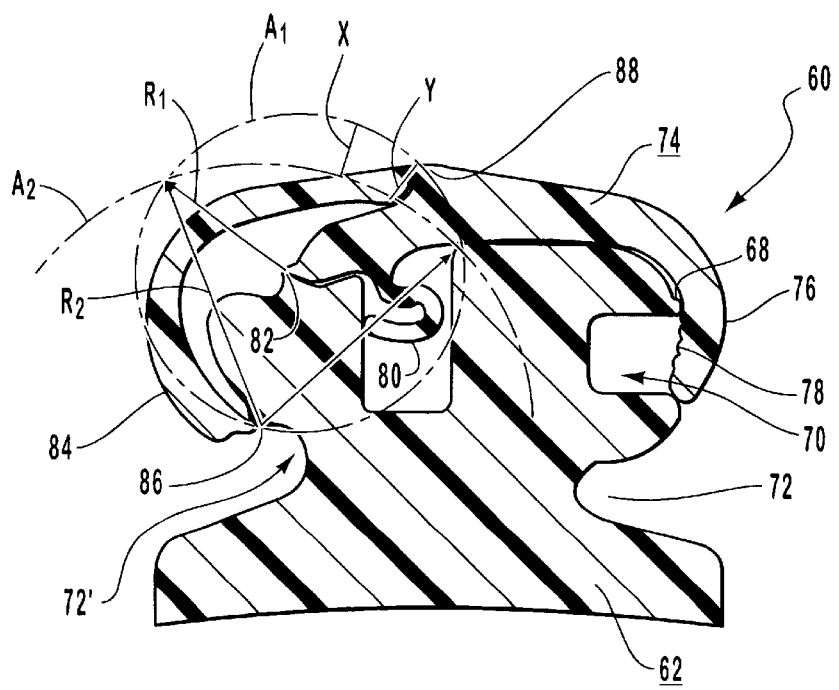

FIGS. 5A–5C depict an orthodontic bracket 60 manufactured as a single piece from, e.g., a plastic material (e.g., by injection molding). Orthodontic bracket 60 includes a bracket base 62 shaped approximately like an anvil in cross section and a ligation cover 74 integrally attached to the base 62 in an articulated manner. The bracket base 62 includes a main arch wire slot 64 that opens upward for receipt of an arch wire (not shown) therein. As in the embodiment depicted in FIGS. 1–2, the bracket base 62 may optionally include a reinforcement insert (not shown) to provide greater durability and wear resistance. Any appropriate arch wire may be inserted into slot 64 and ligated using the cover 74.

The bracket base 62 further includes an upper end 66 next to the arch wire slot 64, with a locking protrusion or edge 68 formed in a side of the upper end 66 distal to the arch wire slot 64. The locking protrusion 68 is used to engage locking notches 78 formed with a curved latch element 76 within ligation cover 74. Below edge 68 is an auxiliary arch wire slot 70 that may be used to hold therein an auxiliary arch wire (not shown). The arch wires within both of slots 64 and 70 can by ligated at the same time by the single action of simply closing or locking the ligation cover 74 over the bracket base 62. Further down, the bracket base 62 includes a secondary recess 72, and a corresponding recess 72' on the other side, which can be used, if desired, to secure conventional ligatures to the base 62.

The ligation cover 74 forms a protective hood so as to substantially cover the upper surface of the bracket base 62 and arch wire slot 64 when in a locked position. The ligation cover 74 is approximately kidney-shaped in cross section and is connected in one piece to the base 62 by means of a first integral hinge 82, e.g., a film hinge. A spring element 84, similar to the spring element 24 depicted in FIGS. 1–2, but curved approximately like an arc in cross section, is integrally attached at one end to the bracket base 62 in an articulated manner by means of a first joint 86 and at another end to the ligation cover 74 by means of a second joint 88, both of which can be film hinges, i.e., areas of locally reduced cross-sectional thickness.

As more particularly shown in FIG. 5C, the spring element 84 is designed and oriented so as to interact with the ligation cover 74 to yield a substantially smooth and uniform outer surface when the cover 74 is in a locked position relative to the bracket base 62. Together, the cover 74 and spring 84 form a hood-like, kidney-shaped protective shell over the base 62. To facilitate nesting of the spring element 84 into the ligation cover 74, a depression 90 (FIG. 1) is provided in an upper side of the cover 74. The locking notches 78 provide for varying locked positions of the ligation cover 74 relative to the base 62 in order to apply varying levels of pressure to the arch wire.

A leaf spring 80 extends from an inner surface of the cover 74 and is positioned so as to partially extend into the arch wire slot 64 when the cover 74 is in a locked or closed position relative to the base 62. The leaf spring 80 is an example of a bearing spring. The purpose of the leaf spring 80 is to provide downward pressure onto an arch wire positioned within arch wire slot 64. Because the leaf spring 80 is able to compress or extend, depending on how completely the arch wire (not shown) is seated within the arch wire slot 64, the bearing spring 80 comprises means for providing dynamic active ligation of an arch wire over time as the tooth to which the orthodontic bracket 60 is attached is moved into proper alignment. The bearing spring 80, either alone or in combination with a flexible ligation cover, is able to absorb alignment energy from an arch wire initially bearing upward toward the bearing spring 80 and then incrementally release this energy over time as the arch wire becomes more completely seated within the arch wire slot 64, to thereby provide dynamic active ligation of the arch wire (see FIGS. 12A and 12B). The pressure exerted by the bearing spring 80 onto the arch wire can be adjusted by raising or lowering the ligation cover 74 relative to the base 62 by altering which of the locking notches 78 within the latch 76 engages the locking edge 68.

The base 62, cover 74, spring element 84, and bearing spring 80 can be integrally molded as a single piece by injection molding an appropriate plastic material. In the alternative, the various pieces can be separately molded and then joined together using heat, cement or other mechanical fixation means known in the art. The joint 86 between the spring element 84 and base 62 is preferably located approximately halfway up the base 62, between its bottom and its upper side, while the joint 88 between the spring 84 and ligation cover 74 is attached to the cover 74 so as to sit directly above the arch wire slot 64 when the ligation cover 74 is closed (FIG. 5C). Each of the film hinges 82, 86 and 88 advantageously extend across the entire width of the bracket base 62 for maximum durability. The bearing spring 80 may also extend across the entire width of the base 62, or any portion thereof depending on the desired stiffness.

Figure 6A:
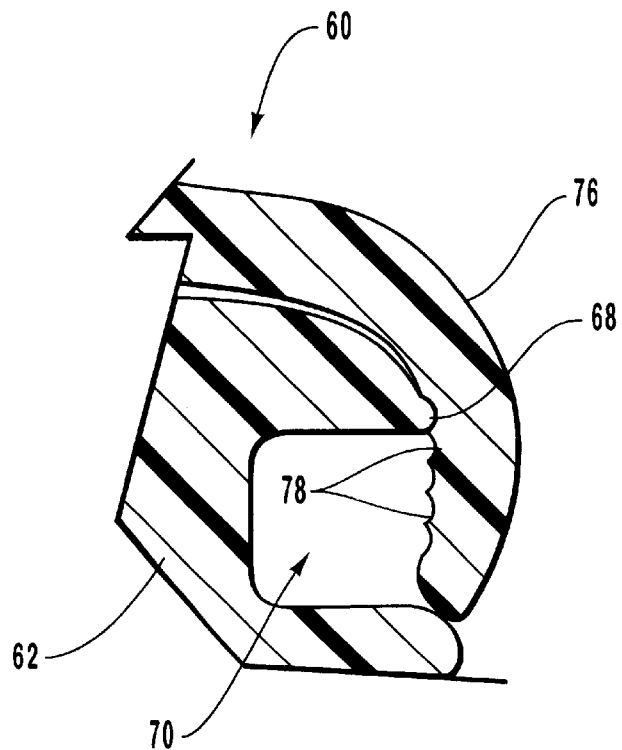
FIGS. 6A and 6B are cross-section, close-up views of different locking notches for locking a ligation cover to a bracket base.
Figure 6B:
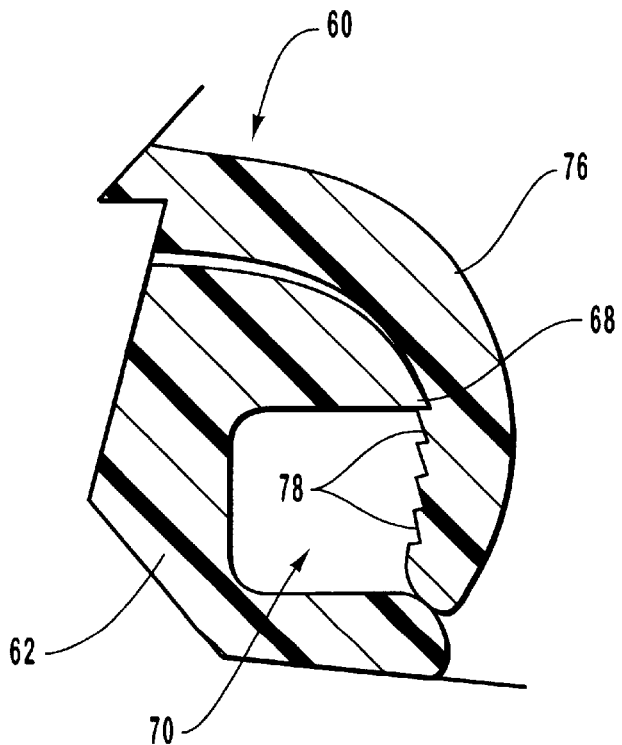

As more clearly shown in FIG. 6A, the locking notches 78 may be shaped so as to form curved depressions therebetween, or they may be more serrated or sharp-edged as shown in FIG. 6B. The shape of the locking notches 78 will typically depend on the shape of the corresponding locking edge 68 within the upper side 66 of the base 62.

Spring element 84 operates to urge the ligation cover 74 to remain open while in an open position, and to remain closed while in a closed position. As more particularly shown in FIGS. 5B and 5C, if the spring 84 were not attached to the ligation cover 74 by hinge 88, a resulting hypothetical free end of spring 84 would rotate about the hinge 86 interconnecting the spring 84 and the bracket base 62 and travel along a hypothetical arc $A_2$, which is defined by a radius $R_2$ having its origin at said hinge 86. However, because the spring 84 is also affixed to the ligation cover 74 by hinge 88, the end of the spring 84 attached to the cover 74 at hinge 88 is instead forced to travel along an arc $A_1$, which is defined by a radius $R_1$ having its origin at hinge 82 interconnecting the ligation cover 84 and the bracket base 62. In this way, the spring element 84 operates much the same way as the spring element 24 depicted in FIGS. 1A and 1B, because it is elastically distorted as the ligation cover 74 is rotated between the open and closed positions. What is different is that spring element 84 is able to continue urging the ligation cover 74 to remain closed with significant downward force even when the ligation cover 74 is rotated into the closed, or locked, position. In this way, the ligation cover 74 is able to provide continuous ligation pressure even when the locking notches 78 are disengaged from the locking edge 68.

The spring element 84 is able to exert a significant closing force upon the ligation cover 74 even when closed because the spring element 84 remains partially tensioned, or elastically elongated, even after rotating the cover 74 into the closed position. As shown in FIG. 5B, the transition between where the spring 84 urges the cover 74 to move toward either an open or closed position is in the region of distance X, which is the maximum offsetting distance between arcs $A_1$ and $A_2$. As a result of the relative locations of the points of origin of radii $R_1$ and $R_2$, the spring 84 does not completely relax as the ligation cover 74 is rotated into a closed position, but remains elongated by a distance Y between arcs $A_1$ and $A_2$. Due to the above-mentioned kinematics, the spring force exerted by spring element 84 does not go to zero when the ligation cover 74 is closed, but is rather reduced by about 70% relative to the maximum spring force in the region of distance X. Accordingly, the bearing spring 80, in combination with the continuous force exerted by the spring element 84, is able to provide active ligation of an arch wire disposed within the arch wire slot 64 even when the locking notches 78 do not engage the locking protrusion 68.

The ligation cover 74 is also able to provide passive ligation of a second arch wire disposed within auxiliary arch wire slot 70, which is parallel to slot 64 but which opens laterally away from the main arch wire slot 64 and out a side of the bracket base 62. As a result of the closing force provided by the spring element 84, the ligation cover 74 provides secure and reliable passive ligation of an arch wire located within auxiliary arch wire slot 70, even when the locking notches 78 do not engage the locking protrusion 68. Moreover, the forces exerted by a second arch wire within auxiliary slot 70 would not include a force vector of sufficient force to overcome the force of the spring element 84 that urges the cover 74 to remain closed. In this way, the spring element 84 is able to provide an important safety feature in the event that the ligation cover 74 is inadvertently unlocked, such as by upward pressure by the main arch wire located within the main arch wire slot 64.

Figure 7A:
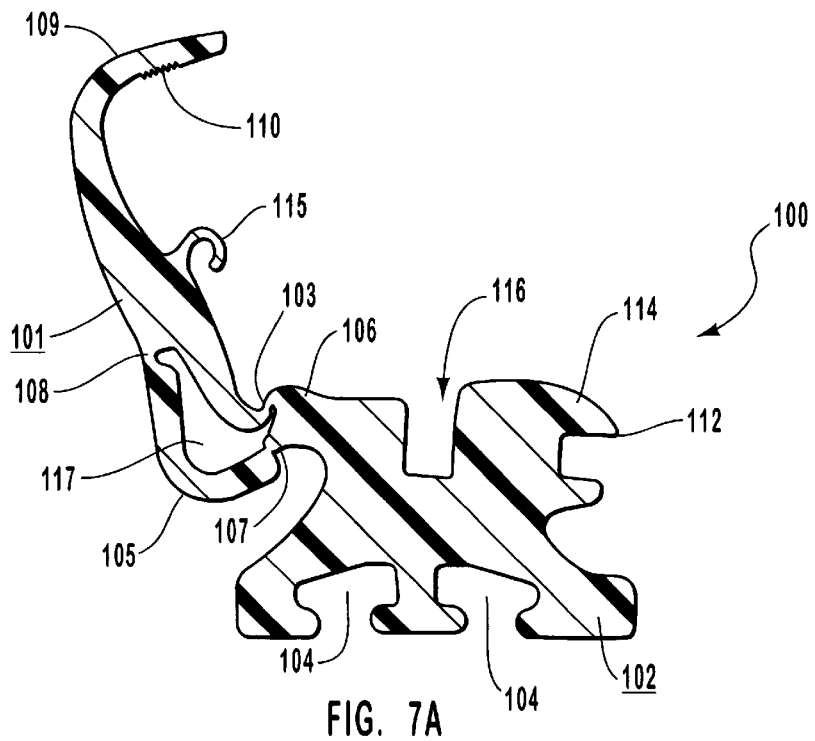
FIGS. 7A–7C is a cross-section view of a hinged orthodontic bracket that includes a ligation cover, a bracket base, a spring element interconnecting the cover and base, a bearing spring for engaging an arch wire, and channels or under cuts for enhanced adhesion to a tooth.
Figures 7B, 7C:
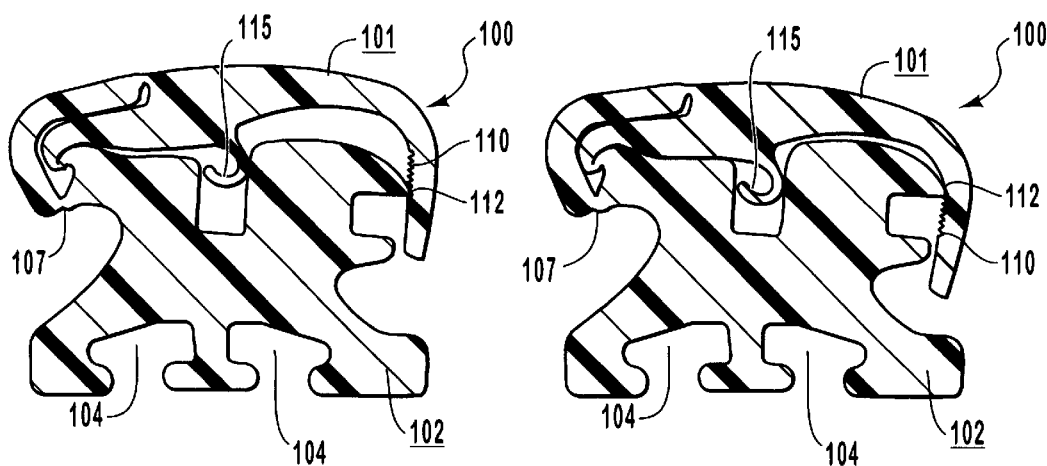

FIGS. 7A–7C depict an embodiment of an orthodontic bracket 100 that is substantially similar to the orthodontic bracket 60 depicted in FIGS. 5A–5C, except that orthodontic bracket 100 further includes under cuts within the bottom surface of the bracket base to enhance the ability of the orthodontic bracket to adhere to a tooth. This assists, for example, in those cases where the plastic used to manufacture the orthodontic bracket 100 is a non-stick material that resists adhesion by foreign materials.

As more particularly shown in FIG. 7A, the orthodontic bracket 100 includes a bracket base 102 into which a pair of parallel under cuts 104 have been formed. The under cuts 104 are inwardly enlarged so as to have a wider cross-section within the interior of base 102 then where they open at the bottom of the base 102. In this way, the cement or adhesive entering under cuts 104 can mechanically interlock with the bracket base 102 upon hardening. In this way, an adhesive will still be able to secure the orthodontic bracket 100 to the tooth even if the adhesive is unable to form a strong chemical or adhesive bond with the plastic used to form the orthodontic bracket 100. In all other respects, the orthodontic bracket 100 is substantially similar to the orthodontic bracket 60 depicted in FIGS. 5A–5C.

The orthodontic bracket 100 includes a ligation cover 101 that is integrally attached to an upper end 106 of the bracket base 102 by means of an integral hinge 103 (e.g., a film hinge). A spring element 105 interconnects the ligation cover 101 with the bracket base 102 in order to urge the ligation cover 101 to remain open while in an open position, and to remain closed while in a closed position. The spring element 105 is attached at one end to the bracket base 102 by a base hinge 107 and at an opposite end to the ligation cover 101 by a cover hinge 108, both of which may comprise film hinges. The kinematics of the forces between the spring element 105 and the ligation cover 101 are substantially similar to those described above with respect to orthodontic bracket 60. The ligation cover 101 further includes a curved latch element 109 that further includes locking notches 110 designed to interact with a protruding edge 112 of an upper end 114 of the bracket base 102. A bearing leaf spring 115 extends from an inner surface of the ligation cover 101 into an arch wire slot 116 within the bracket base 102 while the ligation cover 101 is in a closed or locked position. One notable difference between orthodontic bracket 100 and orthodontic bracket 60 is that the space 117 between the spring element 105 and the ligation cover 101 in orthodontic bracket 100 is smaller than the corresponding space in orthodontic bracket 60 such that upon closing the ligation cover 101, the space 117 is almost entirely eliminated as the spring 105 is brought toward the surface of the ligation cover 101 (FIGS. 7B–7C). In contrast, a substantial space remains between the spring element 84, base 62 and ligation cover 74 of the orthodontic bracket 60 depicted in FIGS. 5A–5C. As demonstrated in FIGS. 7B and 7C, the locking notches 110 provide for varying degrees of closure of the ligation cover 101 relative to the bracket base 102. This allows an orthodontic practitioner to adjust the level of force exerted by the leaf spring 115 onto an arch wire (not shown) disposed within the arch wire slot 116.

Figure 8:
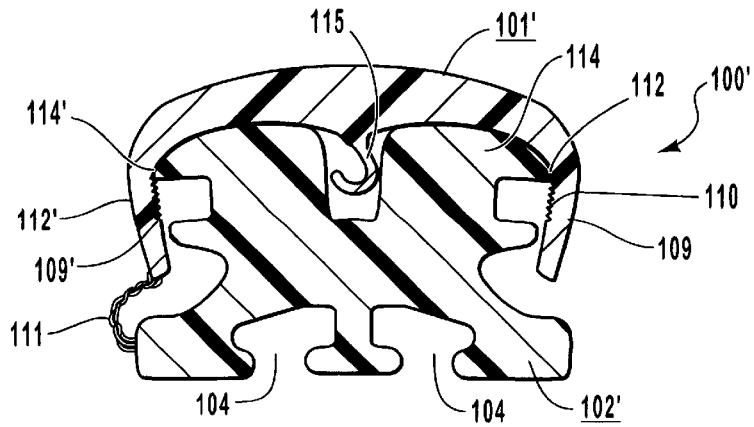
FIG. 8 depicts a variation of the orthodontic bracket of FIGS. 7A–7C, except that the ligation cover is separate and detachable from the bracket base.

FIG. 8 depicts an alternative orthodontic bracket 100' that is substantially identical to orthodontic bracket 100, except that the spring element 105 and the hinge 103 have been eliminated in favor of a curved latch element 109' corresponding to, and comprising the mirror image of, the curved latch element 109 located distal to the spring element 105 of orthodontic bracket 100. In this way, the ligation cover 101' is detachable from bracket base 102' such that a two-piece orthodontic bracket 100' is provided. A flexible leash element 111 interconnecting the base 102' and ligation cover 101' may be provided to prevent the ligation cover 101' from being inadvertently misplaced or dropped down the patient's throat during ligation or adjustment. The curved latch 109' includes locking notches 110', which are able to provide variable locking positions relative to a second protrusion 112' in an upper end 114' opposite to upper end 114.

Figure 9A:
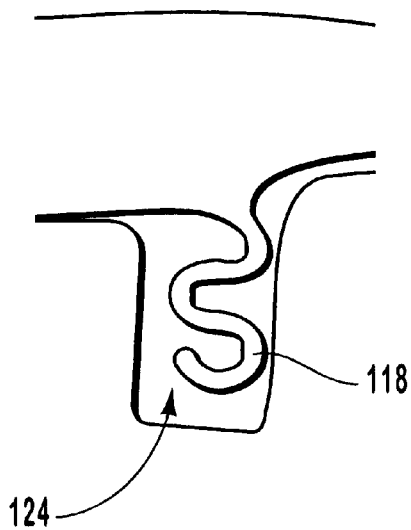
FIG. 9A is close-up view of a serpentine bearing spring extending partially into an arch wire slot.
Figure 9B:
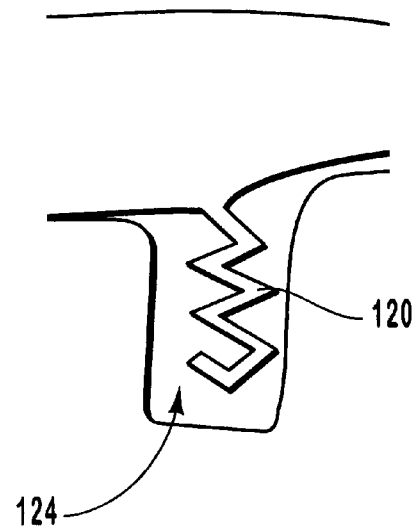
FIG. 9B is close-up view of a zig-zag bearing spring extending partially into an arch wire slot.

FIGS. 9A–9D depict alternative bearing springs that may be employed to provide dynamic active ligation from the ligation cover to an arch wire disposed within an arch wire slot. For example, FIG. 9A depicts a serpentine spring 118 having a plurality (e.g., three) transitions of curvature, rather than the single curvature of the leaf spring 115 shown in FIGS. 7–8. In this way, the serpentine spring 118 will be able to elastically compress and elongate over a greater distance so as to provide a greater range of dynamic active ligation of an arch wire. The zig-zag spring 120 depicted in FIGS. 9B similarly provides a larger range of compression and elongation compared to a simple leaf spring.

Figure 9C:
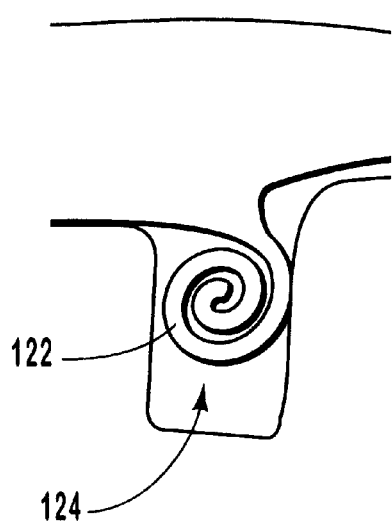
FIG. 9C is close-up view of a coiled bearing spring extending partially into an arch wire slot.
Figure 9D:
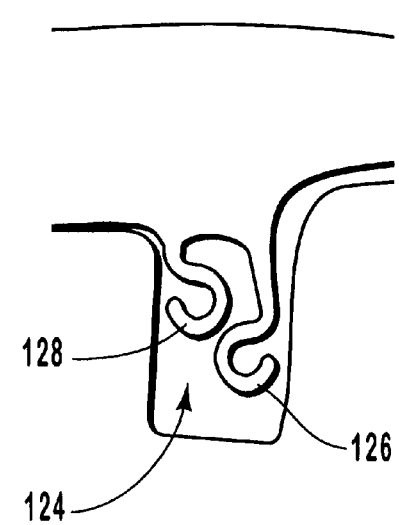
FIG. 9D is close-up view of a dual leaf spring extending partially into an arch wire slot.

The coiled spring 122 depicted in FIG. 9C provides another alternative means for actively ligating an arch wire. The dual leaf spring arrangement 124 depicted in FIG. 9D provides a two-stage bearing effect onto a ligated arch wire. In particular, a longer leaf spring 126 extends more fully into the arch wire slot and will continuously provide a ligating force to an arch wire disposed therein. A shorter leaf spring 128 may provide additional ligation pressure onto an arch wire that is less fully seated within the arch wire slot, depending on how far the arch wire is from being fully seated. In this way, greater ligation pressure can be applied to an arch wire that is less fully seated, such as where the orthodontic bracket is attached to a tooth that is particularly misaligned. In this way, the dual leaf spring 124 is able to exert significantly greater alignment pressure onto a more poorly aligned tooth, and then relax as the tooth becomes partially realigned.

Figure 10A:
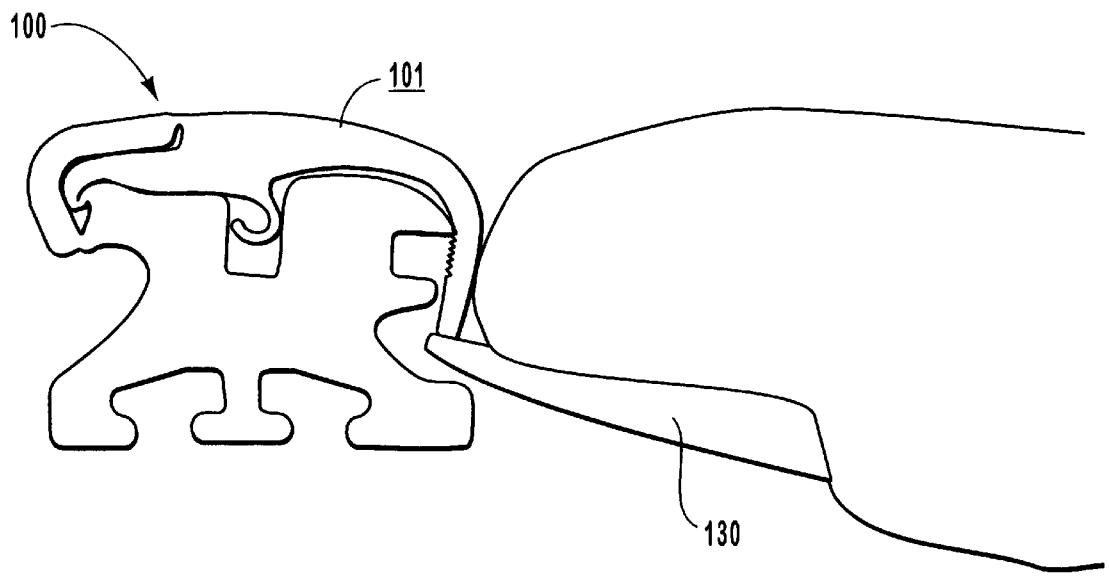
FIG. 10A depicts the orthodontic bracket of FIGS. 7A–7C being opened by a person's fingernail.
Figure 10B:
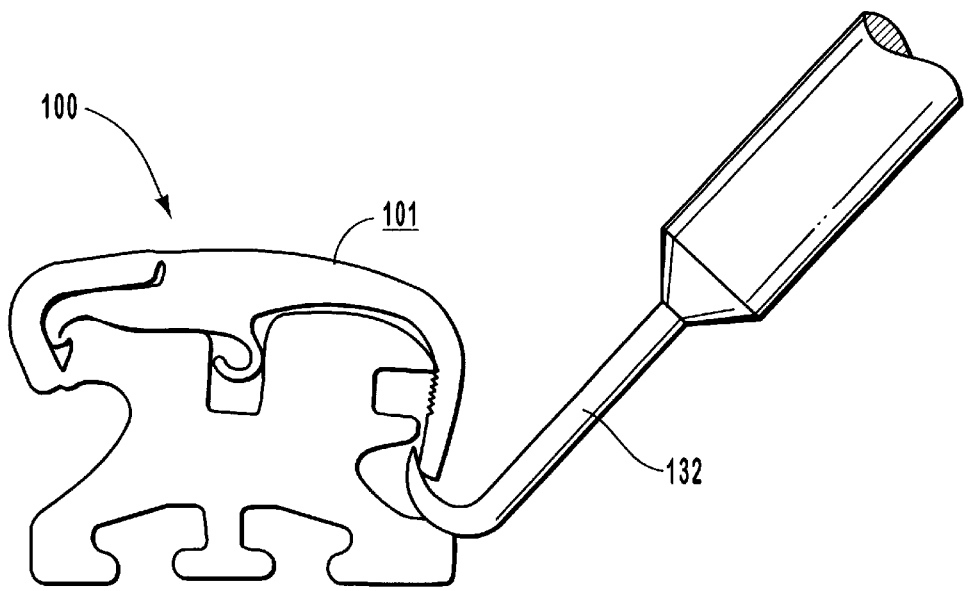
FIG. 10B depicts the orthodontic bracket of FIGS. 7A–7C being opened by a common dental tool.

FIGS. 10A–10B demonstrate the ease with which the orthodontic bracket 100 can be opened and closed without the need for special tools or complicated techniques. As shown in FIG. 10A, the ligation cover 101 can easily be opened by means of a person's fingernail 130. FIG. 10B depicts the use of a simple dental tool or pick 132, which is commonly used by all dentists, to open ligation cover 101. It is readily apparent that the cover 101 is easily closed by a person's finger.

Figure 11A:
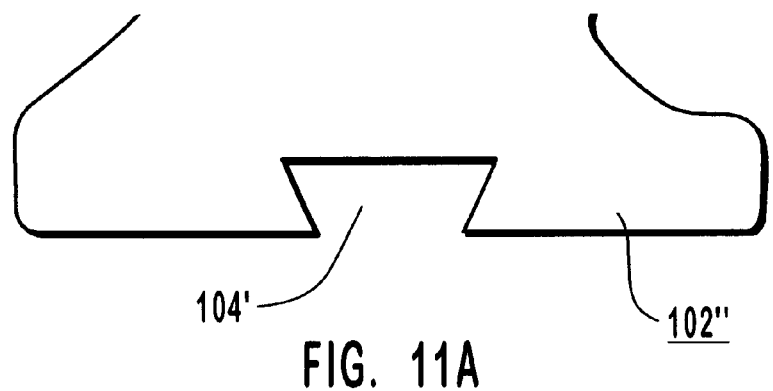
FIGS. 11A–11B depict different numbers of trapezoidal under cuts used in promoting better adhesion between an orthodontic bracket and a tooth.
Figure 11B:
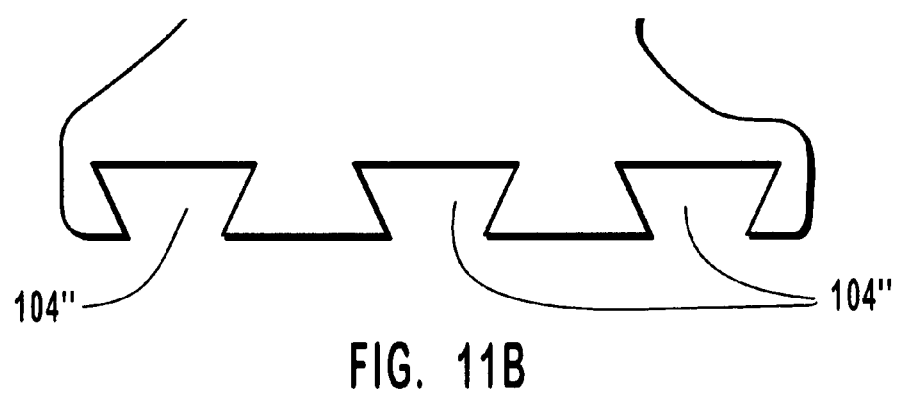

FIGS. 11A–11B depict alternative numbers of under cuts that may be included within a bracket base 102" to promote adhesion to a tooth. FIG. 11A depicts a single trapezoidal under cut 104', while FIG. 11B depicts three parallel trapezoidal under cuts 104". It will be appreciated that the under cuts within an orthodontic bracket base may assume any desired shape or orientation. In general, the greater the number of under cuts, the greater will be the ability for cement or glue to mechanically adhere to the bottom of the orthodontic bracket base. Moreover, all things being equal, under cuts that are tapered such that they become more enlarged toward the interior of the bracket base (see FIGS. 7–8 and 10–11) will provide greater mechanical retention than those which do not have such a taper. Of course, one of ordinary skill will realize that there are any number of design features that could be used to promote adhesion of the orthodontic bracket to a tooth, including a textured or roughened under surface, or any other adhesion promoting designs known in the art.

Figure 12A:
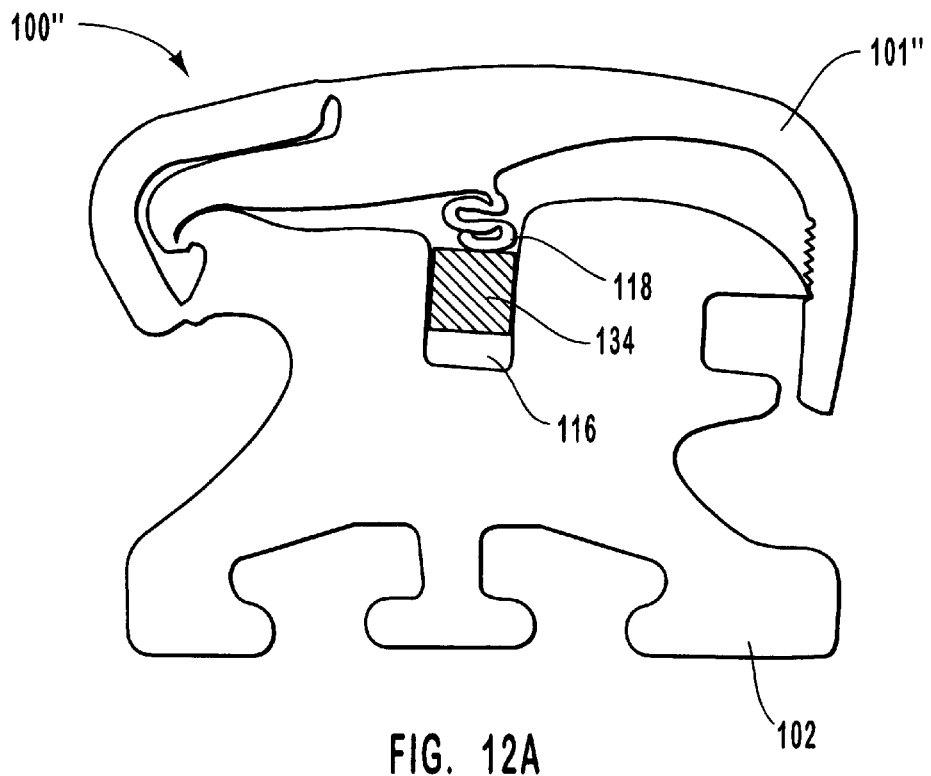
FIGS. 12A–12B depict an orthodontic bracket having a serpentine bearing spring in varying stages of compression due to the orientation of the arch wire relative to the bracket base.
Figure 12B:
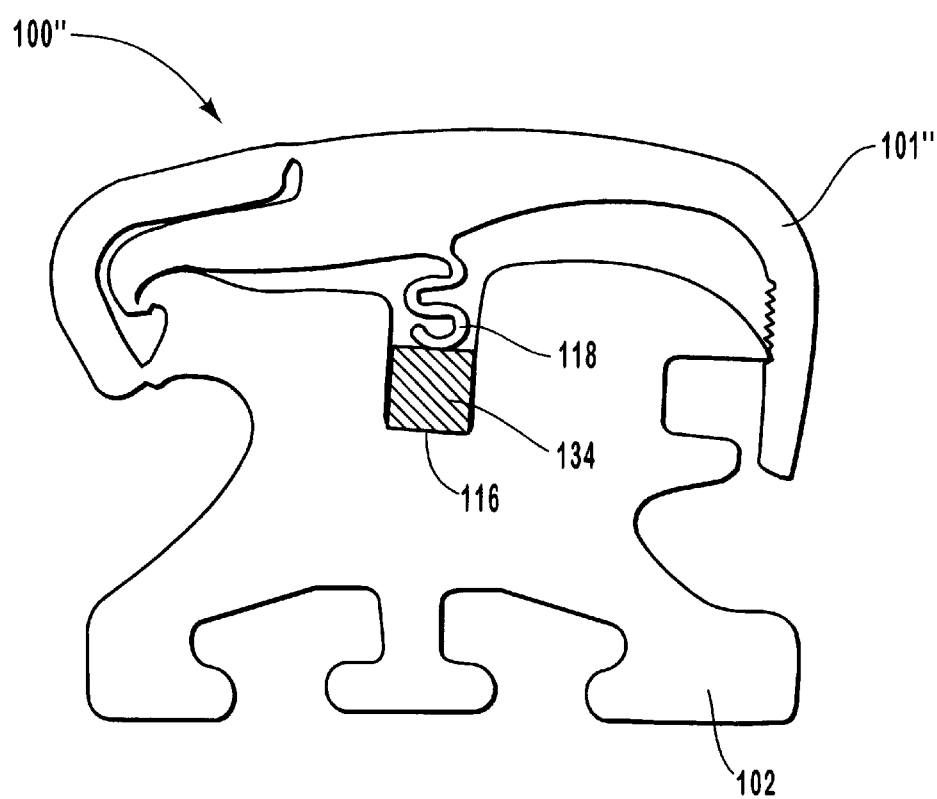

FIGS. 12A–12B demonstrate the concept of dynamic active ligation by an orthodontic bracket 100". In particular, FIG. 12A depicts a serpentine bearing spring 118 disposed on ligation cover 101" in a compressed state and bearing down on an arch wire 134 that is not fully seated within the arch wire slot 116. Over time, as the arch wire 134 becomes more fully seated within the arch wire slot 116 (more precisely, as the tooth and associated orthodontic bracket 100" move toward the arch wire 134), the bearing spring 118 elongates and continues to provide active ligation pressure onto the arch wire 134. In this way, the bearing spring 118 is able to provide continuous ligation pressure without the need to readjust the position or tightness of the ligation cover 101" relative to the base 102. The bearing spring 118 is able to initially absorb mechanical energy that is transferred from the impartially seated arch wire 134 depicted in FIGS. 12A. This mechanical energy is transferred, albeit in a dampened state, to the tooth being realigned so as to urge the tooth into proper alignment. Over time, as the tooth moves into proper alignment, the mechanical energy stored by bearing spring 118 is incrementally released or reduced. The absorption of arch wire energy by bearing spring 118 also provides a dampening effect on the amount of force that would otherwise be exerted by the arch wire 134 onto the tooth being realigned, thus providing greater comfort and less pain to the patient.

Figure 13A:
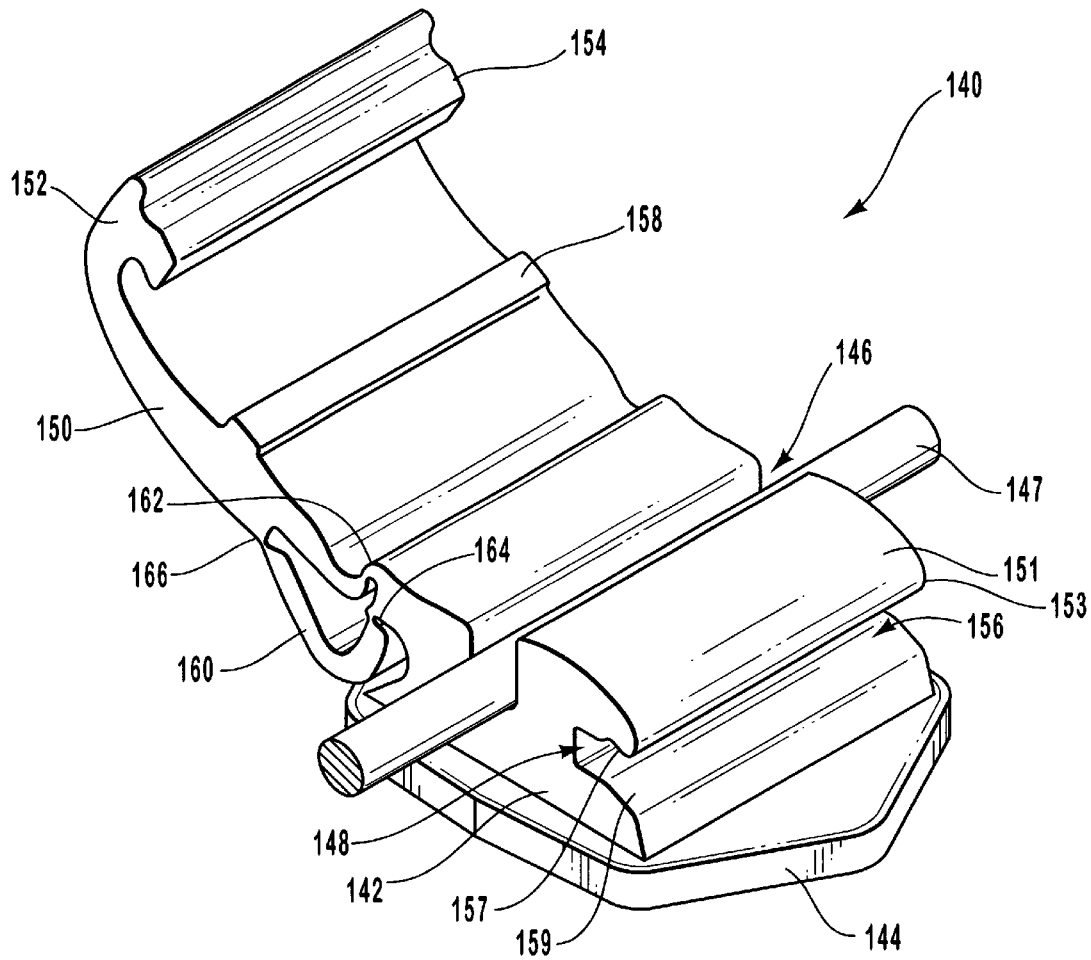
FIG. 13A is a perspective view of an orthodontic bracket that includes a special locking feature that locks the ligation cover more tightly to the bracket base in response to increased upward pressure from an arch wire to the ligation cover.
Figure 13B:
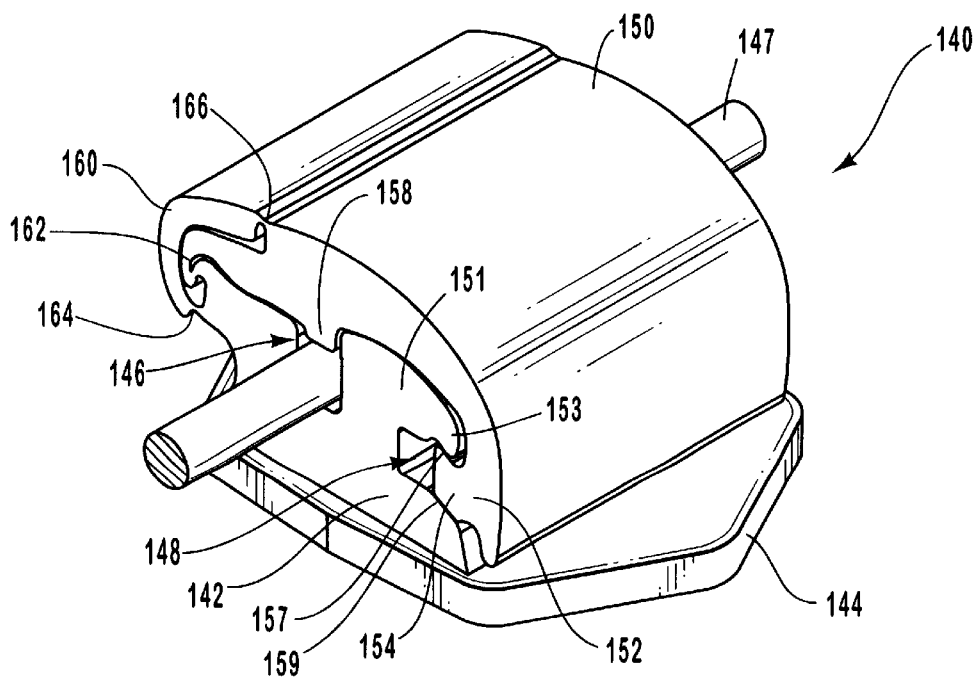
FIG. 13B is a perspective view of the orthodontic bracket of FIG. 13A with the ligation cover in a locked position.
Figure 13C:
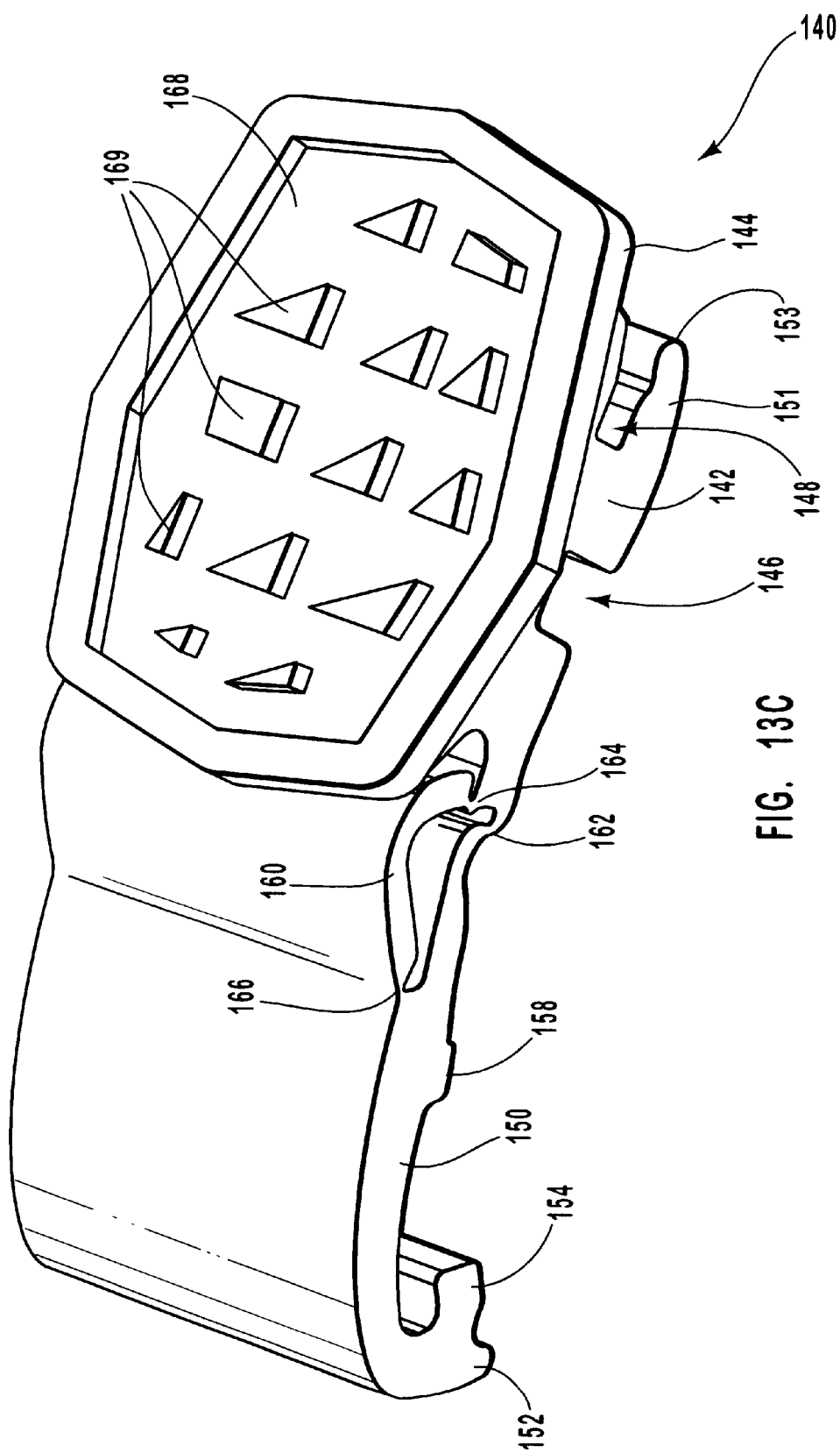
FIG. 13C is a perspective view of the underside of the orthodontic bracket of FIG. 13A.
Figure 14A:
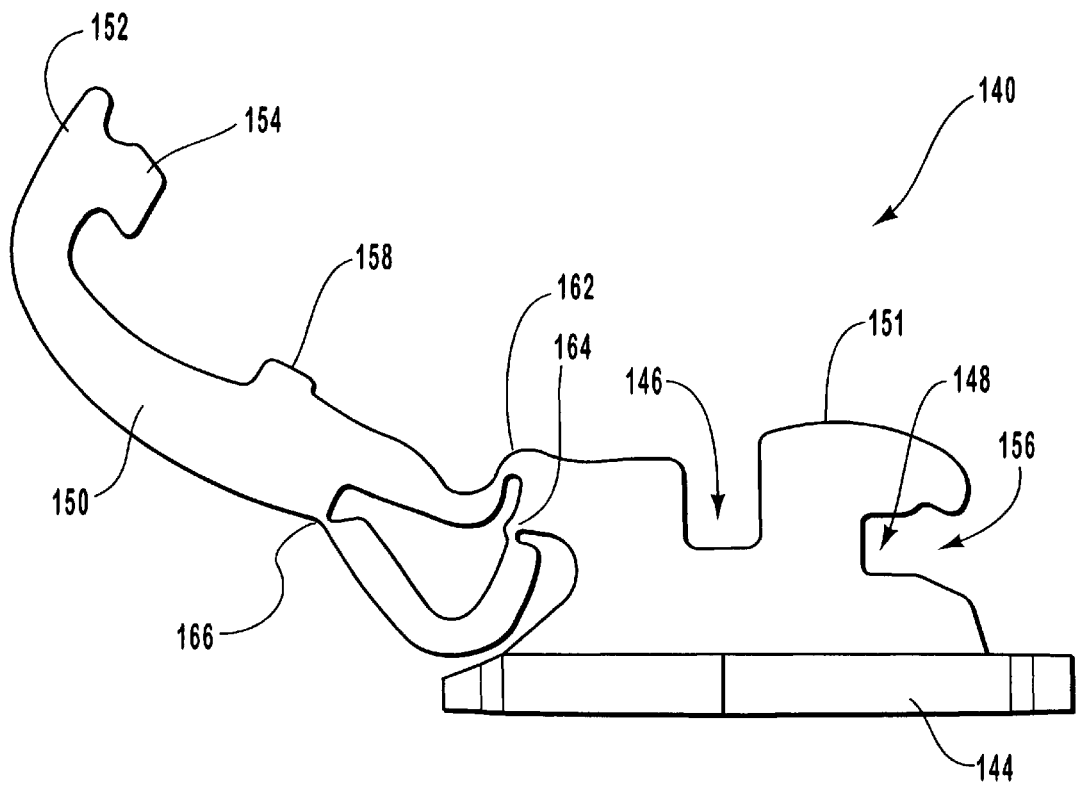
FIGS. 14A and 14B are side views of the orthodontic bracket as depicted in FIGS. 13A and 13B, respectively.
Figure 14B:
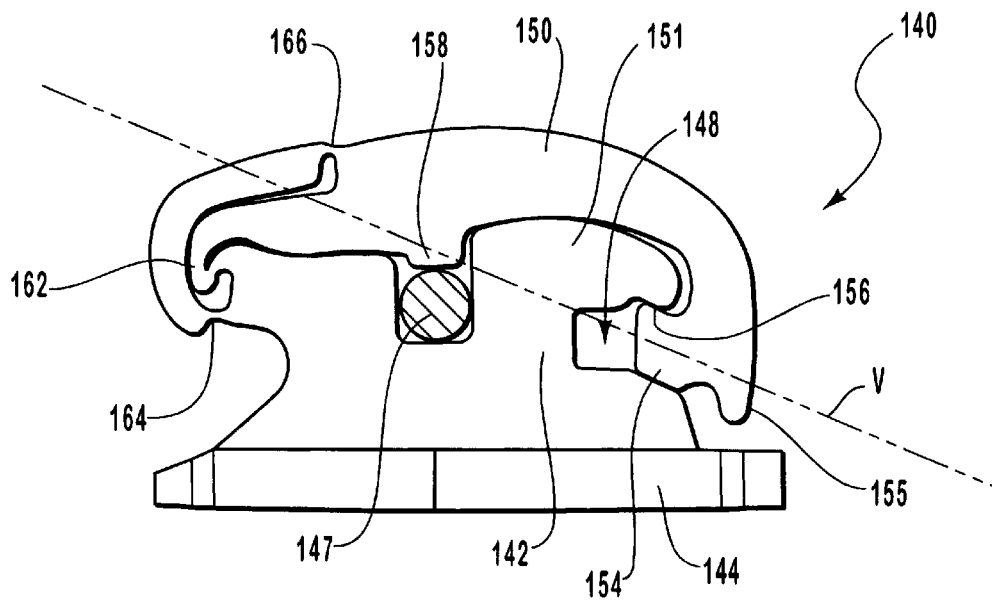

Reference is now made to FIGS. 13–15, which depict an integrally-molded one-piece orthodontic bracket 140 that includes a hinged ligation cover with a special safety locking device. As more particularly depicted therein, the orthodontic bracket 140 includes a bracket base 142 that sits atop a bonding platform 144 and that includes a main arch wire slot 146 configured to receive an arch wire 147. An auxiliary arch wire slot 148, parallel to, but opening in a direction generally perpendicular to, a longitudinal axis of the arch wire slot 146 is provided for the optional inclusion of an auxiliary arch wire (not shown).

The ligation cover 150 is hingedly attached to the bracket base 142 and configured so as to cover the arch wire slot 146, an upper side 150 of the bracket base 142, and the auxiliary arch wire slot 148 in a single closing or locking action. The ligation cover 150 includes a curved latch member 152 having a generally trapezoidal tongue 154 extending therefrom. The trapezoidal tongue 154 is configured so as to be slideably retained within an angled key way 156 extending outward from the auxiliary arch wire slot 148. The locking tongue 154 is able to snap over an outer protrusion 153 of an upper side 151 of the bracket base 142 due to the flexibility of the ligation cover 150, which allows the latch 152 to flex outwardly and away from the hinge region (discussed below). Once the locking tongue 154 has flexed outwardly and passed over and around the protrusion 153 so as to line up with the angled key way 156, the spring-like resilience of the ligation cover 150 causes the latch member 152 to retract and return to its original conformation, thereby pulling the locking tongue 154 partially into the angled key way 156 (FIGS. 14B–15A). The manner in which the trapezoidal tongue 154 and angled key way 156 serve to provide a more secure locking mechanism for retaining ligation cover 150 in a locking arrangement with bracket base 142 will be discussed hereinafter.

The ligation cover 150 is hingedly attached to the bracket base 142 by means of an integral hinge 162 (e.g., a film hinge). A spring member 160 interconnects the ligation cover 150 and the bracket base 142 in order to provide a desired resistance to inadvertent closing and opening of the ligation cover 150. As in other embodiments, the spring member 160 urges the ligation cover 150 to remain open while in an open position, and to remain closed while in a closed position. Positive force is required to selectively rotate the ligation cover 150 from a closed to an open position and from an open position to a closed position. The spring 160 is generally curved and is integrally connected to the bracket base 142 by means of an integral hinge 164 and to the ligation cover 150 by means of integral hinge 166, both of which may advantageously be film hinges. A bearing protrusion 158 extends from the ligation cover 150 and partially into or above the arch wire slot 146 when the ligation cover 150 is closed relative to the bracket base 142 in order to apply ligation pressure to the arch wire 147 and thereby provide active ligation.

Figure 15A:
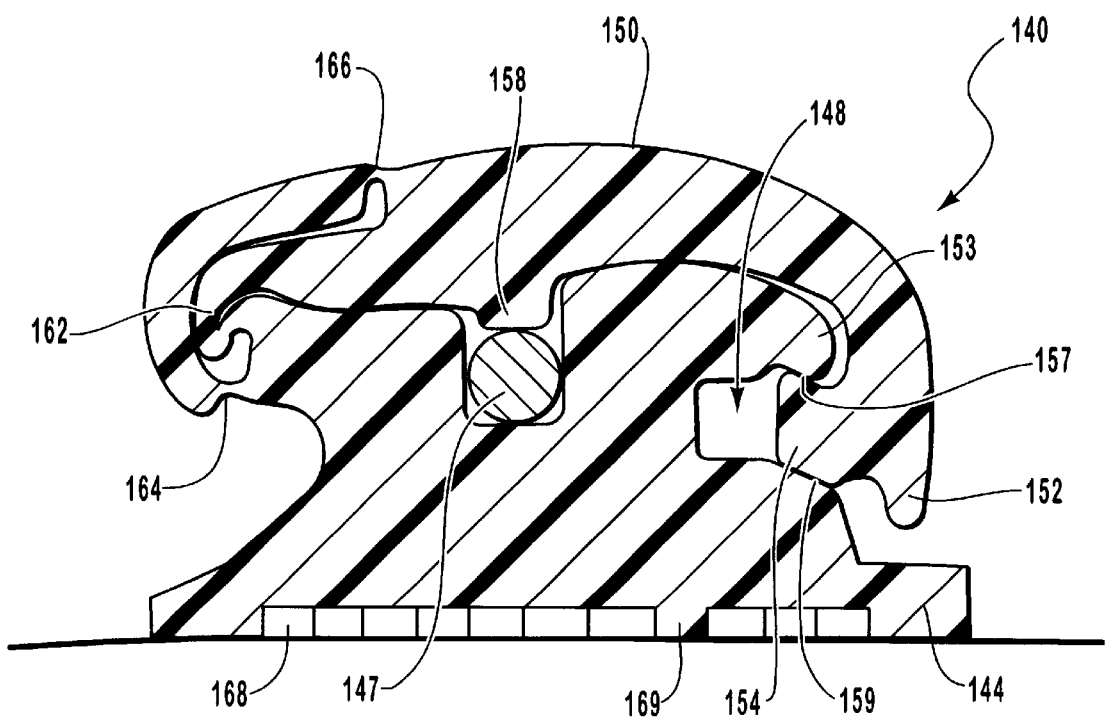
FIGS. 15A and 15B are cross-section views of the orthodontic bracket of FIGS. 13 and 14 showing how a ligation cover arching upwards in response to pressure by an arch wire causes a locking tongue of the ligation cover to be withdrawn more tightly into an angled key way of the bracket base.
Figure 15B:
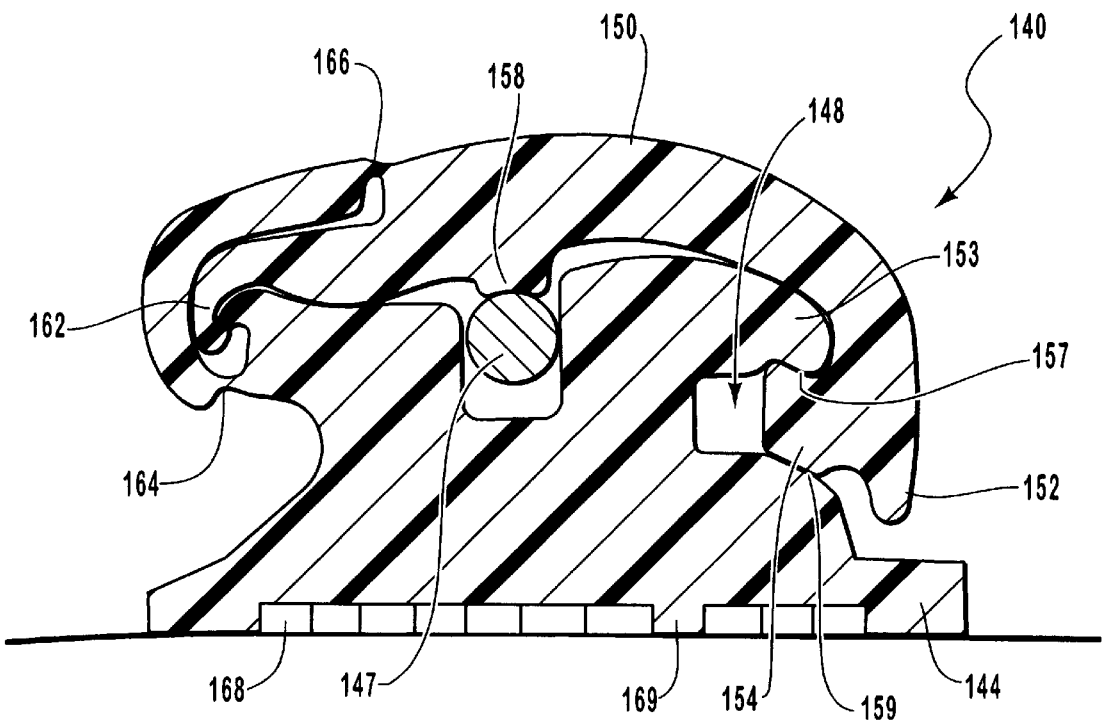

The interaction of the locking tongue 154 and the angled key way 156 serve to provide a more secure locking mechanism that prevents inadvertent unlocking and opening of the ligation cover 150. In particular, in the event that the arch wire 147 is not completely seated within the arch wire slot 146, but pushes against the bearing protrusion 158 of the ligation cover 150 with sufficient force to cause the cover 150 to bulge upwardly relative to the bracket base 142, rather than causing the tongue 154 to withdraw from the angled key way 156, which could possibly result in undesired disengagement of the latch member 152, the locking tongue 154 is instead pulled more deeply into the angled key way 156, thereby tightening the locking mechanism (FIGS. 15A and 15B).

In general, a first side of the locking tongue 154 makes slidable abutting contact with an upper surface 157 of the locking key way 156 while the ligation cover 150 is in a locked position relative to the bracket base 142. An opposite side of the locking tongue 154 makes slidable abutting contact with an angled bearing surface 159 of the angled key way 156. In this way, the locking tongue 154 is angularly restrained so that it is only able to move along an angled vector V depicted in FIG. 14B. The vector V is parallel to the angle of the trapezoid that defines the looking tongue 154 and the angle of incline of angled key way 156. The locking tongue 154 is thereby prevented from flexing outward when the ligation cover 150 bulges away from the bracket base 142. Thus, when upward pressure is exerted by the arch wire 147 to the ligation cover 50, the ligation cover 150 effectively shortens, rather than lengthens, relative to the length of the bracket base 142 such that the ligation cover 150 can only pull the locking tongue 154 more deeply into the angled key way 156. In short, the restraining action by the key way 156, coupled with an effective shortening of the ligation cover 150, reliably prevents to locking tongue 154 from moving downward along vector V so as to inadvertently slide out from the angled key way 156. Instead, upward pressure by the arch wire 147 can only have the effect of tightening, rather than loosening, the locking force between the locking tongue 154 and the angled key way 156, as shown in FIGS. 15A and 15B.

When it is desired to open or unlock the ligation cover 150, an appropriate tool, such as a fingernail or curved dental tool of the type depicted in FIG. 10B, can be used to engage a protrusion 155 extending from the latch member 152 (FIG. 14B) so as to flex the latch 152 and associated locking tongue 154 outwardly and out of the angled key way 156. Thus, the flexibility of the ligation cover 150 allows the curved latch 152 to either be released out of the angled key way 156 when pulled outwardly by an appropriate tool or to be pulled more deeply into the angled key way 156 when an arch wire pushes upward causing the ligation cover 150 to bulge outwardly and away from the bracket base 142.

Finally, as more particularly shown in FIG. 13C, the underside of platform 144 within the bracket base 142 includes a recessed area 168 and protrusions 169 disposed within the recessed area 168. The purpose of the recessed area 168 and protrusions 169 is to provide increased surface area, as well as mechanical interlocking with an adhesive, which serves to better adhere the platform 144 to a tooth. The increased surface area provides greater adhesion between the platform 144 and the tooth so as to prevent the bracket from pulling away from the tooth in a labial direction. Moreover, the protrusions 169 provide mechanical resistance to lateral movement of the orthodontic bracket 140 relative to the tooth surface.

Figure 16A:
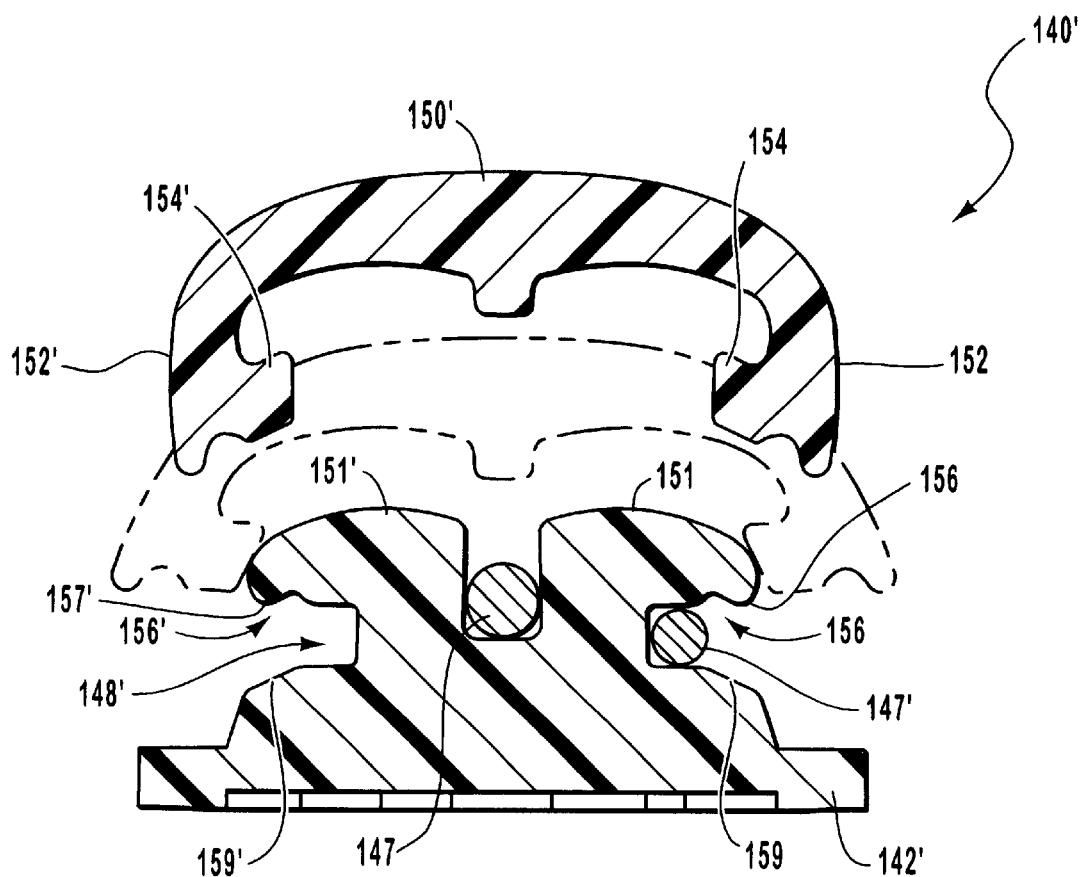
FIG. 16A is a cross-section view of a two-piece orthodontic bracket that includes special locking features on both sides, with the ligation cover removed.
Figure 16B:
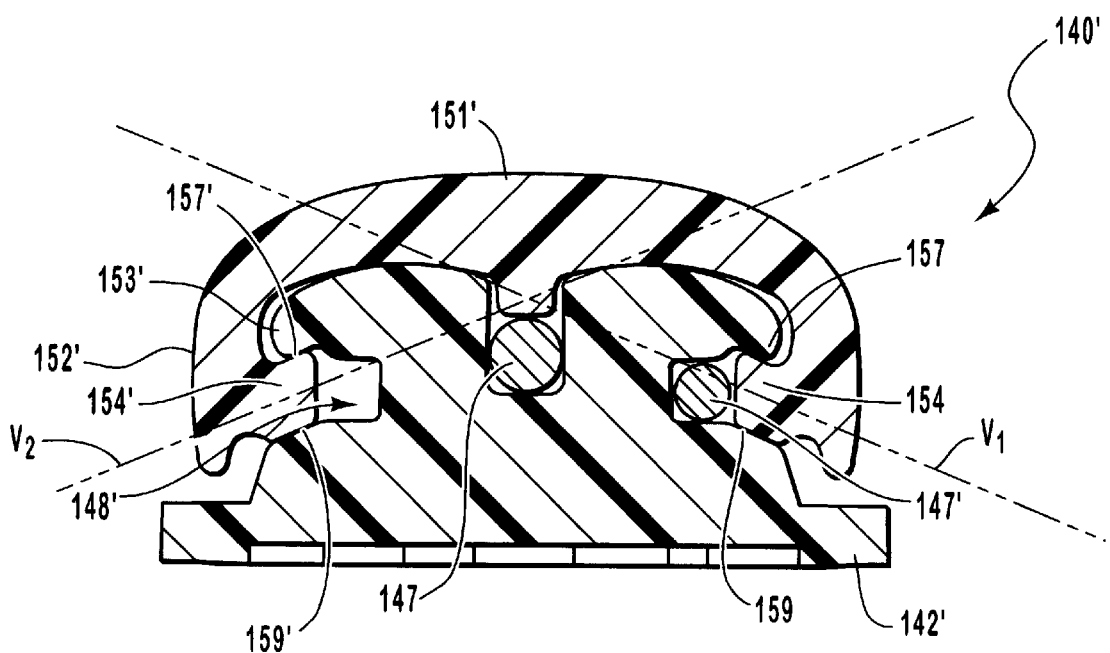
FIG. 16B is a cross-section view of the orthodontic bracket of FIG. 16A with the ligation cover attached.

FIGS. 16A–16B depict a two-piece orthodontic bracket 140' that is similar to the orthodontic bracket 140 depicted in FIGS. 13–15. The main difference is that orthodontic bracket 140' includes a ligation cover 150' that is neither hingedly attached to, nor integrally formed as a single piece with, the bracket base 142'. Instead, the ligation cover 150' is a separate and fully detachable piece. As in orthodontic bracket 140, the ligation cover 150' includes a trapezoidal locking tongue 154 that fits and locks within an angled key way 156. Because the ligation cover 150' is not hinged or otherwise connected at the other end, it also includes a second trapezoidal locking tongue 154' configured to lock with, and be received within, an angled key way 156' such that they interact together in the same way as locking tongue 154 and angled key way 156. As above, the locking tongue 154 is restrained by the confines of the angled key way 156 so that it is only capable of moving along a first vector $V_1$, which corresponds to the angle of the trapezoid that defines the locking tongue 154 and the angle of incline of angled key way 156. Similarly, locking tongue 154' is restrained by the confines of angled key way 156' such that it can only move along a second vector $V_2$ corresponding to the angle of the trapezoid of locking tongue 154 and the angle of incline of angled key way 156'. Accordingly, the ligation cover 150' includes dual safety locking features, one on either side, that serve to tighten the connection between the ligation cover 151' and the bracket base 142' in the event that upward pressure from an arch wire 147 causes the ligation cover 150' to bulge upwardly and away from the bracket base 142'.

The bracket base 142' also includes a second auxiliary arch wire slot 148', which opens up through angled key way 156'. Thus, the orthodontic bracket 140' includes three initially open arch wire slots that can be quickly and easily ligated in a single step by simply attaching the ligation cover 151' over the bracket base 142'. An optional leash member (not shown) may be included to prevent inadvertent loss of the ligation cover 150'.

Figure 17A:
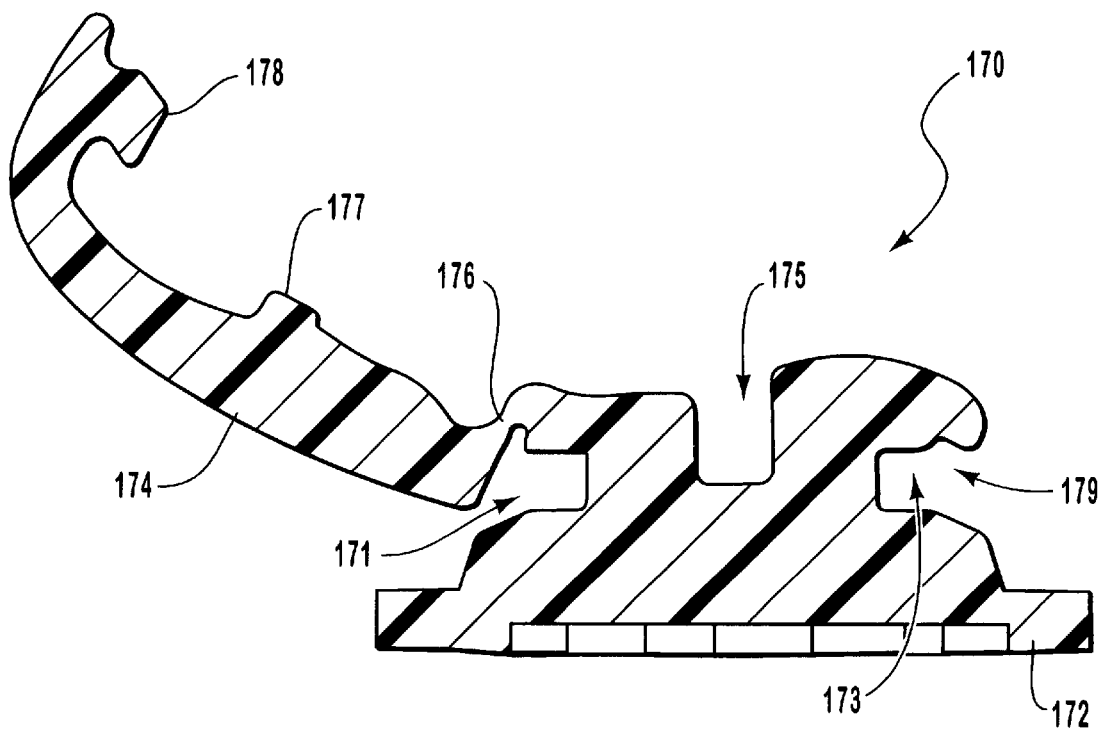
FIGS. 17A and 17B show an alternative embodiment of a hinged, one-piece orthodontic bracket having the special locking feature of the orthodontic bracket of FIGS. 13–15.
Figure 17B:
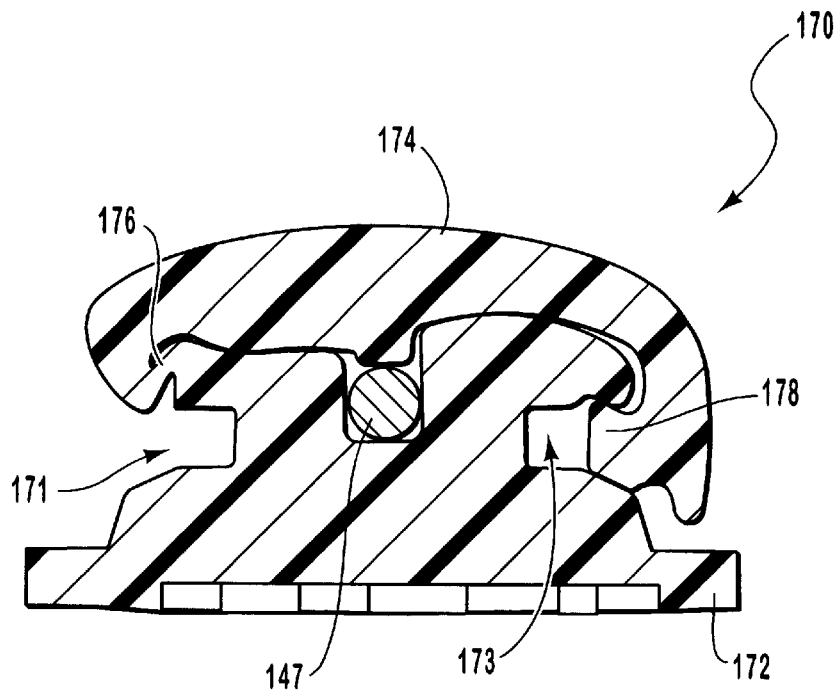

FIGS. 17A–17B depict another alternative embodiment an orthodontic bracket according to the invention. In particular, FIGS. 17A and 17B depict an orthodontic bracket 170 that is substantially similar to the orthodontic bracket 140 of FIGS. 13–15, except that bracket 170 does not include a spring member 160. Instead, a ligation cover 174 is integrally attached to the bracket base 172 by means of a single integral hinge 176 (e.g., a film hinge). This allows the ligation cover 174 to rotate more freely between an open and closed position and with less force than is required to open and close the ligation cover 150 depicted in FIGS. 13–15. In most other respects, orthodontic bracket 170 is similar to orthodontic bracket 140.

For example, the orthodontic bracket 170 includes the same safety locking features as orthodontic bracket 140, including a trapezoidal locking tongue 178 that is configured to slidably fit within an angled key way 179 within the bracket base 172. In addition, a bearing protrusion 177 extends downwardly from the ligation cover 174 and is positioned to extend partially into an arch wire slot 175 when the ligation cover 174 is in a closed and locked position relative to the bracket base 172. An auxiliary arch wire slot 173 is located next to the angled key way 176 for receipt therein of an auxiliary arch wire (not shown) that can be ligated in a single step, at the same time as arch wire 147, by closing the ligation cover 174 so that the locking tongue 178 is inserted into the angled key way 179. A second auxiliary arch wire slot 171 may optionally receive a second auxiliary arch wire (not shown) that can be ligated using convention ligatures (not shown).

Figure 18A:
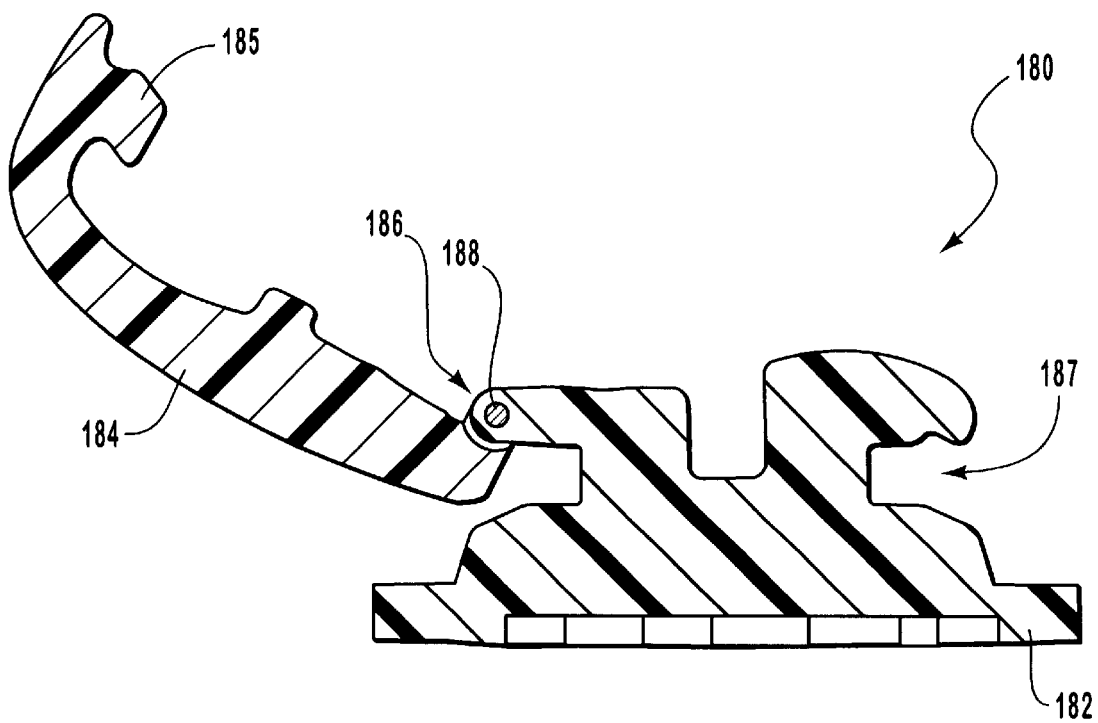
FIGS. 18A and 18B show an alternative embodiment of a hinged, two-piece orthodontic bracket having the special locking feature of the orthodontic bracket of FIGS. 13–15.
Figure 18B:
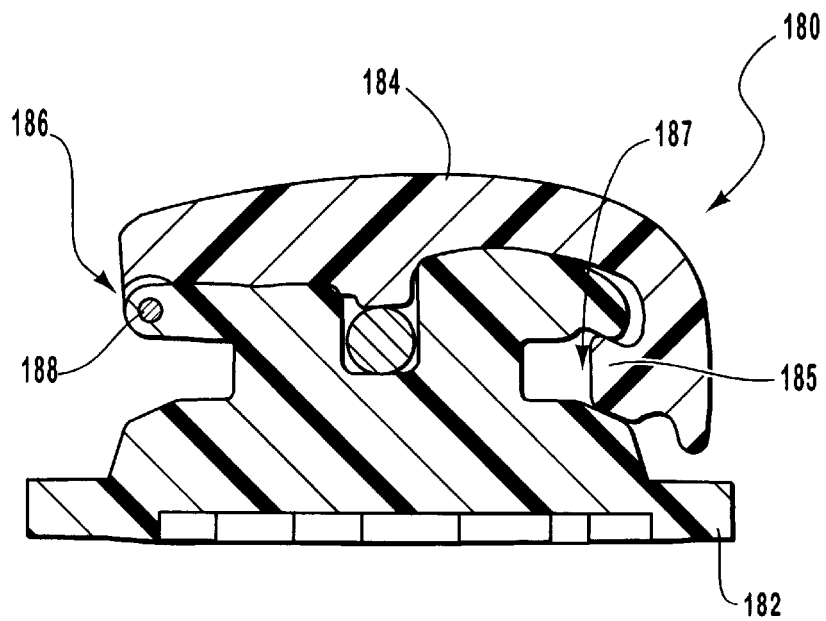

FIGS. 18A–18B depict an orthodontic bracket 180 that is similar to orthodontic bracket 170 of FIGS. 17A–17B, except that a bracket base 182 and ligation cover 184 are formed separately and then hingedly attached together by means of a conventional hinge 186, such as by means of a hinge pin 188 passing through corresponding recesses within the bracket base 182 and ligation cover 184. The orthodontic bracket 180 also includes the safety locking feature described in the preceding embodiments, including a locking tongue 185 that fits within an angled key way 187 within the bracket base 182. The bracket base 180 includes auxiliary arch wire slots (not labeled).

FIG. 18C depicts an orthodontic bracket 190 that is substantially similar to the preceding embodiments, except that the ligation cover 194 and bracket base 192 are separately formed and then connected together by means of a separate joint or connection feature 196. The connection feature 196 may comprise, for example, an elastomeric cement or glue, or fibers or a fabric integrally embedded within an end of the ligation cover 194 and a corresponding end of the bracket base 192, both of which would yield a flexible joint. In the alternative, the connection feature 196 may comprise a rigid cement or glue such that the connection feature 192 will not comprise a flexible joint. In that case, the ligation cover 194 will need to be sufficiently flexible such that it can be opened and closed without the aid of a flexible joint or hinge area.

As with previous embodiments, the orthodontic bracket 190 includes the safety locking feature described above, including a locking tongue 197 and an angled key way 198. The ligation cover 194 is also able to selectively ligate and release a pair of arch wires 147, 147' by closing and opening the ligation cover 194 relative to the bracket base 192. A third arch wire 147" can be optionally inserted into a second auxiliary arch wire slot 199 if desired. Because the ligation cover 194 does not serve to enclose auxiliary arch wire slot 199, other ligation means, such as conventional ligatures, would be necessary to ligate the auxiliary arch wire 147".

Figure 19A:
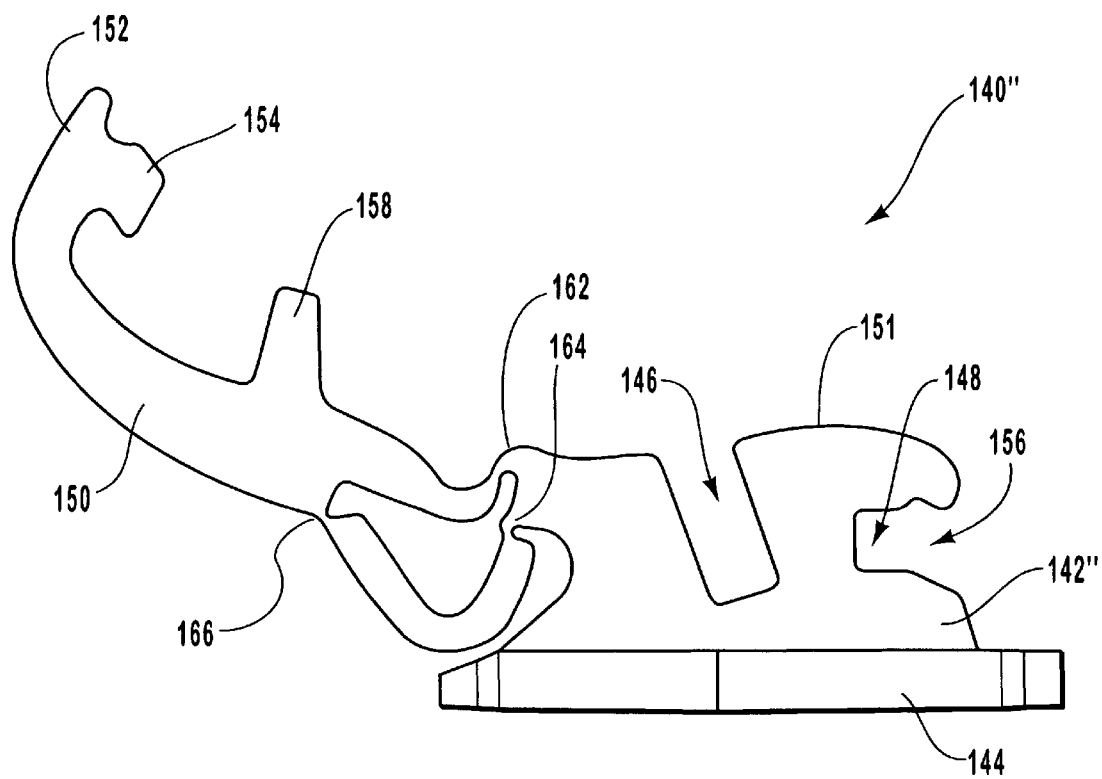
FIGS. 19A and 19B depict an orthodontic bracket having an angled arch wire slot.
Figure 19B:
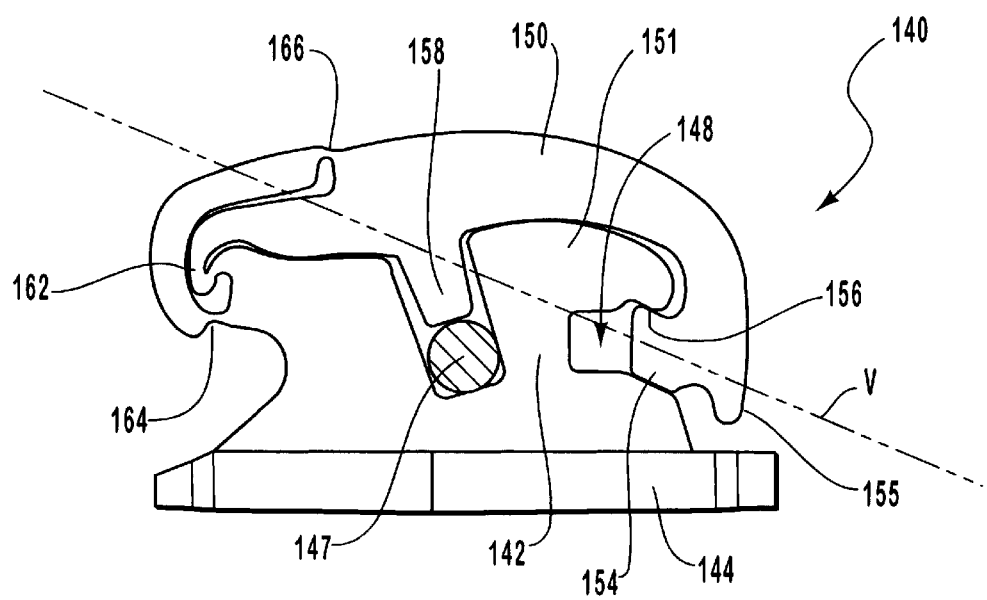

FIGS. 19A–19B depicts an orthodontic bracket 140" that is similar to the orthodontic bracket 140 depicted in FIGS. 13–15, but which includes an arch wire slot 146' that is offset at an angle such that it is not perpendicular to the bottom of the bracket base platform 144. A corresponding angled bearing protrusion 158' extends from the ligation cover 150" and is situated so as to be partially inserted into the arch wire slot 146' when the ligation cover 150" is closed in order to apply ligation pressure to the arch wire 147 and thereby provide active ligation. An angled arch wire slot may be desirable in order to provide different torquing forces to straighten a particular tooth compared to an arch wire slot that is not angled. In this particular case, the inclusion of an angled arch wire slot results in an orthodontic bracket 140" having a lower profile than orthodontic bracket 140. In most other respects, orthodontic bracket 140" is substantially similar to orthodontic bracket 140.

Figure 20A:
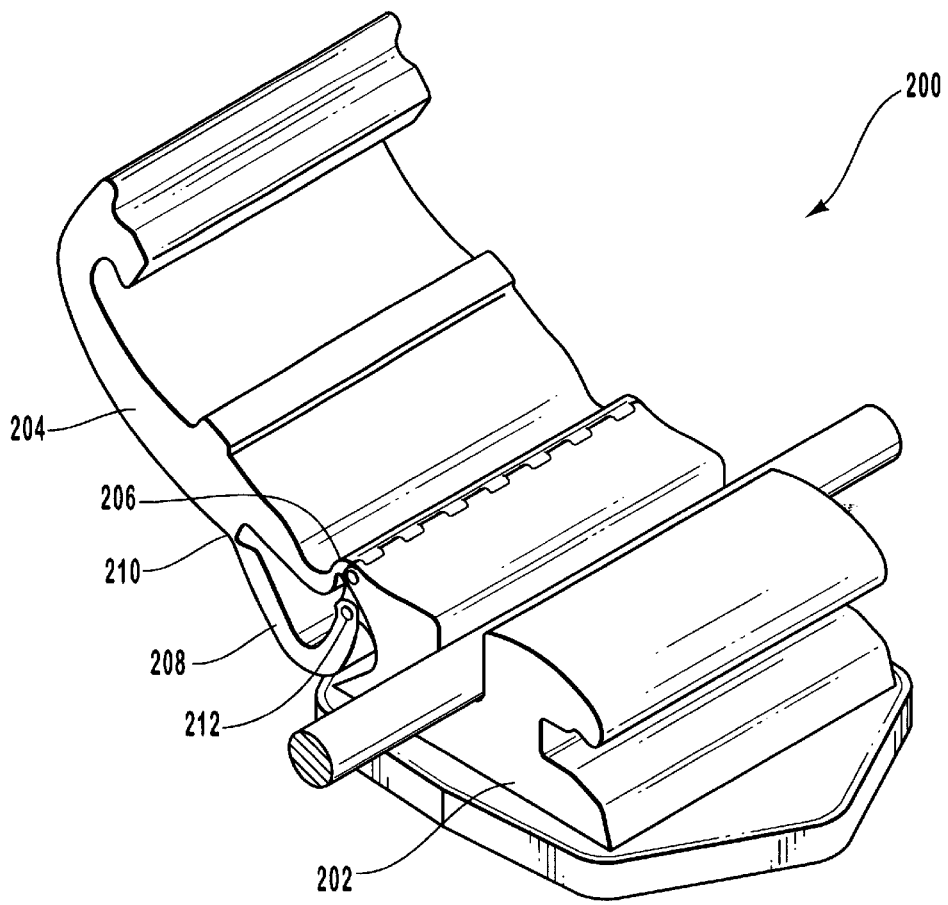
FIGS. 20A and 20B depict a hinged, two-piece orthodontic bracket having a spring element and special locking feature similar to the bracket of FIGS. 13–15.
Figure 20B:
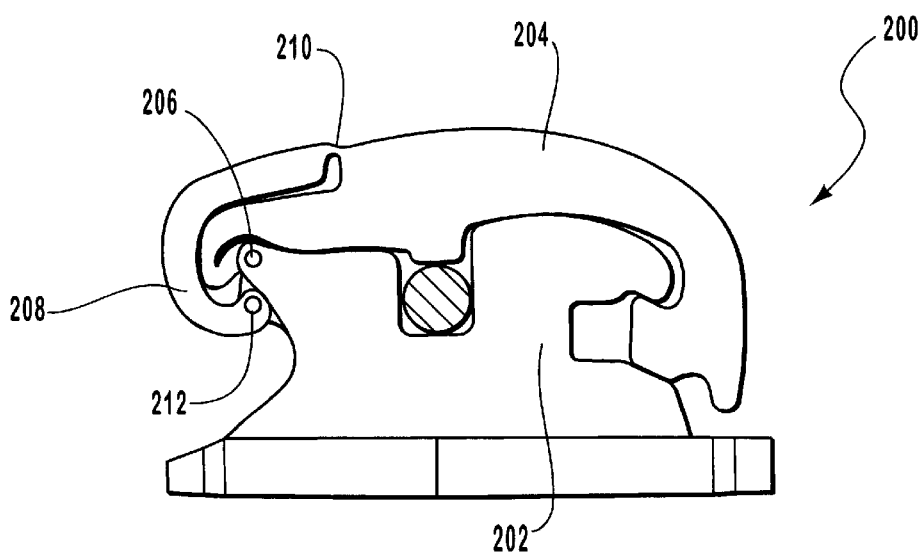

FIGS. 20A–20B depict an alternative embodiment of an orthodontic bracket according to the invention. The orthodontic bracket 200 depicted in 20A–20B differs from orthodontic bracket 140 in the manner in which the ligation cover and spring are attached to the bracket base. Instead of being connected by integral hinges, the ligation cover 204 is hingedly attached to the bracket base 202 by means of a conventional pin hinge 206. A spring member 208 is integrally molded with, and connected to, the ligation cover 204 by means of an integral film hinge 210 at one end, and hingedly attached to the bracket base 202 by means of a conventional pin hinge 212 at an opposite end. In this way, the ligation cover 204 and spring 208 can be injection molded as a single piece in one step and thereafter attached to a separately molded bracket base 202 by means of the aforementioned conventional pin hinges 206 and 212. One of ordinary skill in the art will readily appreciate, however, that the spring member 206 could alternatively be attached to the ligation cover 204 in any appropriate manner, such as by means of flexible cement or glue or a conventional pin hinge. One of ordinary skill in the art will be able to select whatever attachment means is appropriate for a particular manufacturing method.

Figure 21A:
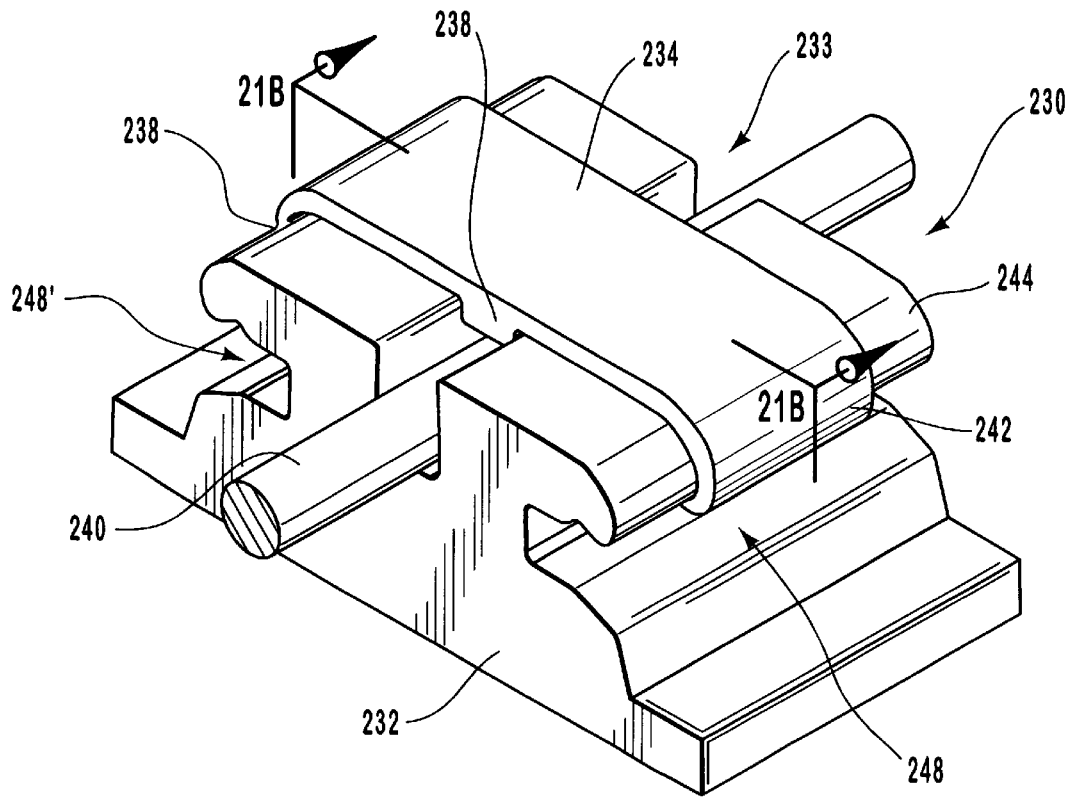
FIG. 21A is a perspective view of an orthodontic bracket in which the ligation cover and bracket base are formed from different types of plastic materials that are fused or otherwise bonded together to form an integral orthodontic bracket of essentially one piece.
Figure 21B:
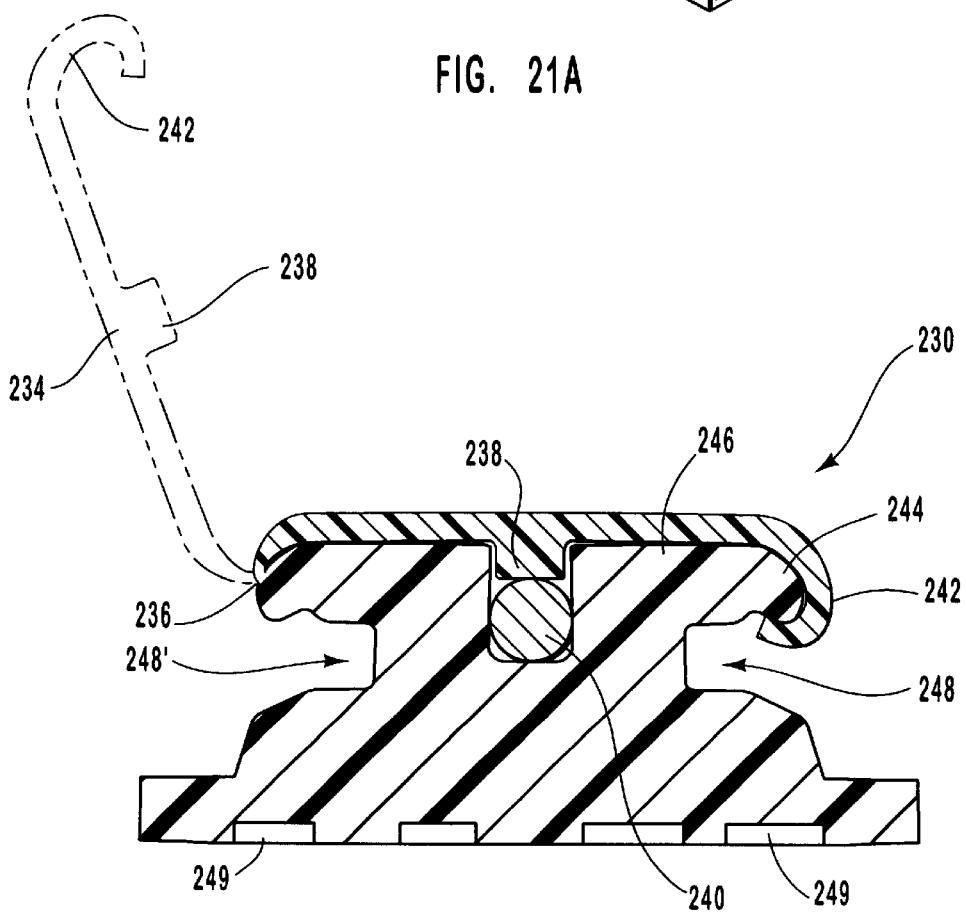
FIG. 21B is a cross-section view of the orthodontic bracket of FIG. 21A showing how the ligation cover hingedly rotates about an integral hinge element interconnecting the ligation cover and bracket base.
Figure 21C:
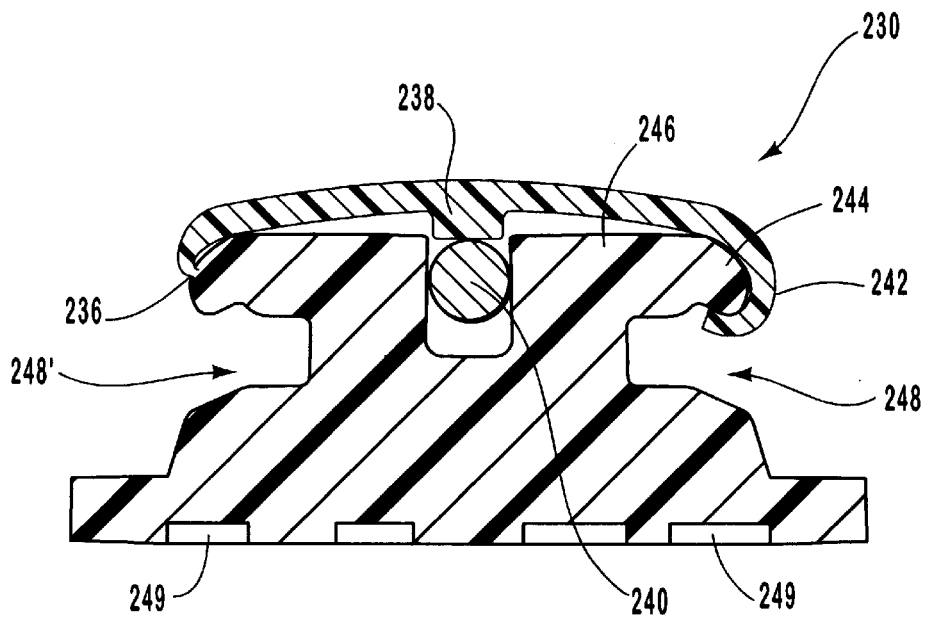
FIG. 21C is a cross-section view of the orthodontic bracket of FIGS. 21A and 21B showing how the ligation cover is able to absorb mechanical energy from an arch wire bearing upwardly against the cover.

FIGS. 21A–21C depict an orthodontic bracket 230 according to the invention that includes a bracket base 232 and ligation cover 234 that are initially molded from different types of plastics and then joined or fused together, such as by a two-color molding process. Even though the ligation cover 234 and bracket base 232 are initially molded from different types of plastics, they can be fused together to form an integral, one piece orthodontic bracket 230 in which the ligation cover 234 is hingedly attached to the bracket base 232 by means of an integral hinge 236 (e.g., a film hinge). The bracket base 232 includes a main arch wire slot 233 for receipt of an arch wire 240 therein. As seen in FIGS. 21B and 21C, the bracket base 232 further includes under cuts 249 for improved adhesion to a tooth and two auxiliary arch wire slots 248 and 248' opening on either side of the bracket base 232.

The ligation cover 234 further includes a locking clasp 242 that wraps around a nose 244 of an upper side 246 of the bracket base 232. A bearing protrusion 238 extends from the underside of the ligation cover 234 so as to partially extend into, or at least over, the arch wire slot 233 when the ligation cover 234 is in a closed or locked position relative to the bracket base 232. As shown in FIG. 21C, the flexibility and resiliency of the ligation cover 234 permits it to flex upwardly and absorb mechanical energy from the arch wire 240 when not entirely seated within the arch wire slot 233. In this way, the flexible ligation cover 234 is able to provide dynamic active ligation over time as the arch wire 240 becomes more fully seated within the arch wire slot 233.

It will be readily appreciated that the orthodontic bracket 230 of FIGS. 21A–21C could be injection molded from a single materials, such as a plastic material, to form a one-piece bracket that is integrally formed in a single step.

Figure 22:
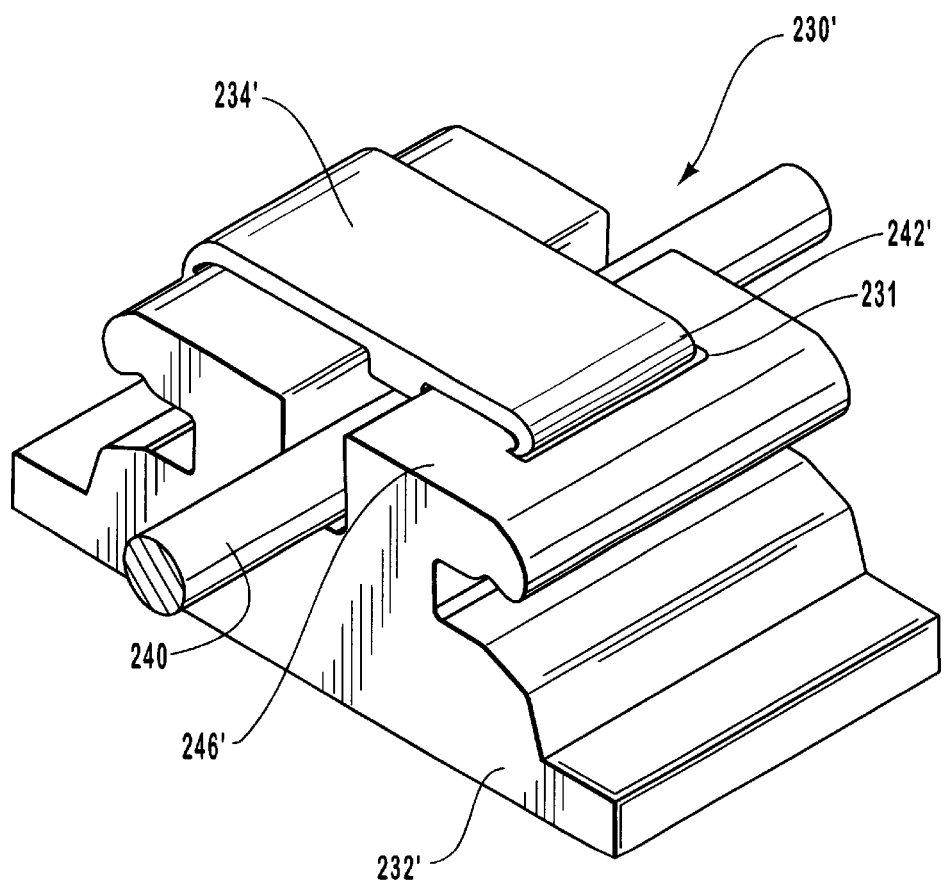
FIG. 22 is a perspective view of an orthodontic bracket that is similar to the bracket depicted in FIGS. 21A–21C, except that the ligation cover is shorter and extends over only a portion of the bracket base.

FIG. 22 depicts an orthodontic bracket 230' that is a variation of the orthodontic bracket 230 of FIGS. 21A–21C in that it includes a shorter ligation cover 234' having a curved locking clasp 242' of reduced size that can be locked to the bracket base 232' by insertion of the locking clasp 242' into a locking slot 231 formed in an upper side 246' of the bracket base 232'. In most other respects the orthodontic bracket 230' of FIG. 22 is substantially similar to the orthodontic bracket 230 shown in FIGS. 21A–21C. Because the ligation cover 234' is of shorter length, it will tend to have less flexibility than ligation cover 234 of orthodontic bracket 230, all things being equal.

As depicted in FIG. 22, the ligation cover 234' and bracket base 232' comprise different types of plastic materials, which may be separately formed and then joined together by way of a two-color molding process. It will be readily appreciated that the orthodontic bracket 230' of FIG. 22 could also be injection molded from a single plastic material to form a one-piece bracket that is integrally formed in a single step.

Figure 23A:
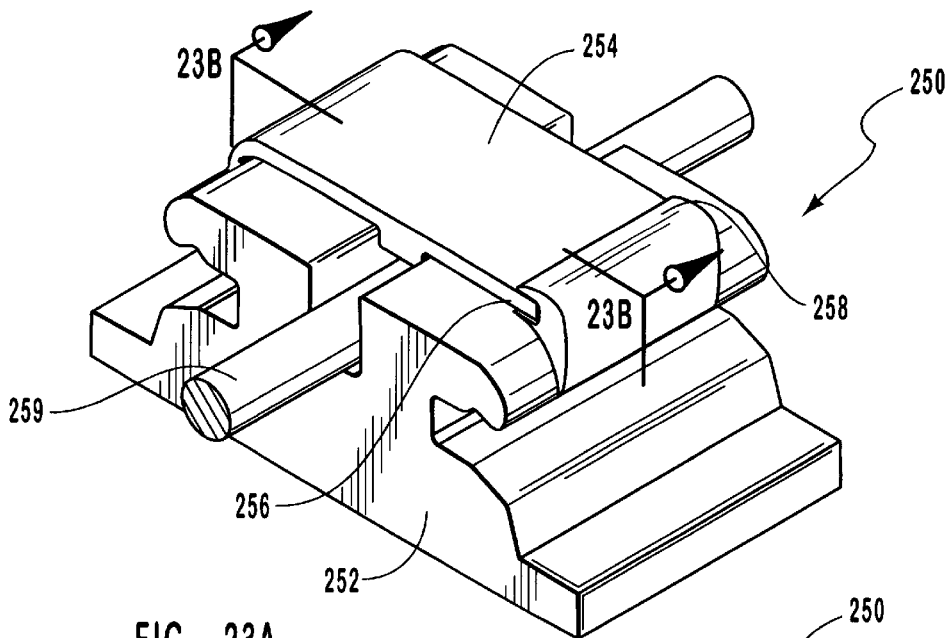
FIGS. 23A–23C depict an orthodontic bracket having a flexible ligation cover that is able to be locked and unlocked relative to the bracket base primarily due to the flexibility of the cover and its ability to be slidably inserted into and withdrawn from a lip or overhang in the bracket base.
Figure 23B:
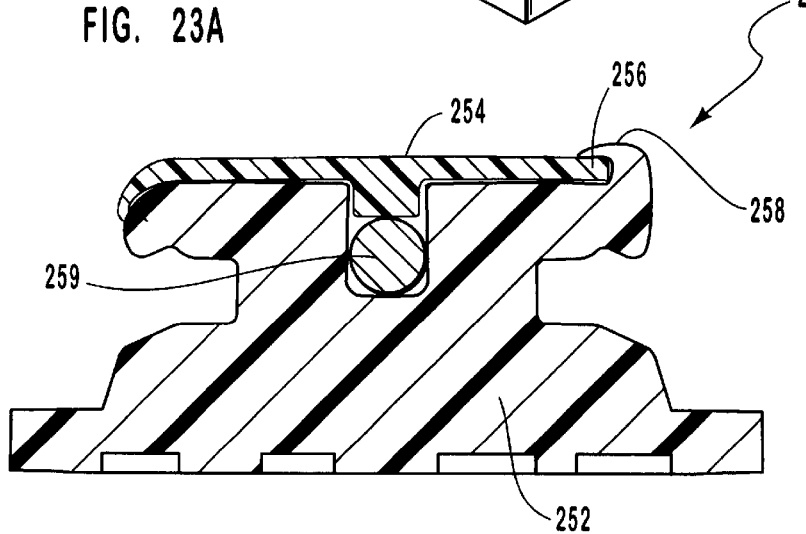
Figure 23C:
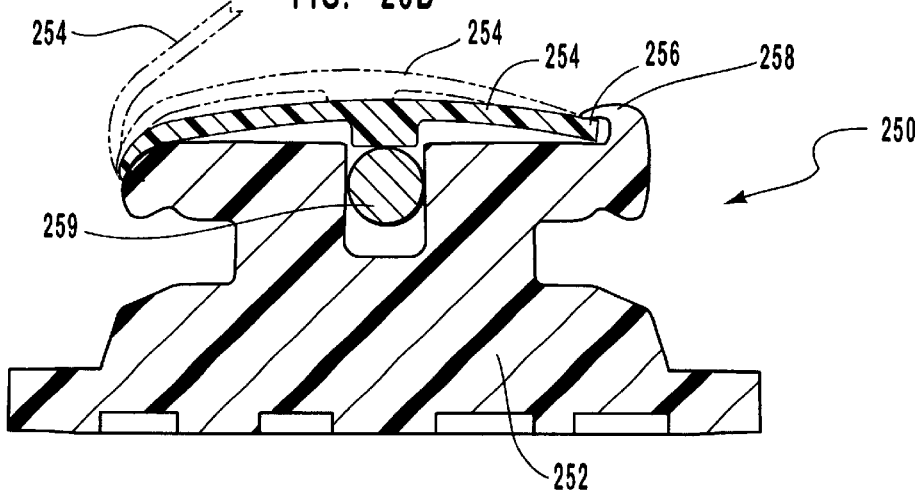

FIGS. 23A–23C depict an orthodontic bracket 250 that is initially formed in two pieces and then joined or fused together, such as by two-color molding. In particular, the orthodontic bracket 250 includes a bracket base 252 that may be advantageously manufactured from a harder, more durable plastic, while the ligation cover 254 may be advantageously formed from a more flexible and resilient plastic. Unlike previous embodiments, the ligation cover 254 includes no locking clasp or latch; instead, it merely terminates with a generally flat end 256 that slides or tucks into a locking slot or region underneath a locking lip or overhang 258 disposed at, or formed within, an upper end of the bracket base 252. Thus, the ligation cover 254 is able to become locked and unlocked primarily due to its having flexibility, rather than having a particular locking feature, such that it can be flexed outwardly from the bracket base 252 and withdrawn from the locking slot defined by the overhang or lip 258, such as by means of a conventional dental pick (not shown). Deflection of the ligation cover 254 away from the bracket base 252 effectively shortens the length of the cover 254, thereby facilitating selective insertion and withdrawal of the end 256 relative to the locking slot defined by overhang 258. This flexibility also provides the ability of the ligation cover 254 to absorb mechanical energy from an arch wire 259 bearing upward toward the cover 254. Over time, as the arch wire 259 becomes more fully seated within the arch wire slot, the resiliency of the ligation cover 254 causes it to release the stored mechanical energy, which is transferred to the arch wire 254 and/or tooth during realignment.

It will be readily appreciated that the orthodontic bracket 250 of FIGS. 23A–23C could also be injection molded from a single plastic material to form a one-piece bracket that is integrally formed in a single step. In the case where the bracket base 252 and/or the ligation cover 254 are made from metal, one end of the base and a corresponding end of the ligation cover can be affixed together by means of welding, one or more screws, rivets, pins, a mechanical hinge or other attachment means known in the art.

Figure 24A:
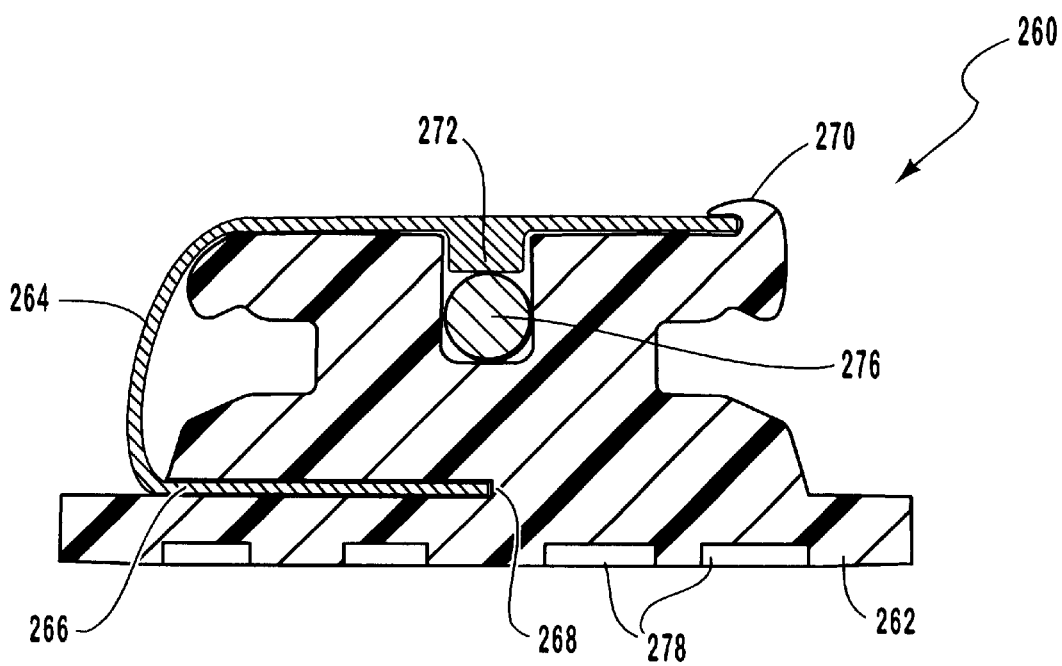
FIGS. 24A and 24B show a two-piece orthodontic bracket in which the ligation cover and bracket base have been separately formed and mechanically joined and affixed together.
Figure 24B:
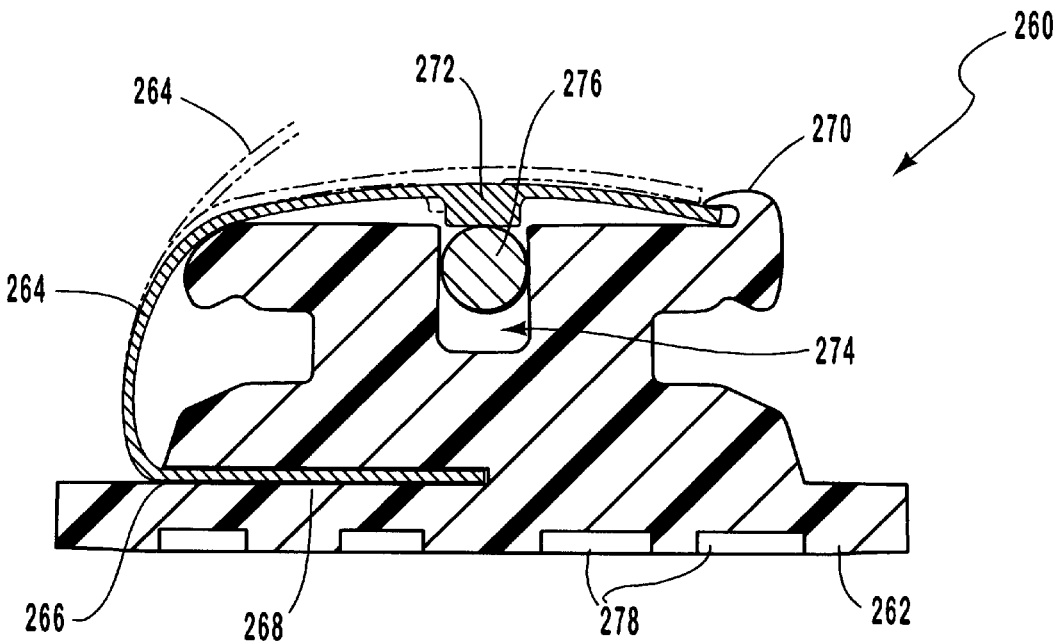

FIGS. 24A–24B depict a two-piece orthodontic bracket 260 that includes a bracket base 262 and a ligation cover 264 that are separately formed and then mechanically attached together. The bracket base 262 includes a slot 268 into which a corresponding tongue 266 of the ligation cover 264 is able to be inserted. The tongue 266 is advantageously sized relative the width of the slot 268 such that the tongue 266 will form a tight fit within the slot 268. In this way, the ligation cover 264 may be inhibited or prevented from becoming detached from, or sliding relative to, the bracket base 262. In an alternative embodiment, the tongue 266 may be sized relative to the slot 268 so that the tongue may be slidably disposed within the slot 268. Glue, welding or other securing means known in the art may be employed to affix the tongue 266 within the slot 268.

The ligation cover 264 may be manufactured from any appropriate material, e.g., metal as depicted in FIGS. 24A and 24B, so long as it is sufficiently flexible so that the ligation cover 264 is able to flex sufficiently so as to be selectively locked or unlocked within a locking slot or region beneath a locking lip or overhang 270 formed within the bracket base 262. As in previous embodiments, the ligation cover 264 may advantageously include a bearing protrusion 272 that extends partially into, or at least above, a main arch wire slot 274 within the bracket base 262 when the ligation cover 264 is in a closed position relative to the bracket base 262. The bearing protrusion 272 makes abutting contact with an arch wire 276 disposed within the main arch wire slot 274 SO as to provide active ligation. The flexible ligation cover 264 can absorb and then release mechanical energy over time from the arch wire 276, as depicted in FIG. 24B and as discussed above with respect to previous embodiments. The bracket base 262 may advantageously include recesses 278 within an underside for improved adhesion to a tooth.

Figure 25A:
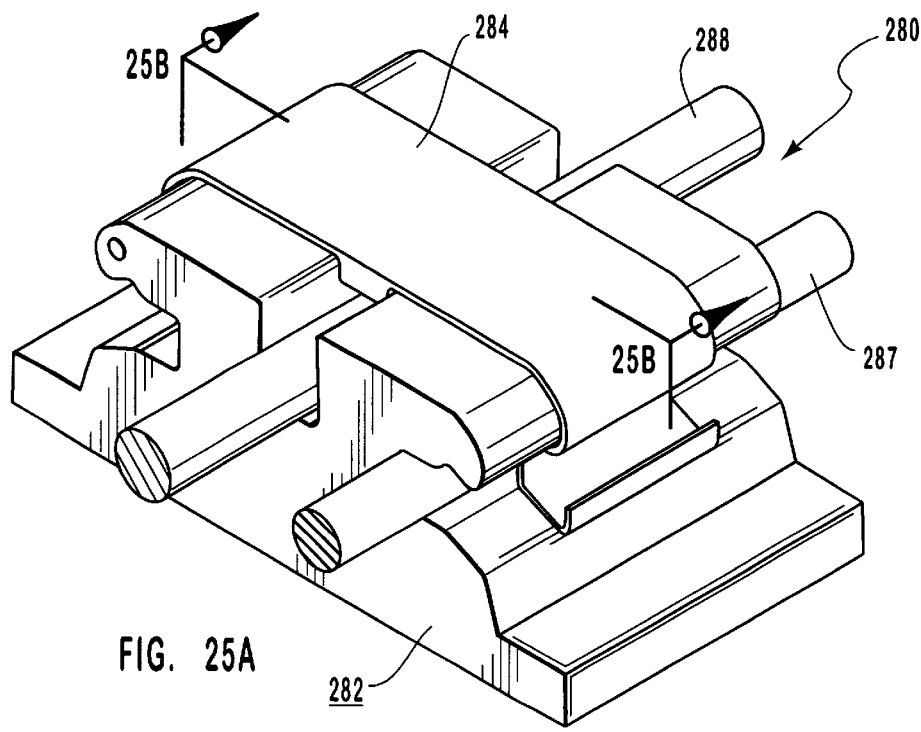
FIGS. 25A and 25B depict a two-piece orthodontic bracket in which the ligation cover is hingedly attached to the bracket base by means of a mechanical hinge and which is capable of enclosing two initially open arch wire slots.
Figure 25B:
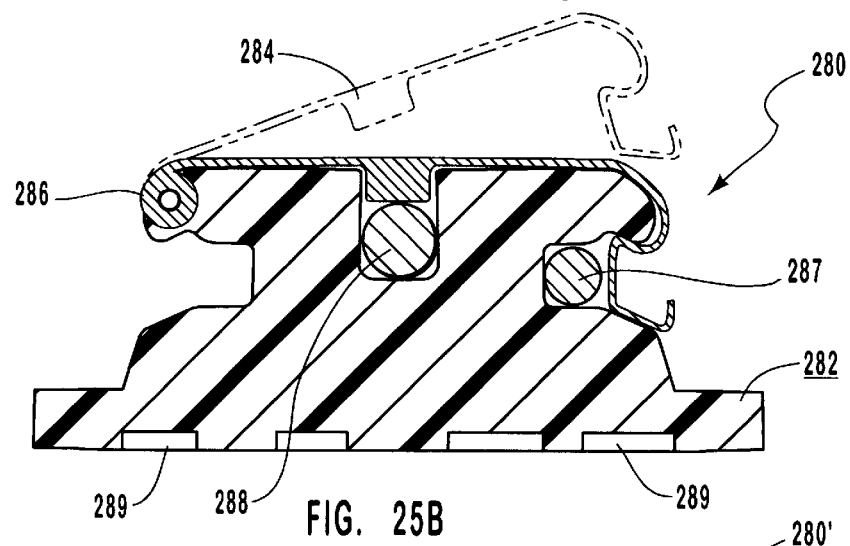

FIGS. 25A–25B depict a two-piece orthodontic bracket 280 in which a ligation cover 284 is hingedly attached to a bracket base 282 by means of a conventional pin hinge 286. The ligation cover 284 may be made from any material, such as metal as depicted in FIG. 25B, or plastic (not shown). The ligation cover 284 is also shaped so as to function in a manner similar to the special locking feature described above, which is able to tighten and form a more secure lock between the ligation cover 284 and the bracket base 282 as the ligation cover 284 is caused to bulge outwardly from the bracket base 282 as a result of upward pressure from an arch wire 288. The ligation cover is also designed so as to ligate both the main arch wire 288, as well as an auxiliary arch wire 287. The bracket base 282 includes recesses 289 for enhanced adhesion.

Figure 25C:
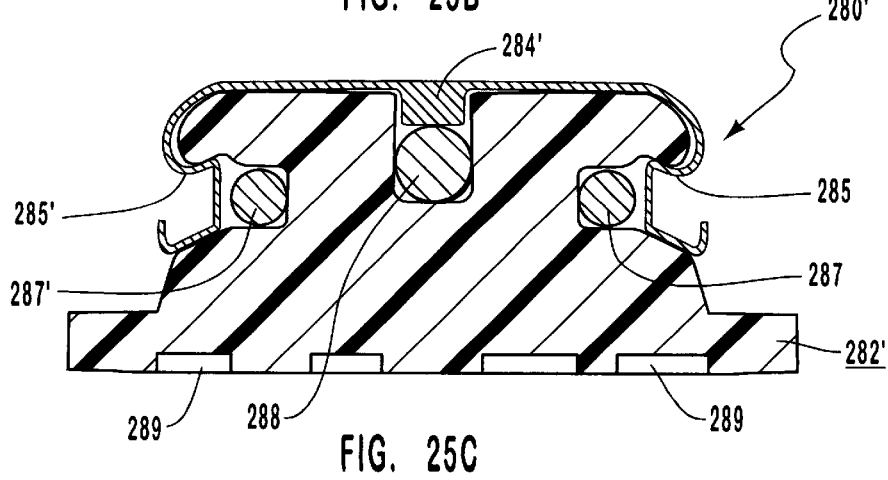
FIG. 25C is a cross-section view of a two-piece orthodontic bracket in which the ligation cover is completely detachable from the bracket base and which is capable of enclosing three initially open arch wire slots.

FIG. 25C depicts an orthodontic bracket 280' that is a variation of the orthodontic bracket 280 of FIGS. 25A and 25B, except that the ligation cover 284' is not hingedly attached to the bracket base 282', but is rather separate and completely removable. The ligation cover 284' is shaped so as to include special trapezoidal locking features 285 and 285', similar to those described above in previous embodiments, on either side of the cover 284', which tighten as the ligation cover 284' is flexed upwardly away from the bracket base 282' by means of an arch wire that is not completely seated with a main arch wire slot. The ligation cover 284' is further able to ligate two auxiliary arch wires 287 and 287' at the same time as the main arch wire 288 in a single ligation step of attaching the ligation cover 284' to the bracket base 282'. When the ligation cover 284' is removed from the bracket base 282', all three of arch wire slots 288, 287 and 287' are completely open and able to receive an arch wire therein.

Figure 26A:
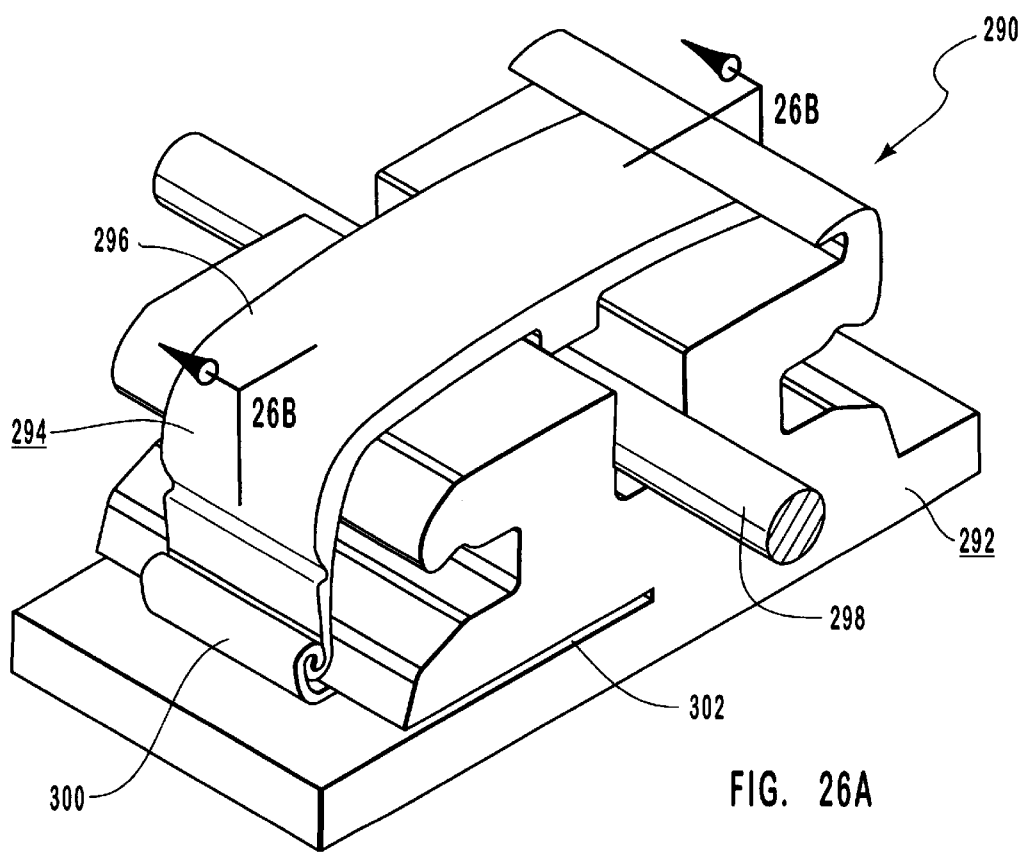
FIGS. 26A and 26B show a two-piece orthodontic bracket having a film hinge in a location other than where the ligation cover is attached to the bracket base.
Figure 26B:
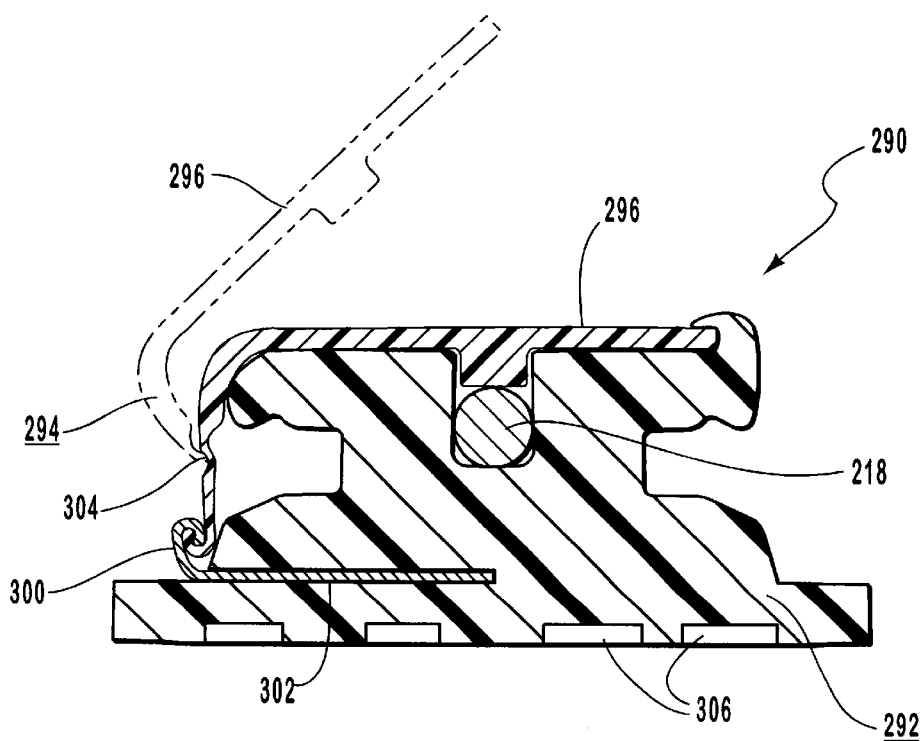

FIGS. 26A and 26B depict an orthodontic bracket 290 that is manufactured in two or three pieces and then assembled to form an orthodontic bracket having a hinged ligation cover 294 that is affixed to a bracket base 292. The ligation cover 294 is manufactured from either a single material, such as plastic or metal, or from two separate materials, as depicted in FIG. 26B, such as a plastic material for a hinged portion 296 that opens and closes so as to ligate an arch wire 298, and a metal for an attachment portion 300. One side of the attachment portion 300 slides into a slit 302 formed within the bracket base 292, and another side is crimped around, or otherwise affixed to, the hinged portion 296, such as by means of an appropriate glue or cement. The attachment portion 300 may either be slidably or fixedly attached to the bracket base 292. The ligation cover 294 further includes a film hinge 304 within the hinged portion 296. This allows the hinged portion 296 of the ligation cover 294 to pivot or rotate about a film hinge located in the ligation cover itself, rather than at a joint between the ligation cover and bracket base, as in previous embodiments. The bracket base 292 may advantageously include recesses 306 for improved adhesion of the bracket base 292 to a tooth. The hinged portion 296 is advantageously flexible to assist inserting an end of the hinged portion distal to the hinge 304 under a corresponding lip, overhang or other locking feature associated with the bracket base 292.

Although the foregoing embodiments are discussed and depicted as being able to selectively ligate and release an arch wire by locking and unlocking (or opening and closing) of the ligation cover relative to the bracket base, it will be appreciated that the ligation cover can be permanently affixed to the bracket base, if so desired, at any time through the application of an appropriate glue or cement material at or near the clasp, latch or other locking mechanism between the ligation cover and bracket base.

C. Summary of Improved Structural and Functional Features

The exemplary orthodontic brackets described in the preceding section include one or more structural and/or functional features that are believed to be improvements over conventional orthodontic brackets. A more focused summary will now be provided in order to better appreciate the advantages of such improvements.

1. Orthodontic Brackets With Ligation Covers That Incorporate a Film Hinge.

A first improvement in the art is a self-ligating orthodontic bracket that, at a minimum, includes a bracket base for attachment to a tooth, a ligation cover, and a film hinge about which at least a portion of the ligation cover can rotate so as to permit selective locking and unlocking of the ligation cover in order to ligate an arch wire received by the bracket base. As set forth above, the term "film hinge" refers to a local area of reduced cross-Page sectional thickness that facilitates preferential localized bending of an article or device at the region of the film hinge. In the context of the ligation cover of an orthodontic bracket, a film hinge permits the cover to rotate or pivot about the film hinge such that the film hinge defines the origin of the radius of the arc or rotation of the ligation cover. In this way, the film hinge provides a definite point or line about which the ligation cover will always rotate, which reduces or eliminates unwanted bending stresses elsewhere in the cover (or place of attachment to the bracket if other than at the film hinge itself).

Moreover, a reduced cross section within a resilient plastic material yields a living hinge that can be rotated back and forth a number of times without becoming fatigued to the point of premature breakage. Of course, one of ordinary skill will readily appreciate that the ligation cover of an orthodontic bracket is rarely opened and closed more than a few times over the lifetime of the bracket, which includes installing the bracket, ligating an arch wire therewithin, and subsequent adjustments if needed. Thus, a film hinge can be employed in ligation covers made of other materials such as metals and more rigid plastics.

Orthodontic brackets that incorporate a film hinge may manufactured as a single integral piece (see FIGS. 1, 4, 5, 7, 10, 12–15 and 17) or initially formed as two pieces that are joined or fused together using two-color molding of dissimilar plastics (see FIGS. 20–22). They may comprise two or more distinct pieces and/or materials that are mechanically attached together (see FIG. 26). The film hinge may be located at the location where the ligation cover is attached to the bracket base, or it may be located elsewhere. The bracket base may comprise any desired material of acceptable durability, such as metal, ceramic or rigid plastic, while the cover may comprise any desired material of acceptable flexibility and resilience, such as plastic or metal. A ligation cover that includes a film hinge may be locked or attached to the bracket base using any locking or attachment mechanism described herein or known in the art. The ligation cover may cover all or only a portion of the upper surface of the bracket base. An orthodontic bracket may include one or a plurality of film hinges as desired.

2. Orthodontic Brackets Incorporating an Arch Wire Bearing Spring Within the Ligation Cover.

A second improvement in the art is a self-ligating orthodontic bracket that, at a minimum, includes a bracket base for attachment to a tooth, a ligation cover, and a bearing spring extending downward from the ligation cover that is capable of being compressed by an arch wire that is not entirely seated within a slot or other arch wire retention means associated with the base so as to absorb mechanical energy from the arch wire. Such mechanical energy is then transferred to the tooth and/or back to the arch wire over time during realignment of the tooth, during which the initially compressed spring expands or extends so as to maintain continuous pressure onto the arch wire, which over time tends to become better seated relative to the bracket base. In this way, the bearing spring provides for dynamic active ligation of an arch wire during tooth realignment. Exemplary arch wire bearing springs are illustrated in FIGS. 5, 7–10, 12. In this way, the bearing spring yields an orthodontic bracket that is able to provide dynamic active ligation of an arch wire over time as the arch wire moves relative to the ligation cover and becomes better seated within the arch wire slot during tooth realignment.

The ligation cover may be integrally connected to the bracket base, such as by being injection molded as a single piece or being joined together by two-color molding. Alternatively, the ligation cover may be completely separate and detachable from the bracket base. The base can be any rigid or durable material, such as metal, plastic or ceramic, while the cover can be any flexible and resilient material such as plastic or metal. The bearing spring may my integrally formed with the ligation cover, and therefore comprise the same plastic or metal material, or it may comprise a different material than the cover, such as a metallic bearing spring having increased wear resistance when contacted by an arch wire that is attached to the ligation cover.

3. Spring Action from Ligation Cover to Wire for Dynamic Active Ligation.

A third improvement in the art is a self-ligating orthodontic bracket that, at a minimum, includes a bracket base for attachment to a tooth and a ligation cover that includes means for absorbing mechanical energy from an arch wire and then releasing such energy over time back to the arch wire and/or a tooth during tooth realignment. The arch wire bearing spring described in the immediately preceding section constitute an example of means for absorbing and releasing mechanical energy from the arch wire in order to provide for dynamic active ligation during tooth realignment. In is also within the scope of the invention to provide alternative means for absorbing and releasing mechanical energy from the arch wire, such as a ligation cover that has sufficient flexibility and resiliency so that it is able to temporarily deform or deflect and absorb energy from an arch wire pressing upwards against the cover. Thereafter, this stored mechanical energy is released back to the arch wire and/or tooth in order to urge migration of the tooth into proper alignment and better seat the arch wire in the slot. Examples of ligation covers that are explicitly depicted as having absorbed arch wire energy are include FIGS. 15B, 21C, 23C and 24B, although other embodiments are described as optionally or explicitly providing this function.

In the case where a flexible cover is relied upon to provide the sole means of providing dynamic active ligation of the arch wire, it will be preferable for the ligation cover to be attached to the bracket base in a manner so that the ligation cover does not slide relative to the bracket base during selective ligation and release of the arch wire. It is more preferably for the ligation cover to be hingedly attached at one end by a hinge feature that permits the ligation cover to rotate about the hinge.

The orthodontic bracket may comprise any appropriate material(s) and may be a one-or multi-piece bracket.

4. Orthodontic Bracket that Includes a Deformable Ligation Cover to Facilitate locking and Unlocking.

A fourth improvement in the art is a self-ligating orthodontic bracket that, at a minimum, includes a bracket base for attachment to a tooth, a locking slot, stationary lip, overhang or other locking clasp associated with the base for slidably receiving therein an end of a flexible ligation cover, and a ligation cover fixed to the bracket base at one end and having sufficient flexibility and resilience so as to be slidably inserted and removed from the locking clasp associated with the bracket base. Examples of such brackets are depicted in FIGS. 23, 24 and 26.

The bracket base and ligation cover may comprise any appropriate material, such as metal, plastic or ceramic. They may be formed as an integral, one-piece bracket, or they may be separately formed and then joined together, such as by mechanical means, adhesion or being fused together (e.g., two-color molding of two separately molded plastic parts). The flexible ligation cover may or may not be hinged relative to the bracket base, such as by a film or pin hinge.

5. Spring For Providing Resistance to the Rotation of a Ligation Cover About a Hinge.

A fifth improvement in the art is a self-ligating orthodontic bracket that, at a minimum, includes a bracket base for attachment to a tooth, a ligation cover hingedly attached to the base, and a spring element that interconnects the bracket base and ligation cover and urges the ligation cover to remain open while in an open position and/or to remain closed while in a closed position relative to the bracket base. Examples of spring devices or elements that provide the afore-mentioned function are illustrated in FIGS. 1, 5, 7, 10, 12–15 and 20. It will be appreciated that other spring designs and arrangements relative to the bracket base and ligation cover, in addition to those explicitly depicted in the drawings, are contemplated and within the scope of the invention.

The bracket base, ligation cover and spring may comprise any appropriate material, such as metal, plastic or ceramic. The spring element may be attached to the bracket base and ligation cover by any appropriate means, such as by being integrally molded thereto, through the use of an adhesive (e.g., chemical or light curable), two-color molding or other methods of fusing the spring between the cover and base (e.g., by welding plastic or metal pieces together), or by attachment by mechanical hinges.

6. Ligation Cover Biased Toward Remaining in an Open or Closed Position.

A sixth improvement in the art is a self-ligating orthodontic bracket that, at a minimum, includes a bracket base for attachment to a tooth, a ligation cover hingedly attached to the base, and spring means for urging the ligation cover to remain open while in an open position and/or to remain closed while in a closed position relative to the bracket base. The spring element interconnecting the bracket base and ligation cover described in the immediately preceding section constitutes an example of means for urging the ligation cover to remain open and/or closed. In is also within the scope of the invention to provide alternative means for urging the ligation cover to remain open and/or closed. Examples include elastomeric hinges and resilient materials that have elastic memory (see FIG. 18C). For example, one or more elastomeric spring elements may be disposed between the ligation cover and bracket base in a manner so as to either bias the ligation cover toward remaining in a closed position or toward remaining in an open position. Whether an elastomeric spring element will tend to bias the ligation cover into remaining in an open or closed position will depend on its location relative to the ligation cover and base.

Materials that have "elastic memory" include materials whose molecular structure resists stretching, bending or other forms of deformation in the short term, such as for a few second or minutes, but which will relax and assume the new, deformed position and resist being deformed into a new position, even the original position. One of ordinary skill in the art will be able to select an appropriate material having said "elastic memory" function.

The bracket base and ligation cover may comprise any appropriate material, such as metal, plastic or ceramic. They may be formed as an integral, one-piece bracket, or they may be separately formed and then joined together, such as by adhesion using an elastomeric material or a material having elastic memory.

7. Two-Color Molding of Bracket Base and Ligation Cover Using Different Types of Plastics.

A seventh improvement in the art is a self-ligating orthodontic bracket that, at a minimum, includes a bracket base for attachment to a tooth that is molded using one type of plastic and a ligation cover that is molding using another type of plastic and which has been fused or otherwise affixed to the bracket base using a two-color molding process. Employing two-color molding permits the bracket base to be manufactured from a first plastic material that is advantageous for use in making bases and the ligation cover to be make from a second plastic material that is advantageous for use in making covers.

For example, it is generally desirable for the bracket base to be rigid and durable so as to remain affixed to a tooth, while resisting being deformed or damaged by the forces applied thereto by one or more arch wires. Flexibility is typically not beneficial to the operation and function of the bracket base. On the other hand, it is generally desirable for the ligation cover to be more flexible and resilient, e.g., to permit the cover to be locked and unlocked relative to the base and/or to absorb, store and release mechanical energy from the arch wire, so as to provide dynamic active ligation of the arch wire. If a spring element is used to provide additional resistance to opening or closing of the ligation cover, it may be integrally manufactured from the same plastic used to make either the bracket base or the ligation cover, or it may optionally be molded using a third type of plastic material and then attached to the base and cover using two-color molding.

Based on the advantages of using two-color molding, which become readily apparent when reading the present disclosure, one of ordinary skill in the art will be able to select appropriate plastic materials for use in manufacturing an orthodontic bracket using two-color molding. One of ordinary skill in the art will also know how to incorporate typical two-color molding processes known in the art for manufacturing articles of manufacture that incorporate two or more different types of plastic materials. Orthodontic brackets depicted as including a plurality of different types of plastic materials are illustrated in FIGS. 21–23.

8. Two or More Initially Open Arch Wire Slots that Can be Ligated by Single Cover.

An eighth improvement in the art is a self-ligating orthodontic bracket that, at a minimum, includes a bracket base for attachment to a tooth that includes two or more different arch wire slots and a ligation cover that is able to ligate two or more different arch wires in a single action of closing or locking the ligation cover relative to the base. Examples of brackets that include at least two initially open slots that are ligated by the single action of locking or attaching a ligation cover to a bracket base are illustrated in FIGS. 5, 7, 8, 10, 12–20 and 25.

The bracket base and ligation cover may comprise any appropriate material, such as metal, plastic or ceramic. They may be formed as an integral, one-piece unit, or they may be separately formed and then joined together, such as by mechanical means, adhesion, or being fused together (e.g., two-color molding of two separately molded plastic parts). If the ligation cover is made separately from the bracket base, it is either attached at one end to the base or it is attached over the base by bringing the cover toward the base. The ligation cover is preferably not slidably attached to the bracket base in this embodiment.

9. Bracket With Safety Locking Feature to Provide Enhanced Locking of the Ligation Cover to the Bracket Base.

A ninth improvement in the art is a self-ligating orthodontic bracket that, at a minimum, includes a bracket base for attachment to a tooth, a ligation cover that is able to absorb mechanical energy from an arch wire, and a special locking feature that locks the cover to the base with increasing force as more force is applied from an arch wire against the cover. In this way, the special locking feature prevents an arch wire bearing outwardly against the ligation cover from undesirably opening or unlocking the cover relative to the bracket base. This provides a safety feature that prevents or inhibits orthodontic brackets attached to particularly crooked teeth from inadvertently or prematurely releasing or relaxing its grip on the arch wire, which would typically require readjustment or replacement of the bracket by the orthodontist. Example of orthodontic brackets that include a locking feature that provides this desired function are illustrated in FIGS. 13–20 and 25.

The bracket base and ligation cover may comprise any appropriate material, such as metal, plastic or ceramic. They may be formed as an integral, one-piece bracket, or they may be separately formed and then joined together, such as by mechanical means, adhesion, or being fused together (e.g., two-color molding of two separately molded plastic parts). The ligation cover may be hinged at one end and include the locking feature at the free end, or the cover may be completely removable from the bracket base and include the locking features at both ends.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

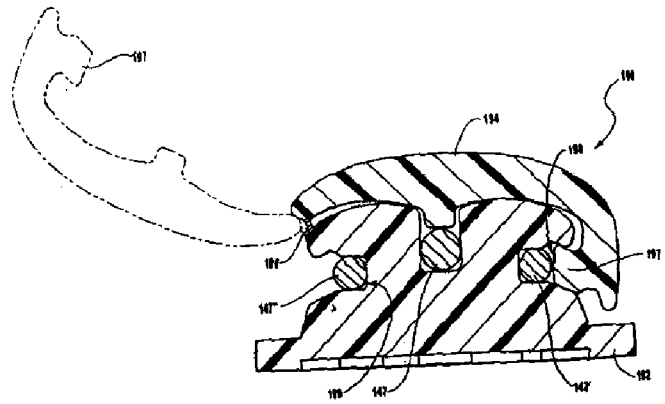

What is claimed and desired to be secured by United States Letters Patent is:

1. An orthodontic bracket comprising:
   a bracket base that includes first and second arch wire slots, each adapted to receive an arch wire therein; and
   a ligation cover integrally attached at one end to the bracket base, so that the bracket base and ligation cover form a single piece, and movable between an open, non-ligating position relative to the first and second arch wire slots and a closed, ligating position in which the first and second arch wire slots are at least partially occluded by the ligation cover, the first and second arch wire slots being open and completely non-occluded when the ligation cover is in the open, non-ligating position and remains integrally attached to the bracket base.

2. An orthodontic bracket as defined in claim 1, further including a third arch wire slot that is open and completely non-occluded when the ligation cover is in the open, non-ligating position and which remains open and non-occluded when the ligation cover is in the closed, ligating position.

3. An orthodontic bracket as defined in claim 2, wherein the bracket base further includes ligation structure that facilitates attachment of at least one ligature to the bracket base in a manner so as to ligate an arch wire within the third arch wire slot.

4. An orthodontic bracket as defined in claim 1, further including a third arch wire slot that is open and completely non-occluded when the ligation cover is in the open, non-ligating position and which is at least partially occluded when the ligation cover is in the closed, ligating position.

5. An orthodontic bracket as defined in claim 1, wherein the bracket base comprises at least one of metal, ceramic or plastic, wherein the ligation cover comprises at least one of metal or plastic.

6. An orthodontic bracket as defined in claim 1, wherein the bracket base comprises a rigid plastic material and the ligation cover comprises a flexible plastic material.

7. An orthodontic bracket as defined in claim 1, wherein an end of the ligation cover is hingedly attached to the bracket base such that the ligation cover is selectively rotatable about a hinge between the open, non-ligating position and the closed, ligating position.

8. An orthodontic bracket as defined in claim 7, wherein the ligation cover is hingedly attached to the bracket base by means of a film hinge of locally reduced cross-sectional thickness.

9. An orthodontic bracket as defined in claim 8, wherein the ligation cover and bracket base are molded as single, one-piece unit.

10. An orthodontic bracket as defined in claim 8, wherein the bracket base and ligation cover are separately formed and then joined together by a two-color molding process so as to yield an integral, one-piece bracket.

11. An orthodontic bracket as defined in claim 7, wherein the ligation cover is hingedly attached to the bracket base by means of a fiber hinge.

12. An orthodontic bracket as defined in claim 7, wherein the ligation cover is hingedly attached to the bracket base by means of an elastomeric adhesive interconnecting the ligation cover and bracket base.

13. An orthodontic bracket as defined in claim 1, wherein the ligation cover includes a bearing protrusion configured and positioned so as to engage one or more arch wires while the ligation cover is in the closed, ligating position.

14. An orthodontic bracket as defined in claim 13, wherein the ligation cover is configured so as to absorb mechanical energy from an arch wire when not entirely seated relative to the bracket base.

15. An orthodontic bracket as defined in claim 1, further including a spring connected at one end to the ligation cover and at an opposite end to the bracket base, the spring being positioned and tensioned relative to the ligation cover and bracket base so as to urge the ligation cover to remain closed while the closed, ligating position and to remain open while in the open, non-ligating position.

16. An orthodontic bracket comprising:
a bracket base that includes a first arch wire slot in a top of the bracket base and a second arch wire slot in a side of the bracket base so as to be oriented transversely to the first arch wire slot, each arch wire slot having an outer opening and a pair of side openings adapted to receive an arch wire therethrough;
a ligation cover hingedly attached to the bracket base and movable between an open, non-ligating position relative to the first and second arch wire slots and a closed, ligating position in which the outer openings of the first and second arch wire slots are at least partially covered and occluded by the ligation cover, the first and second arch wire slots being open and completely non-occluded when the ligation cover is in the open, non-ligating position.

17. An orthodontic bracket comprising:
a bracket base that includes first and second arch wire slots, each adapted to receive an arch wire therein;
a ligation cover hingedly attached to the bracket base by at least one of an integral hinge or a film hinge, so that the bracket base and ligation cover form a single piece, such that the ligation cover is selectively rotatable about the integral hinge or film hinge between an open, non-ligating position relative to the first and second archwire slots and a closed, ligating position in which the first and second arch wire slots are at least partially occluded by the ligation cover, the first and second arch wire slots being open and completely non-occluded when the ligation cover is in the open, non-ligating position.

18. An orthodontic bracket comprising:
a bracket base that includes first and second arch wire slots, each adapted to receive an arch wire therein;
a ligation cover movable between an open, non-ligating position relative to the first and second arch wire slots and a closed, ligating position in which the first and second arch wire slots are at least partially occluded by the ligation cover, the first and second arch wire slots being open and completely non-occluded when the ligation cover is in the open, non-ligating position; and
a third arch wire slot that is open and completely non-occluded when the ligation cover is in the open, non-ligating position and which remains open and non-occluded when the ligation cover is in the closed, ligating position.

19. An orthodontic bracket comprising:
a bracket base that includes first, second and third arch wire slots, each having an outer opening and a pair of side openings adapted to receive an arch wire therethrough;
a ligation cover hingedly attached to the bracket base and movable between an open, non-ligating position relative to the first, second and third arch wire slots and a closed, ligating position in which the outer openings of the first, second and third arch wire slots are at least partially occluded by the ligation cover, the first, second and third arch wire slots being open and completely non-occluded when the ligation cover is in the open, non-ligating position.

20. An orthodontic bracket comprising:
a bracket base that includes first and second arch wire slots, each adapted to receive an arch wire therein;
a ligation cover that is separate and completely detachable from the bracket base and movable between an open, non-ligating position relative to the first and second arch wire slots and a closed, ligating position in which the first and second arch wire slots are at least partially occluded by the ligation cover, the first and second arch wire slots being open and completely non-occluded when the ligation cover is in the open, non-ligating position; and
a leash that loosely interconnects the ligation cover and the bracket base.

21. An orthodontic bracket comprising:
a bracket base that includes first and second arch wire slots, each adapted to receive an arch wire therein;
a ligation cover hingedly attached to the bracket base by a fiber hinge or an elastomeric adhesive interconnecting the ligation cover and bracket base, the ligation cover being movable between an open, non-ligating position relative to the first and second arch wire slots and a closed, ligating position in which the first and second arch wire slots are at least partially occluded by the ligation cover, the first and second arch wire slots being open and completely non-occluded when the ligation cover is in the open, non-ligating position.

* * * * *

UNITED STATES PATENT AND TRADEMARK OFFICE
CERTIFICATE OF CORRECTION

PATENT NO. : 6,733,286 B2  
DATED : May 11, 2004  
INVENTOR(S) : Norbert Abels and Claus H. Backes It is certified that error appears in the above-identified patent and that said Letters Patent is hereby corrected as shown below:

The title page showing the illustrative figure should be deleted to be replaced with the attached title page.

Drawing,
Figure 8, replace Figure 8 with the figure depicted herein below.

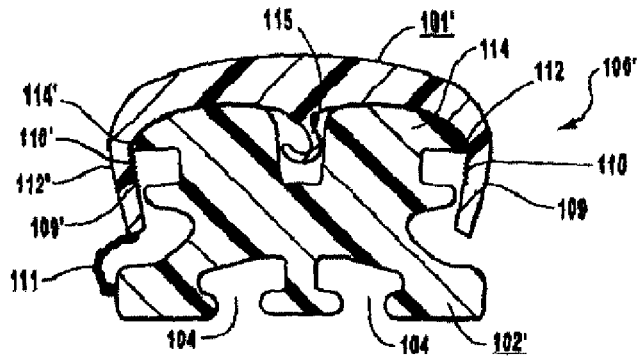

Figure 18C, replace Figure 18C with the figure depicted herein below.

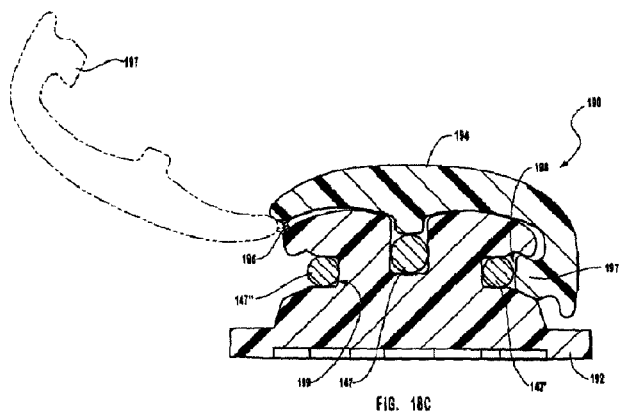

UNITED STATES PATENT AND TRADEMARK OFFICE
CERTIFICATE OF CORRECTION

PATENT NO. : 6,733,286 B2
DATED : May 11, 2004
INVENTOR(S) : Norbert Abels and Claus H. Backes It is certified that error appears in the above-identified patent and that said Letters Patent is hereby corrected as shown below:

Column 11,
Line 10, change "discussing" to -- discussion --

Column 13,
Lines 30 and 34, change "18" to -- 14 --

Column 16,
Line 61, change "(FIG. 1)" to -- (FIG. 5A) --

Column 18,
Line 54, change "then" to -- than --

Column 21,
Line 11, after "upper side" change "150" to -- 151 --

Column 22,
Line 13, change "50" to -- 150 --
Line 19, before "locking" change "to" to -- the --

Column 23,
Line 6, change "154" to -- 154' --
Line 10, change "151" to -- 150' --
Line 21, after "embodiment" insert -- of --

Column 26,
Line 48, change "SO" to -- so --

Column 28,
Line 6, change "cross-Page sectional" to -- cross-sectional --
Line 29, after "hinge may" insert -- be --

Column 29,
Line 11, change "my" to -- be --
Line 27, change "constitute" to -- constitutes --
Line 30, change "In" to -- It --
Line 49, change "preferably" to -- preferable --

UNITED STATES PATENT AND TRADEMARK OFFICE
CERTIFICATE OF CORRECTION

PATENT NO. : 6,733,286 B2
DATED : May 11, 2004
INVENTOR(S) : Norbert Abels and Claus H. Backes It is certified that error appears in the above-identified patent and that said Letters Patent is hereby corrected as shown below:

Column 30,
Line 43, change "In" to -- It --

Column 31,
Line 13, change "make" to -- made --

Column 32,
Line 14, change "Example" to -- Examples --

Column 33,
Line 42, change "while the closed" to -- while in the closed --

Signed and Sealed this

Ninth Day of August, 2005

JON W. DUDAS
*Director of the United States Patent and Trademark Office*

(12) United States Patent
Abels et al.

(10) Patent No.: US 6,733,286 B2
(45) Date of Patent: *May 11, 2004

(54) SELF-LIGATING ORTHODONTIC BRACKETS THAT HAVE MULTIPLE INITIALLY OPEN ARCH WIRE SLOTS LIGATABLE WITH A SINGLE COVER

(76) Inventors: Norbert Abels, Talstrasse 7, 66424 Homburg (DE); Claus H. Backes, St. Wendeler Strasse 45, 66113 Saarbrücken (DE)

(*) Notice: Subject to any disclaimer, the term of this patent is extended or adjusted under 35 U.S.C. 154(b) by 92 days.

This patent is subject to a terminal disclaimer.

(21) Appl. No.: 09/952,826
(22) Filed: Sep. 12, 2001
(65) Prior Publication Data

US 2002/0110774 A1 Aug. 15, 2002

Related U.S. Application Data

(63) Continuation-in-part of application No. 09/914,737, filed as application No. PCT/EP01/08489 on Jul. 23, 2001, now abandoned, application No. 09/952,826, which is a continuation-in-part of application No. 09/784,525, filed on Feb. 15, 2001, now Pat. No. 6,607,383.

(51) Int. Cl.$^7$ .................................................. A61C 3/00
(52) U.S. Cl. ........................................... 433/11; 433/15
(58) Field of Search .................... 433/8, 9, 10, 11, 433/12, 13, 14, 15, 16, 17

(56) References Cited

U.S. PATENT DOCUMENTS

| | | |
|---|---|---|
| 2,011,575 A | 8/1935 | Ford |
| 2,230,315 A * | 2/1941 | Winslow ............... 433/11 |
| 3,128,552 A | 4/1964 | Broussard |
| 3,218,713 A | 11/1965 | Wallshein |
| 3,724,074 A | 4/1973 | Wallshein |
| 3,748,740 A | 7/1973 | Wildman |

(List continued on next page.)

FOREIGN PATENT DOCUMENTS

| | | |
|---|---|---|
| DE | 1 184 451 | 12/1964 |
| DE | 23 57 573 | 5/1975 |
| DE | G 91 12 872.2 | 3/1992 |
| DE | 296 08 349 U1 | 11/1996 |
| EP | 0 714 639 A3 | 5/1996 |
| EP | 0 714 639 A2 | 6/1996 |
| WO | WO 94/00072 | 1/1994 |
| WO | WO 00/33760 | 6/2000 |
| WO | WO 00/76419 | 12/2000 |

OTHER PUBLICATIONS

Konstruieren mit unststoffen, Gunter Erhard, Carl Hanser Verlag München Wien, pp. 314–329, 1999.

*Primary Examiner*—John J. Wilson
(74) *Attorney, Agent, or Firm*—Workman Nydegger

(57) ABSTRACT

Self ligating orthodontic brackets include a bracket base and a ligation cover which interacts with the base in order to provide ligation of at least one arch wire associated with the base. The orthodontic brackets may include one or more of the following improved features: (1) a film hinge about which a ligation cover may rotate; (2) a bearing spring or other flexible feature associated with the ligation cover to provide active ligation; (3) a ligation cover that has sufficient flexibility and resilience to facilitate locking and unlocking relative to the base; (4) a spring or spring-like feature that provides resistance to rotation of the ligation cover relative to the base; (5) a bracket base and ligation cover formed from different types of plastic materials; (6) two or more initially open arch wire slots that can be ligated by a single ligation cover; or (7) a safety locking feature that holds the ligation cover more tightly to the bracket in response to increased arch wire pressure. The orthodontic brackets may comprise one or more different materials, such as plastic, metal or ceramic and may be manufactured as a single piece or in multiple pieces that are later joined together.

21 Claims, 27 Drawing Sheets